US011778902B2

(12) United States Patent
Duan et al.

(10) Patent No.: US 11,778,902 B2
(45) Date of Patent: Oct. 3, 2023

(54) ORGANIC ELECTROLUMINESCENT DEVICES

(71) Applicants: KUNSHAN GO-VISIONOX OPTO-ELECTRONICS CO., LTD., Kunshan (CN); TSINGHUA UNIVERSITY, Beijing (CN)

(72) Inventors: Lian Duan, Beijing (CN); Xiaozeng Song, Beijing (CN); Dongdong Zhang, Beijing (CN); Guomeng Li, Kunshan (CN)

(73) Assignees: Kunshan Go-Visionox Opto-Electronics Co., Ltd., Kunshan (CN); Tsinghua University, Beijing (CN)

( * ) Notice: Subject to any disclaimer, the term of this patent is extended or adjusted under 35 U.S.C. 154(b) by 662 days.

(21) Appl. No.: 16/558,691

(22) Filed: Sep. 3, 2019

(65) Prior Publication Data
US 2020/0006666 A1    Jan. 2, 2020

Related U.S. Application Data

(63) Continuation of application No. PCT/CN2018/088881, filed on May 29, 2018.

(30) Foreign Application Priority Data

Dec. 8, 2017  (CN) .......................... 201711302958.6

(51) Int. Cl.
H10K 85/60      (2023.01)
C07D 209/86     (2006.01)
(Continued)

(52) U.S. Cl.
CPC ......... H10K 85/636 (2023.02); C07D 209/86 (2013.01); C07D 401/14 (2013.01);
(Continued)

(58) Field of Classification Search
CPC ............. H01L 51/5012; H01L 51/5016; H01L 51/0061; H01L 51/006; H01L 51/0067;
(Continued)

(56) References Cited

U.S. PATENT DOCUMENTS 11,063,224 B2 *   7/2021   Duan .................. H01L 51/0061
2016/0087227 A1 * 3/2016   Kim .................... H01L 51/0074
                                                              257/40
(Continued)

FOREIGN PATENT DOCUMENTS

CN         1914294 A      2/2007
CN       105895811 A      8/2016
(Continued)

OTHER PUBLICATIONS

Ikemizu D et al., machine translation of JP-2010215759-A (2010) pp. 1-178. (Year: 2010).*
(Continued)

*Primary Examiner* — Dylan C Kershner
(74) *Attorney, Agent, or Firm* — Maier & Maier, PLLC

(57) ABSTRACT

The present disclosure relates to the field of display technologies, and particularly discloses an organic electroluminescent device. The organic electroluminescent device has a first electrode, a second electrode, and an organic functional layer. The organic functional layer comprises a light-emitting layer. The light-emitting layer comprises at least a host material and a guest material. The host material comprises an exciplex composed of a donor molecule and a receptor molecule, wherein the donor molecule and/or the receptor molecule contains a large steric hindrance substituent group X for increasing an inter-molecular distance between the donor molecule and the receptor molecule, which enables to enhance Foster energy transfer to the guest material molecule, improve device efficiency, inhibit Triplet-Polaron
(Continued)

Annihilate Annihilation (TPA), and prolong the device lifetime.

16 Claims, 4 Drawing Sheets

(51) Int. Cl.
| | | |
|---|---|---|
| C07D 401/14 | (2006.01) | |
| C07D 403/10 | (2006.01) | |
| C07F 7/08 | (2006.01) | |
| C09K 11/06 | (2006.01) | |
| H10K 85/40 | (2023.01) | |
| H10K 50/11 | (2023.01) | |
| H10K 101/10 | (2023.01) | |
| H10K 101/30 | (2023.01) | |

(52) U.S. Cl.
CPC .......... *C07D 403/10* (2013.01); *C07F 7/0812* (2013.01); *C09K 11/06* (2013.01); *H10K 85/40* (2023.02); *H10K 85/633* (2023.02); *H10K 85/654* (2023.02); *H10K 85/6572* (2023.02); *C09K 2211/1018* (2013.01); *H10K 50/11* (2023.02); *H10K 85/626* (2023.02); *H10K 2101/10* (2023.02); *H10K 2101/30* (2023.02)

(58) Field of Classification Search
CPC ............. H01L 51/0072; H01L 51/0094; H01L 51/0058; H01L 2251/552; C07D 209/86; C07D 401/14; C07D 403/10; C07F 7/0812; C09K 11/06; C09K 2211/1018; H10K 85/636; H10K 85/654; H10K 85/633; H10K 85/6572; H10K 85/40; H10K 85/626; H10K 50/11; H01K 2101/10; H01K 2101/30
See application file for complete search history.

(56) References Cited

U.S. PATENT DOCUMENTS

| 2016/0164020 A1* | 6/2016 | Kim | ................. C09K 11/06 257/40 |
| 2017/0194585 A1* | 7/2017 | Yan | .................. H01L 51/0051 |

FOREIGN PATENT DOCUMENTS

| CN | 106920884 A | | 7/2017 |
| JP | 2000103786 A | | 4/2000 |
| JP | 2001006878 A | | 1/2001 |
| JP | 2010215759 A | * | 9/2010 |
| JP | 2016092194 A | | 5/2016 |

OTHER PUBLICATIONS

Moonsin et al., "Carbazole dendronised triphenylamines as solution processed high Tg amorphous hole-transporting materials for organic electroluminescent devices" Chem. Commun., 2012, 48, 3382-3384. (Year: 2012).*

Ding et al., "Design of star-shaped molecular architectures based on carbazole and phosphine oxide moieties: towards amorphous bipolar hosts with high triplet energy for efficient blue electrophosphorescent devices" J. Mater. Chem., 2010, 20, 8126-8133. (Year: 2010).*

Zhang et al., "Simultaneous Enhancement of Efficiency and Stability of Phosphorescent OLEDs Based on Efficient Förster Energy Transfer from Interface Exciplex" ACS Appl. Mater. Interfaces 2016, 8, 3825-3832. (Year: 2016).*

International Search Report dated Aug. 1, 2018 in corresponding International application No. PCT/CN2018/088881; 4 pages.

Chinese Office Action dated Sep. 29, 2019, in connection with corresponding CN Application No. 201711302958.6 (9 pgs., including machine-generated English translation).

* cited by examiner

ORGANIC ELECTROLUMINESCENT DEVICES

CROSS-REFERENCE TO RELATED APPLICATION

This application is a continuation of International Application No. PCT/CN2018/088881 filed on May 29, 2018, which claims priority to Chinese patent application No. 201711302958.6 filed on Dec. 8, 2017. Both applications are incorporated herein by reference in their entireties.

TECHNICAL FIELD

The present disclosure relates to the field of display technologies.

BACKGROUND

Organic electroluminescent devices (also called Organic Light-Emitting Diodes, OLED) have a great application prospect in the field of display and illumination and are increasingly concerned by people due to the advantages of ultra-thin, light weight, low energy consumption, active illumination, wide viewing angle, and fast response.

SUMMARY

Therefore, the technical problems to be solved by the present disclosure are to overcome the large singlet-triplet energy level gap ($\Delta E_{ST}$) of an exciplex TADF host material, the low RISC rate $k_{RISC}$, the severe Triplet-Polaron Annihilate (TPA) in the light-emitting layer, and the problem that performances such as the device efficiency and the service life need to be further improved.

For this purpose, the present disclosure provides an organic electroluminescent device, comprising a first electrode, a second electrode, and an organic functional layer located between the first electrode and the second electrode, wherein the organic functional layer comprises a light-emitting layer; the light-emitting layer comprising a host material and a guest material; the host material being an exciplex composed of a donor molecule and a receptor molecule; and the donor molecule and/or the receptor molecule containing a plurality of steric hindrance groups.

Optionally, the donor molecule is a compound (having a hole transport property) containing at least one of carbazolyl, triphenylaminyl, and aryl. The receptor molecule is a compound (having an electronic transport property) containing at least one of pyrimidinyl, triazinyl, oxadiazolyl, pyridyl, carbazolyl, aryl, cyano, acridinyl, dibenzothiophenyl, triphenylphosphonyl, and triphenylboryl.

Optionally, the donor molecule employs any one of the following molecular structures:

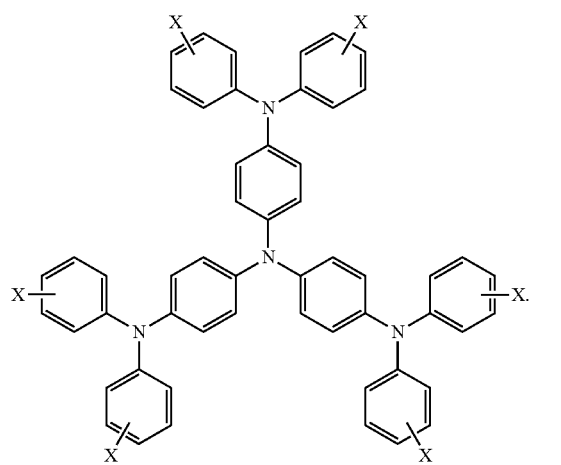

(D-1)

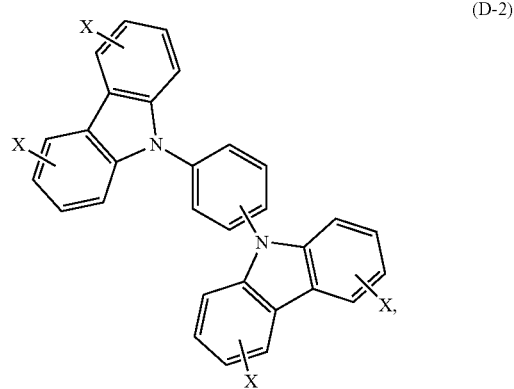

(D-2)

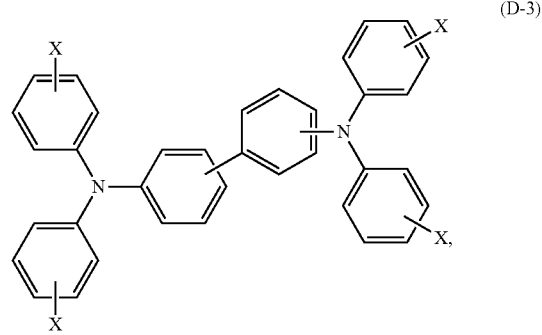

(D-3)

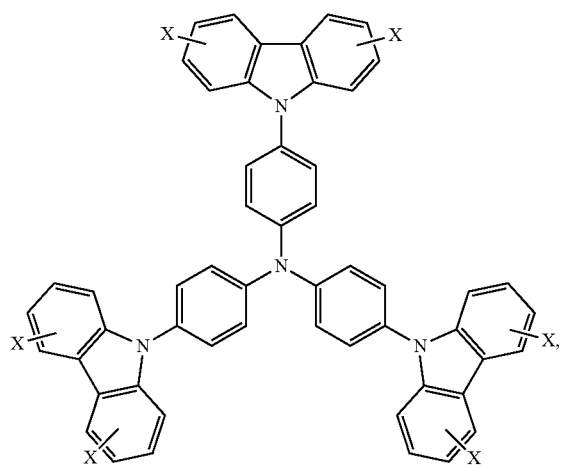
(D-4)
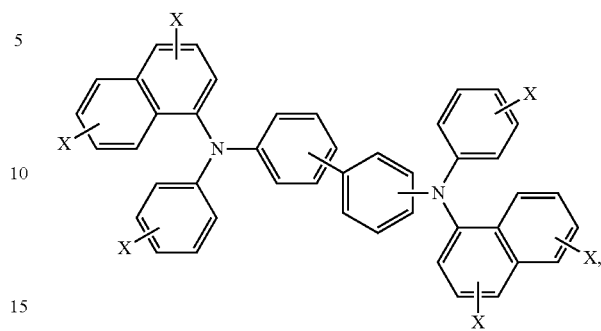
(D-7)
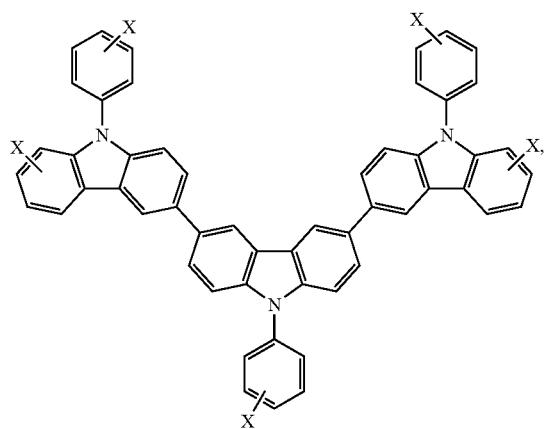
(D-5)
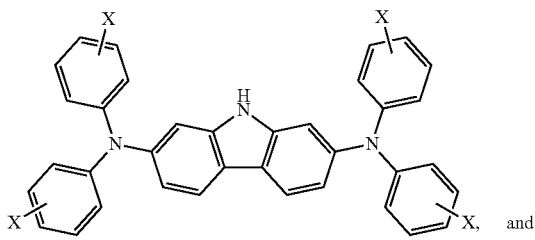
(D-8)
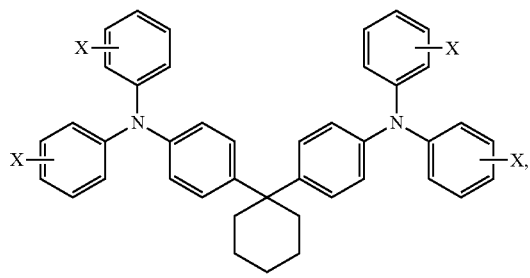
(D-6)
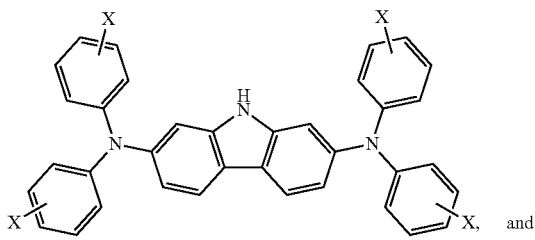
(D-9)
wherein X in the above molecular structures is hydrogen or a steric hindrance group, and at least one X is a steric hindrance group.

Optionally, the donor molecule employs any one of the following structures:
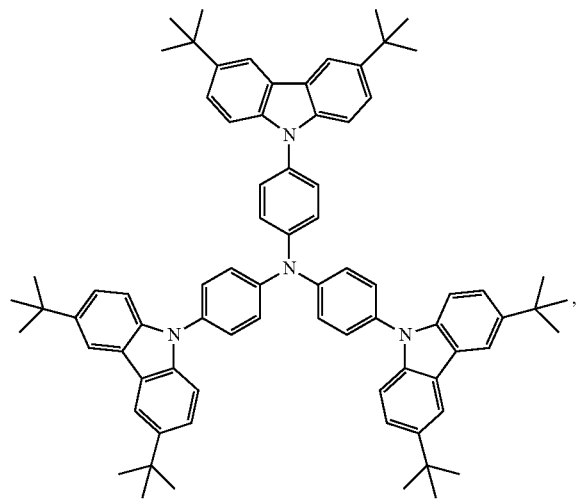
(1-1)
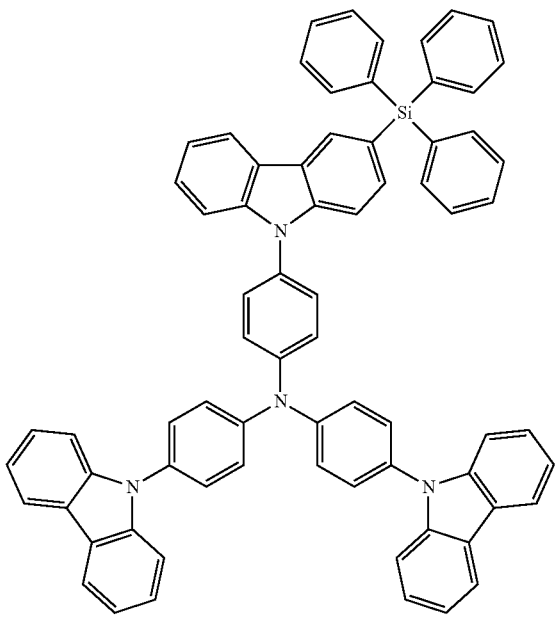
(1-2)
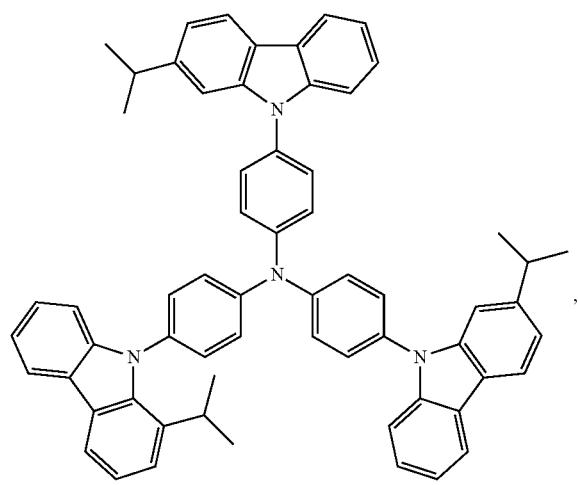
(1-3)
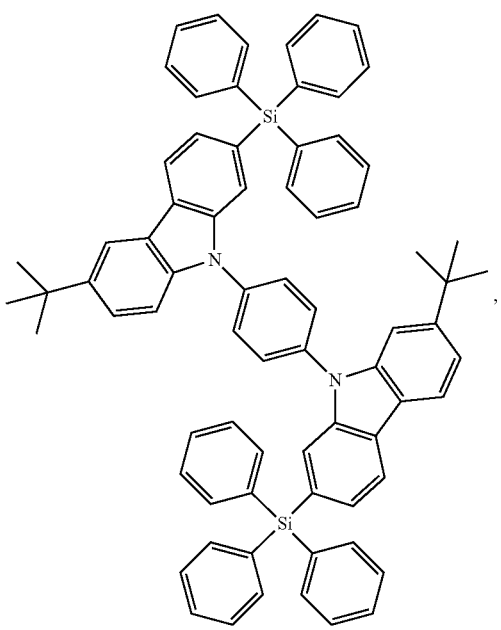
(1-4)

(1-5)
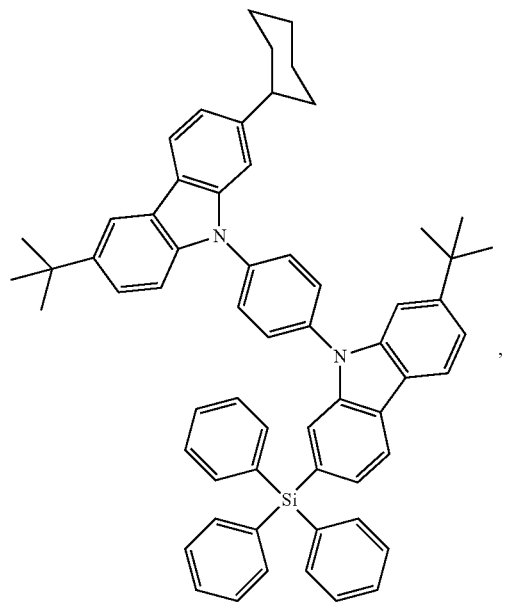
(1-6)
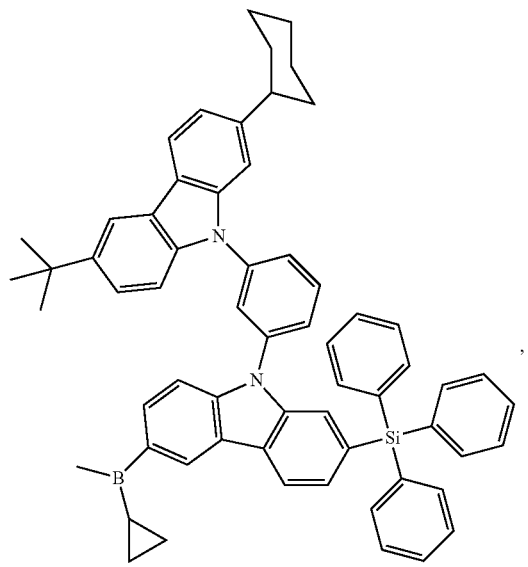
(1-7)
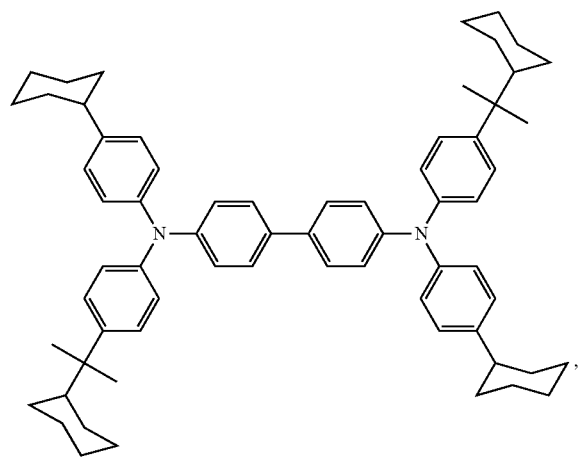
(1-8)
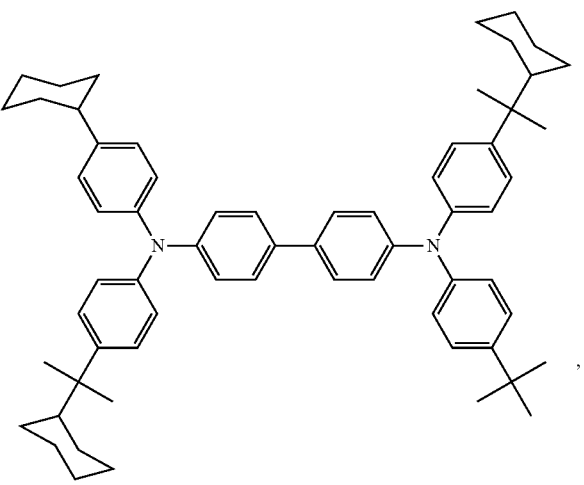

-continued
(1-9)
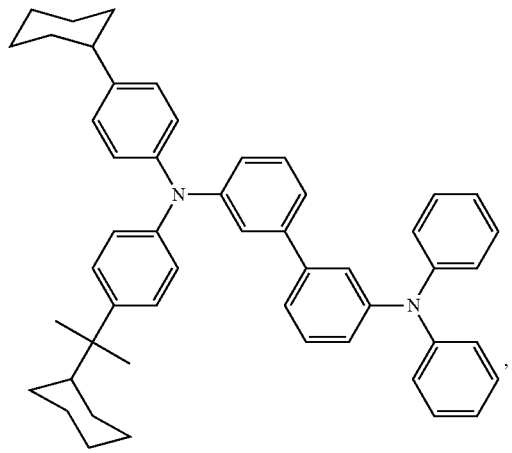
(1-10)
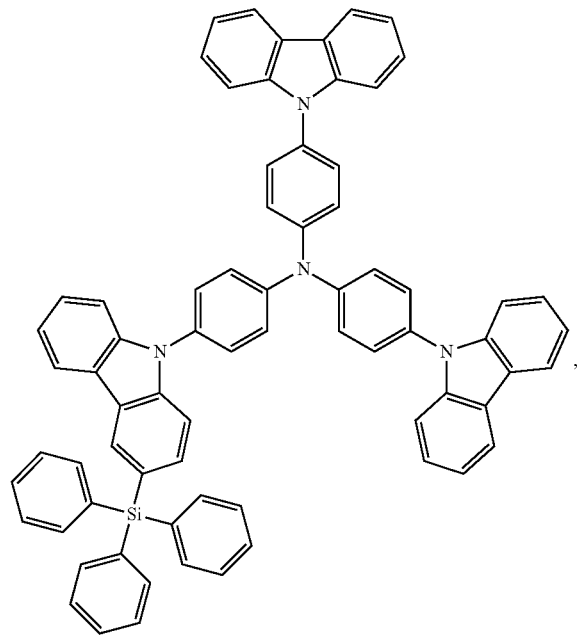
(1-11)
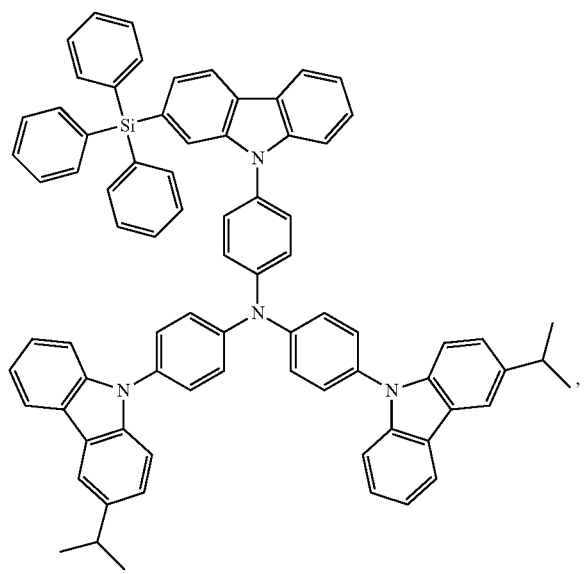
(1-12)
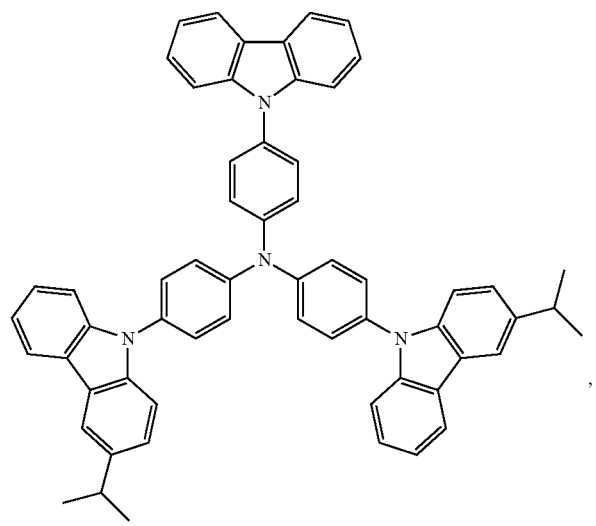

(1-13)
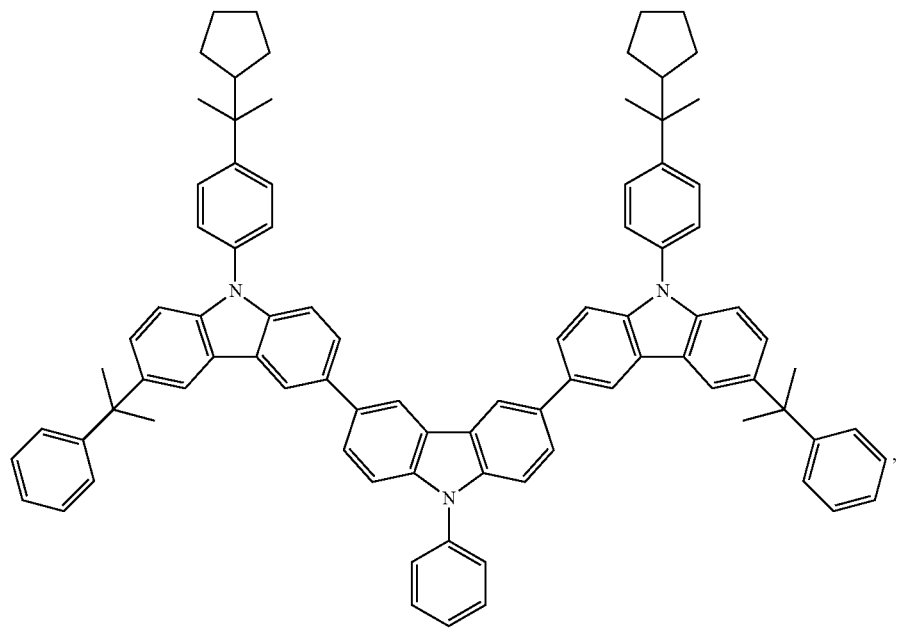
(1-14)
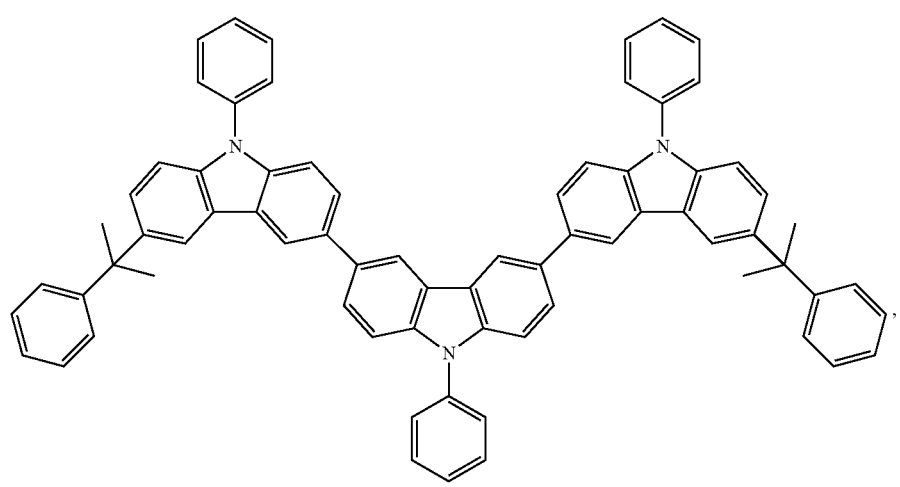
(1-15)
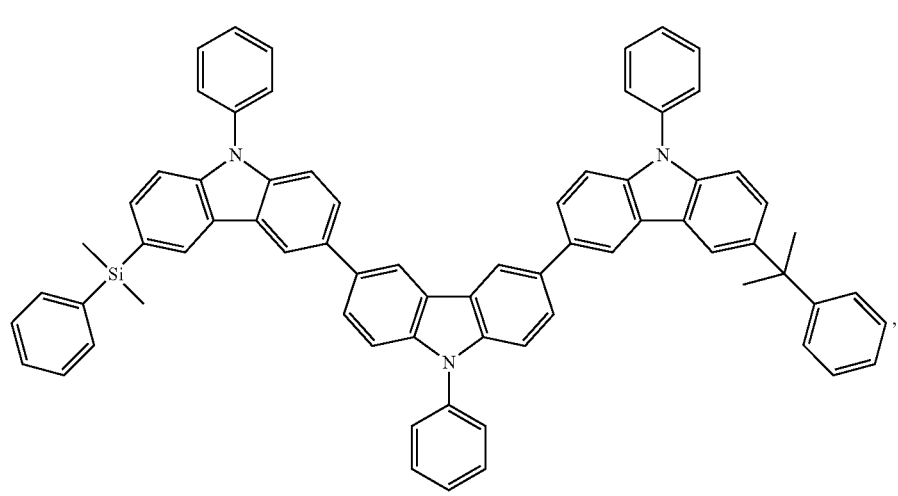

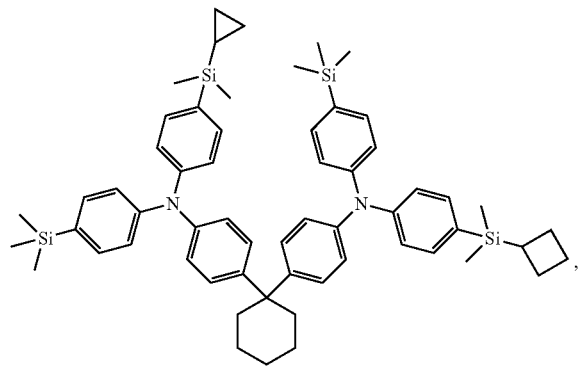
(1-16)
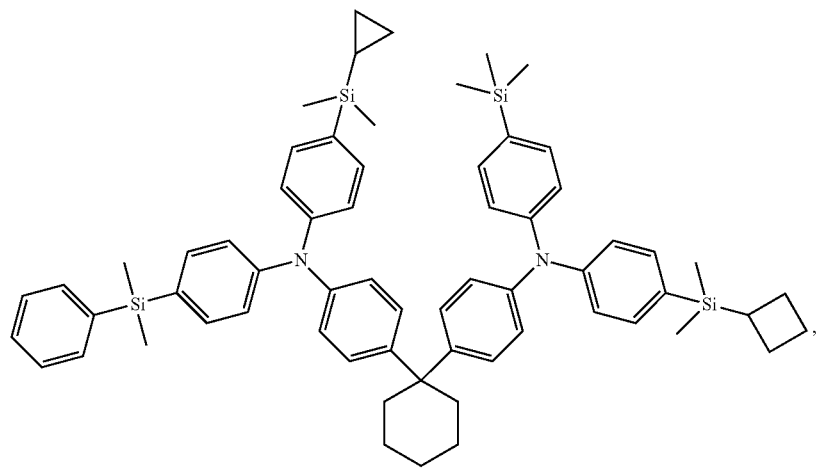
(1-17)
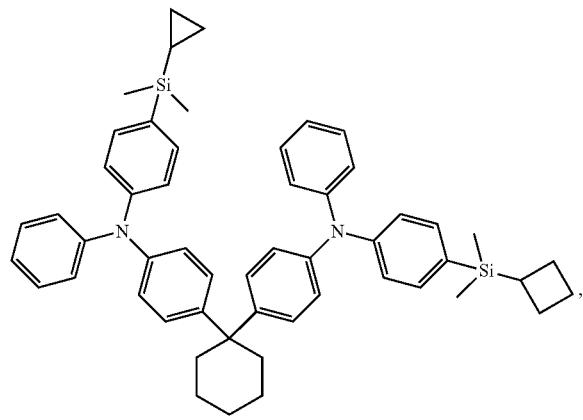
(1-18)
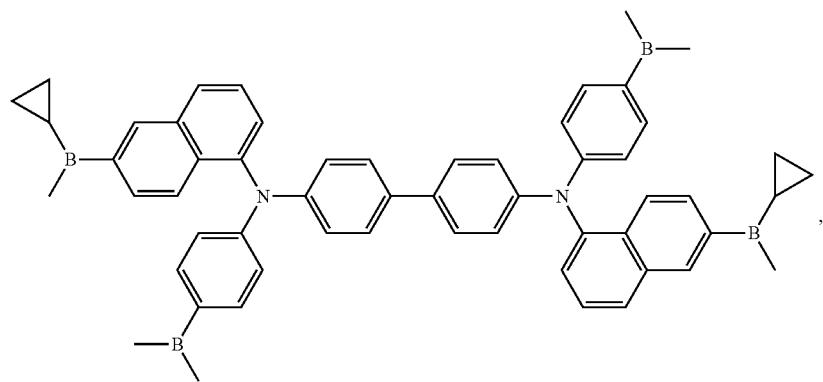
(1-19)

-continued
(1-20)
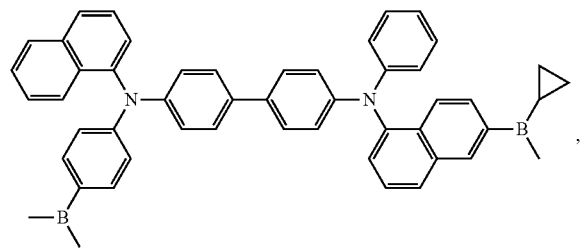
(1-21)
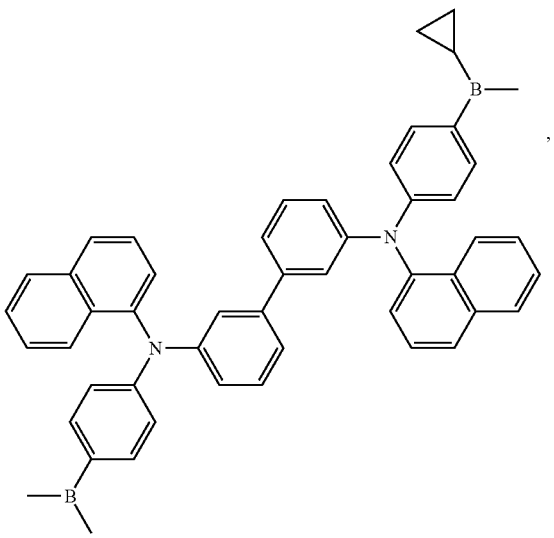
(1-22)
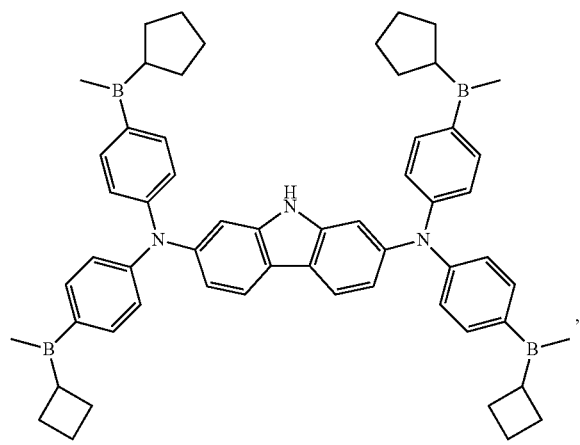
(1-23)
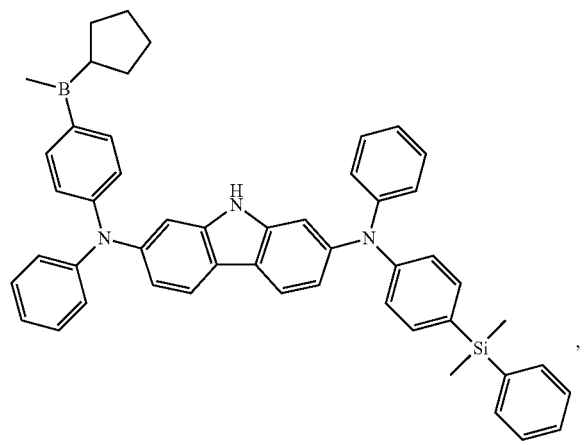
(1-24)
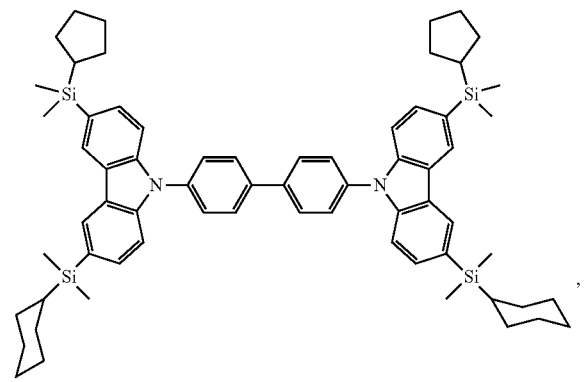
(1-25)

-continued
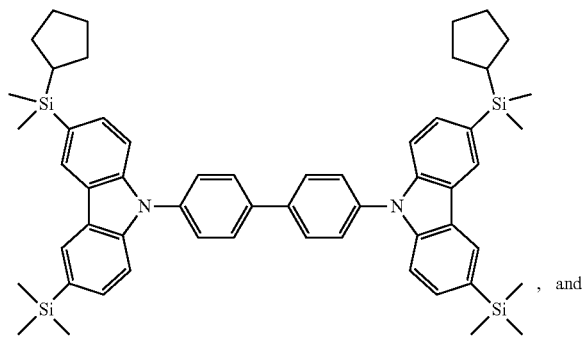
(1-26)
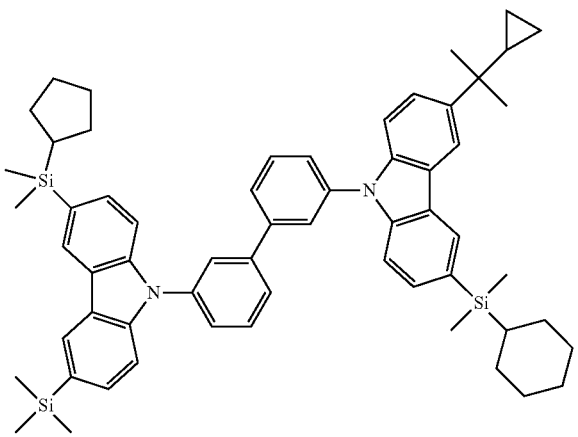
(1-27)
, and
Optionally, the receptor molecule is a compound containing at least one of pyrimidinyl, triazinyl, oxadiazolyl, pyridyl, carbazolyl, aryl, cyano, acridinyl, dibenzothiophenyl, triphenylphosphonyl, and triphenylboryl.
Optionally, the receptor molecule employs any one of the following molecular structures:
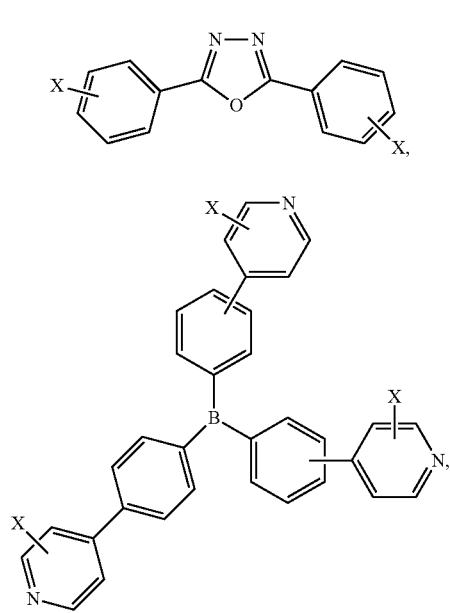
(A-1)
(A-2)
(A-3)
-continued
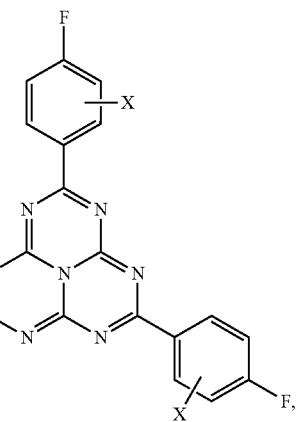
(A-4)
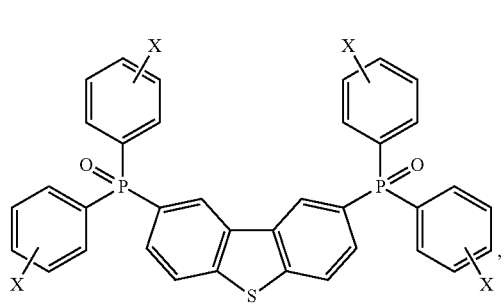
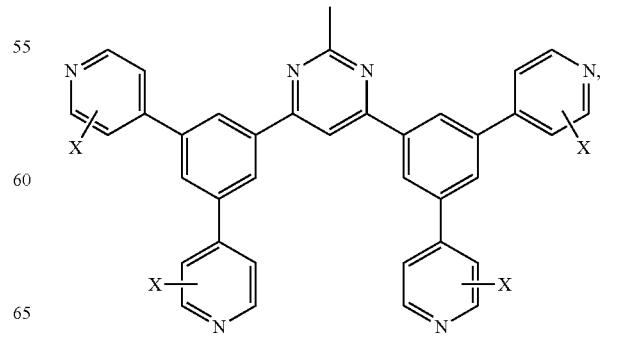
(A-5)

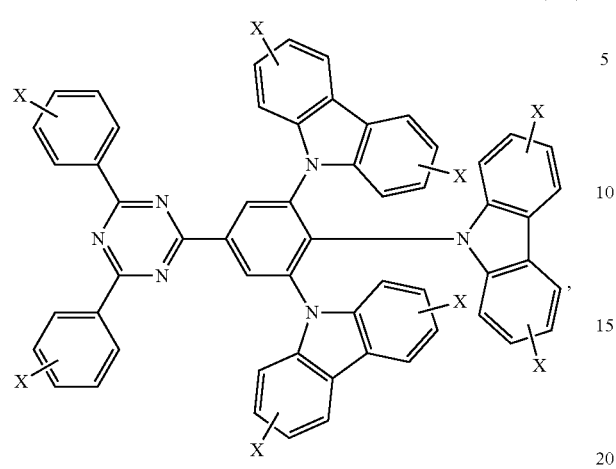
(A-6)
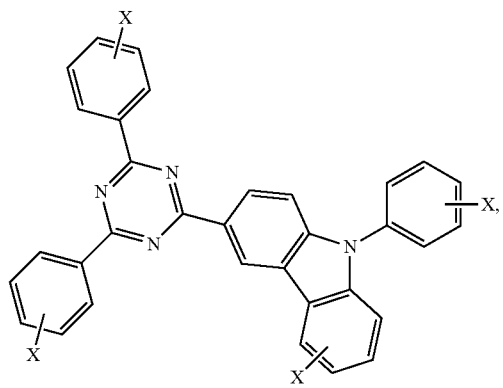
(A-9)
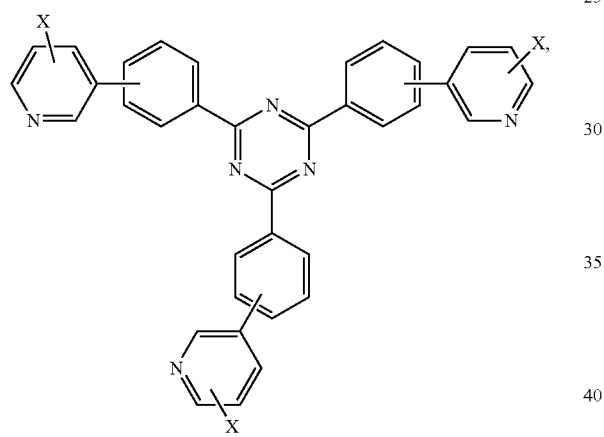
(A-7)
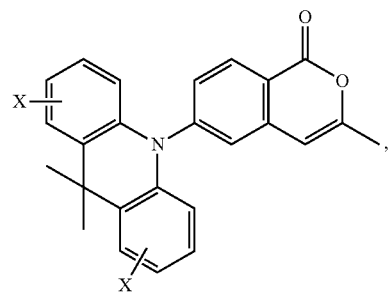
(A-10)
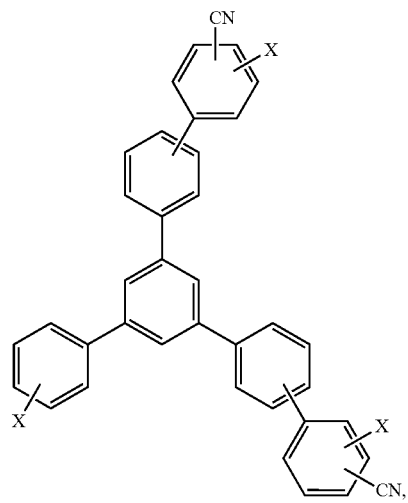
(A-8)
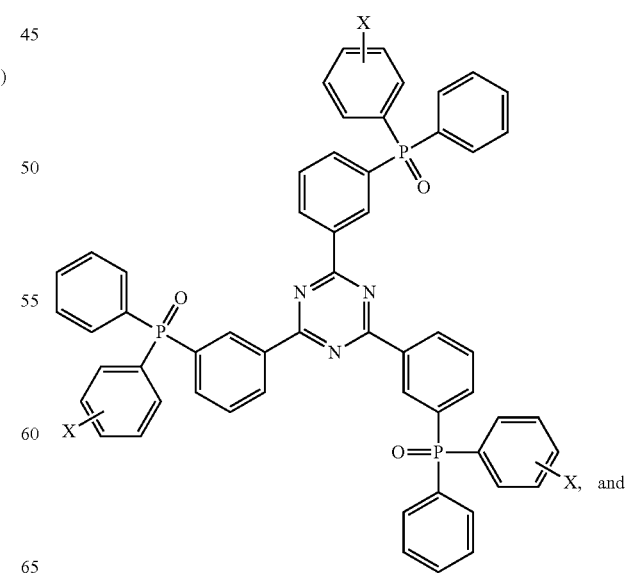
(A-11)
and

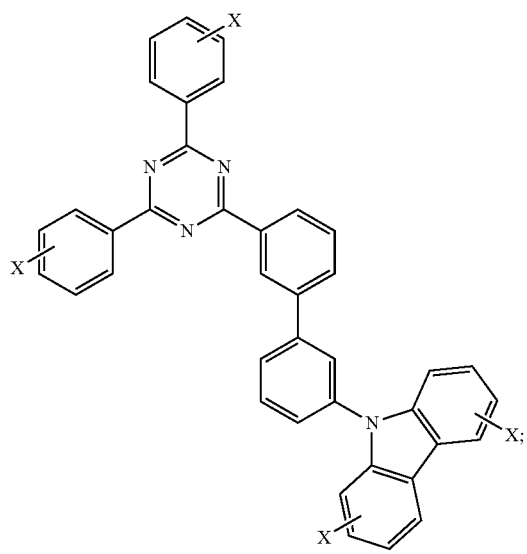
(A-12)
wherein X in the above molecular structures is hydrogen or a steric hindrance group, and at least one X is a steric hindrance group.
Optionally, the receptor molecule employs any one of the following structures:
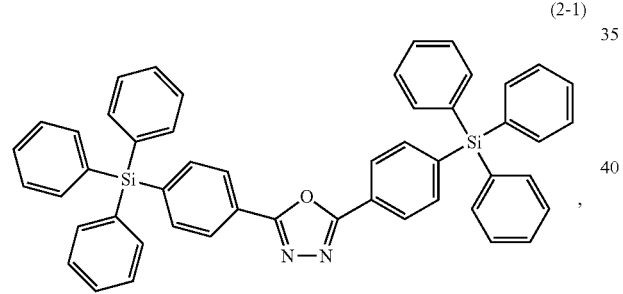
(2-1)
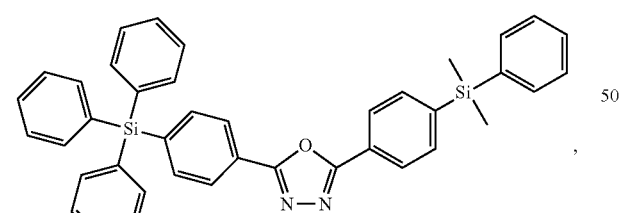
(2-2)
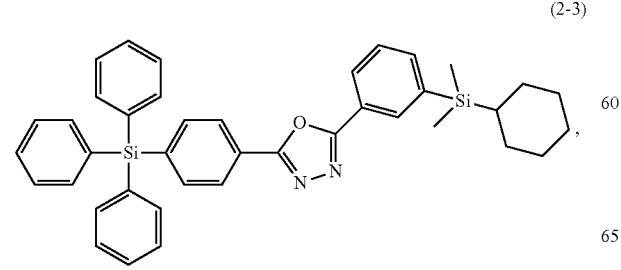
(2-3)
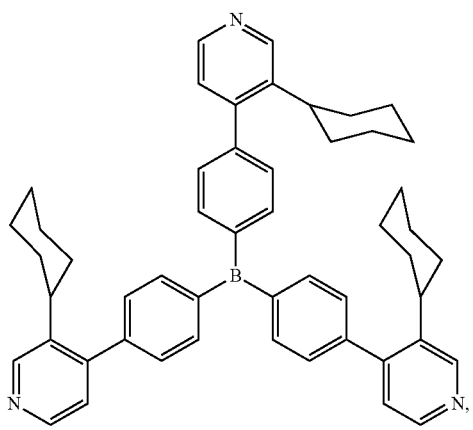
(2-4)
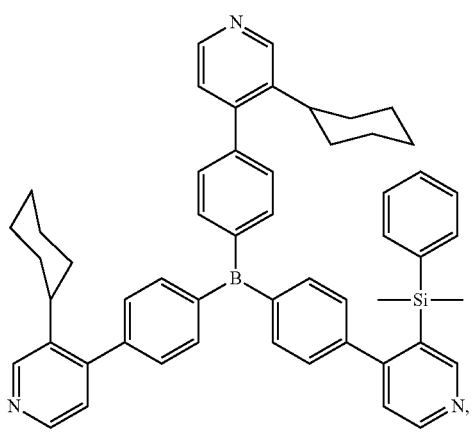
(2-5)
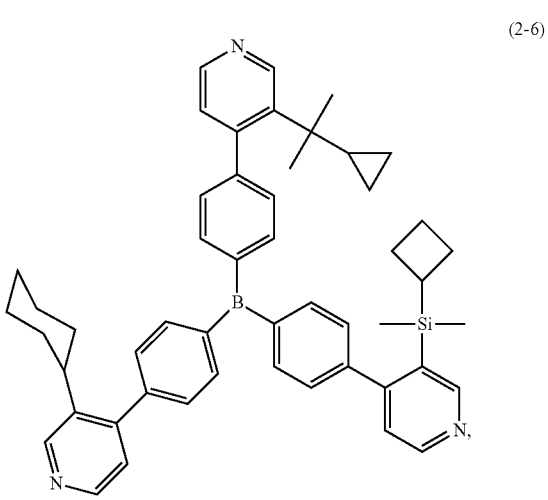
(2-6)

(2-7)
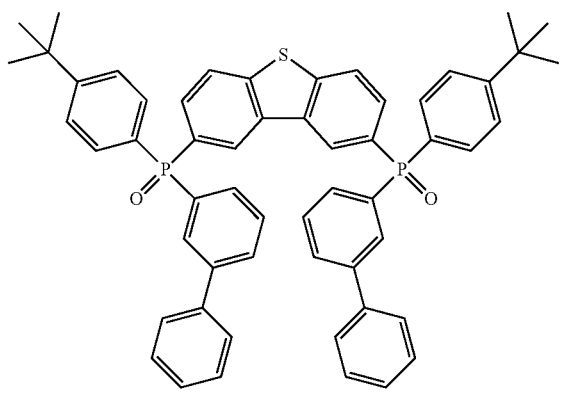
(2-8)
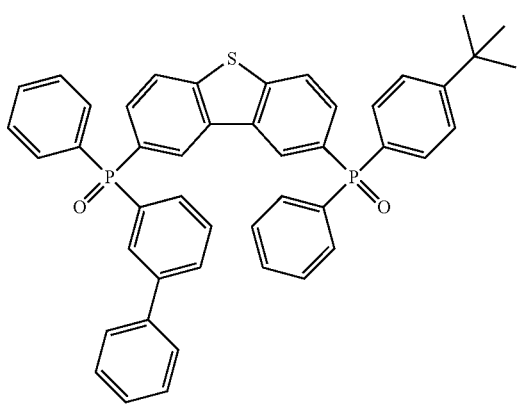
(2-9)
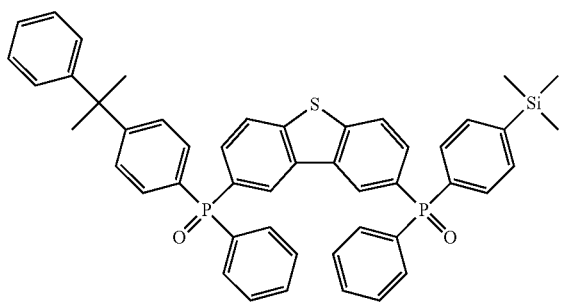
(2-10)
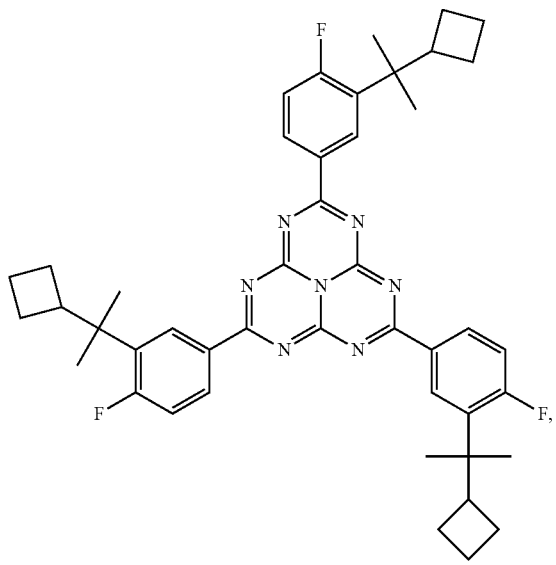
(2-11)
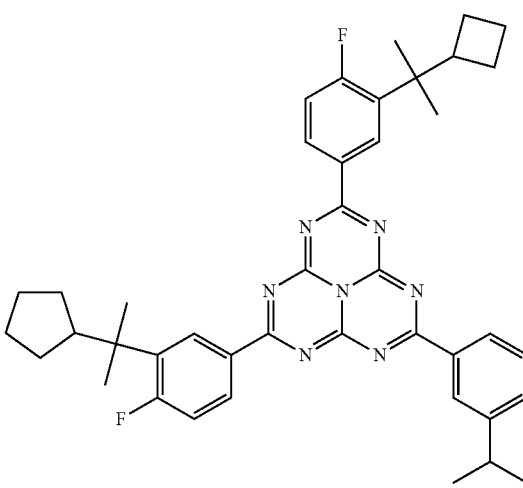
(2-12)
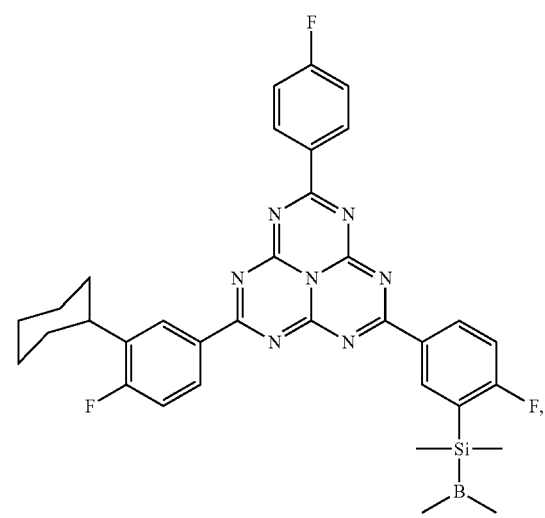

(2-13)
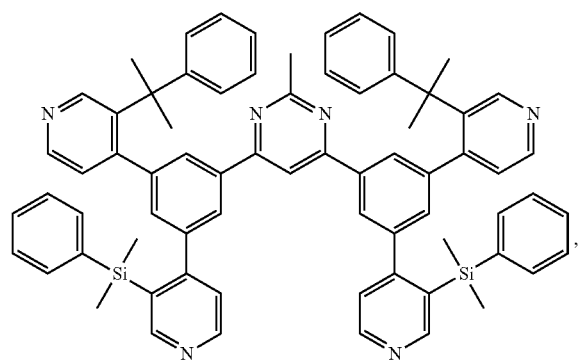
(2-14)
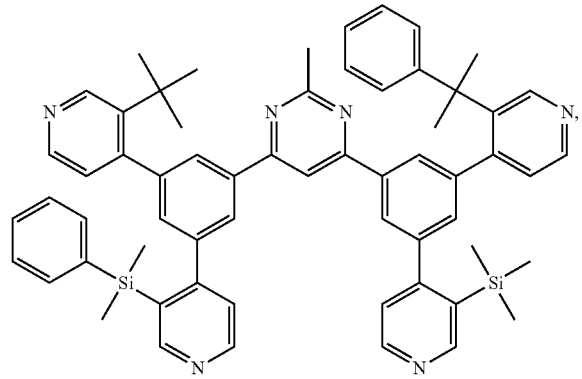
(2-15)
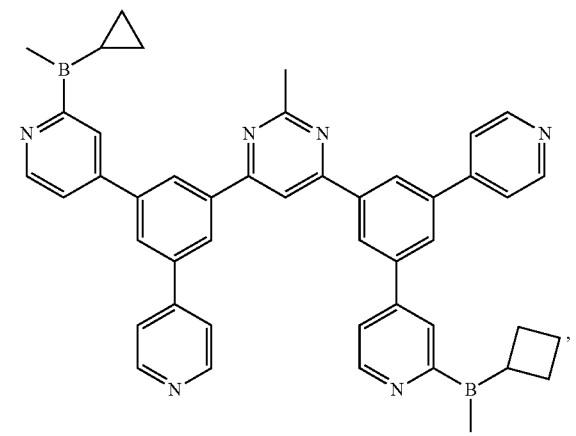
(2-16)
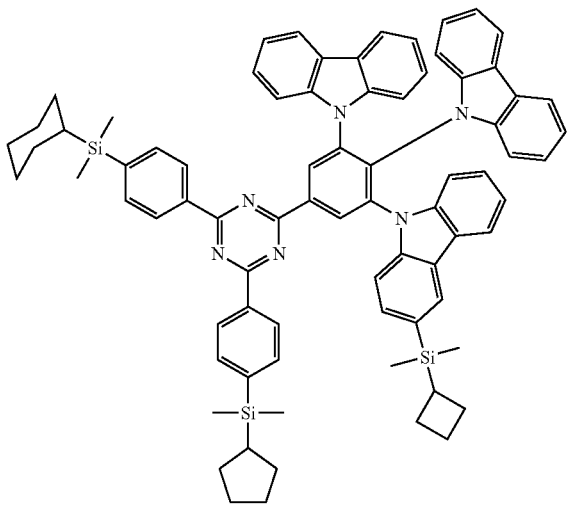
(2-17)
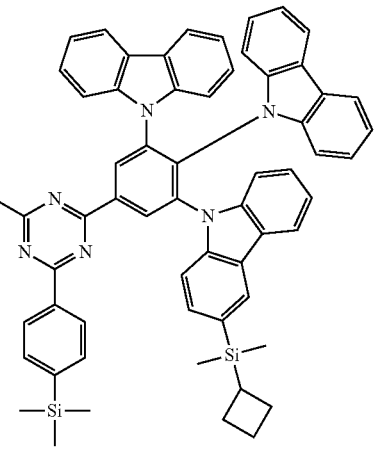
(2-18)
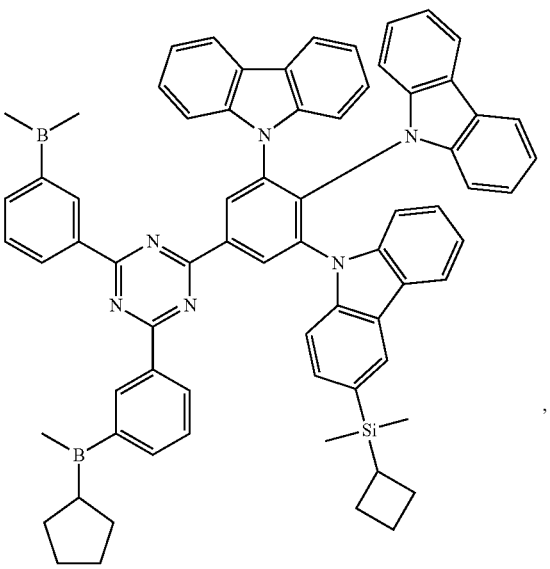

(2-19)
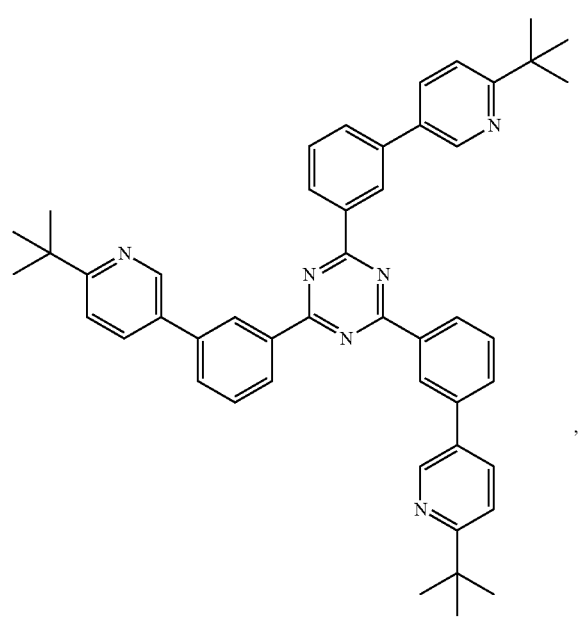
(2-21)
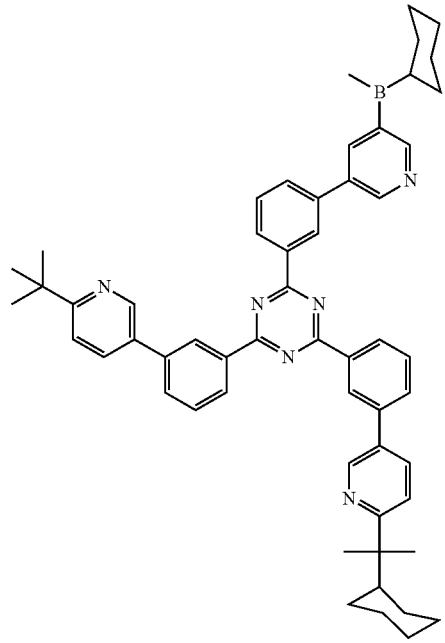
,
(2-20)
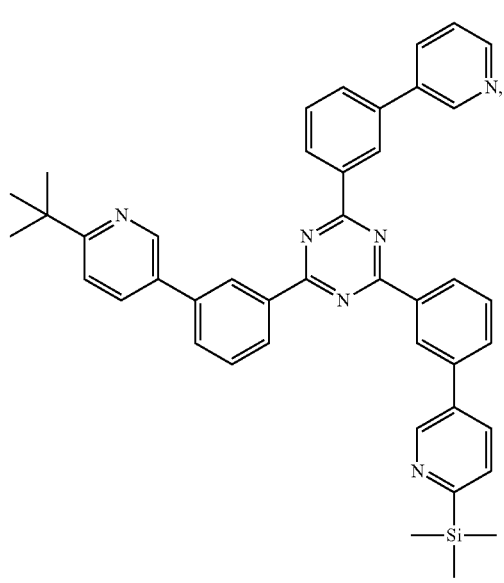
(2-22)
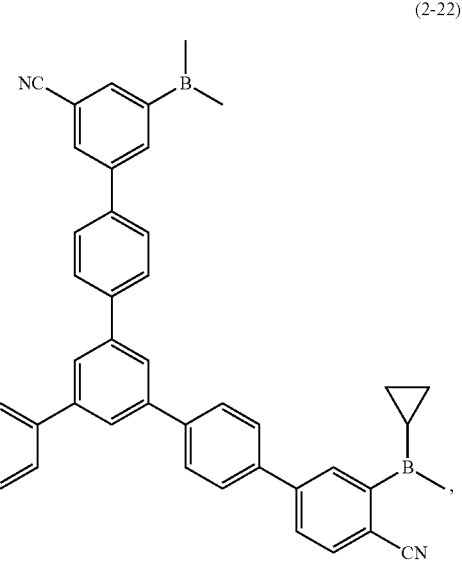
, (2-23)
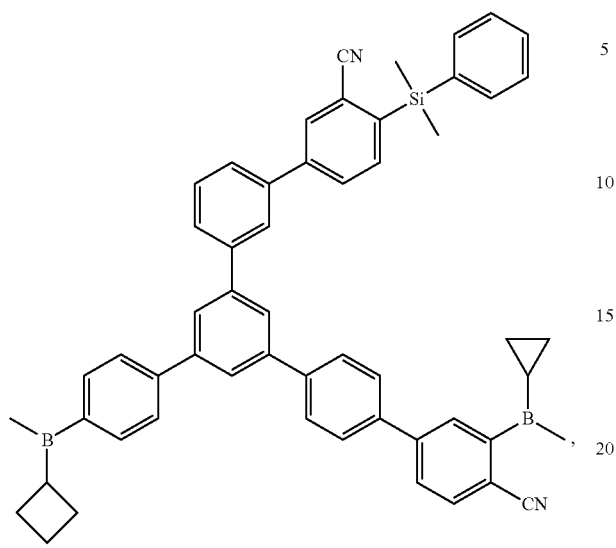
(2-24)
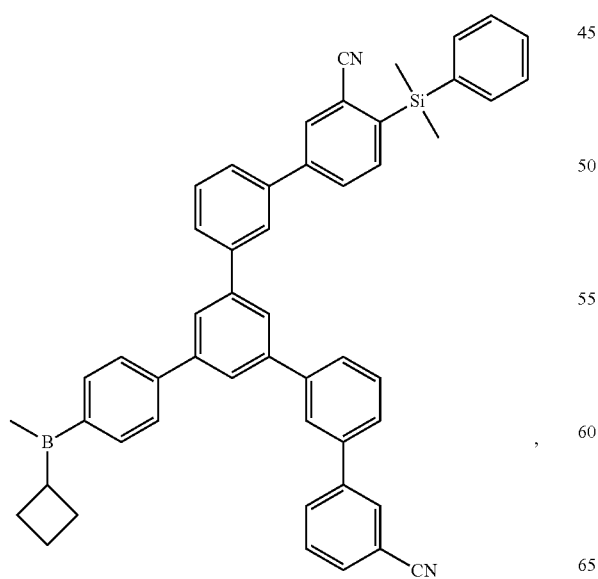
(2-25)
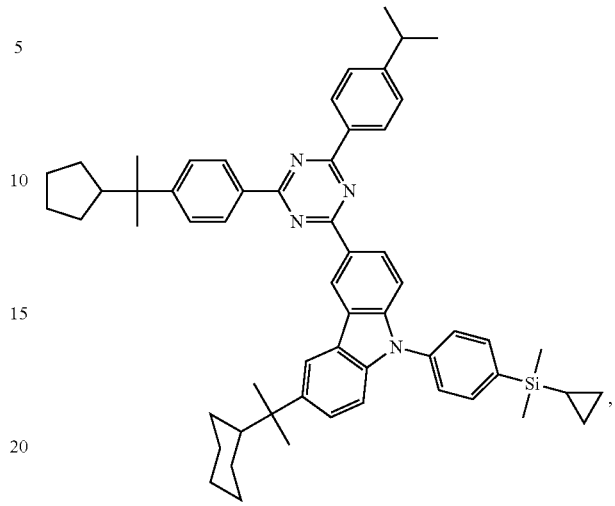
(2-26)
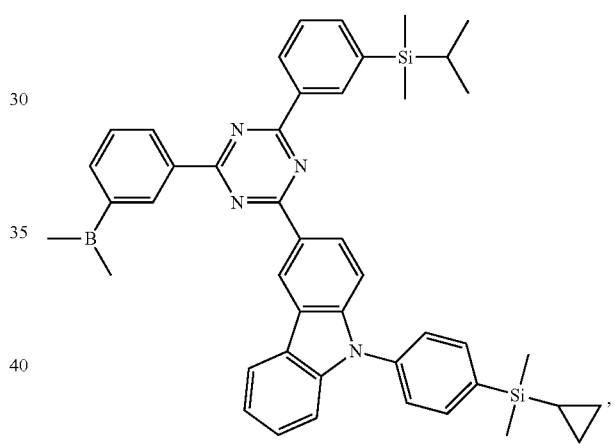
(2-27)
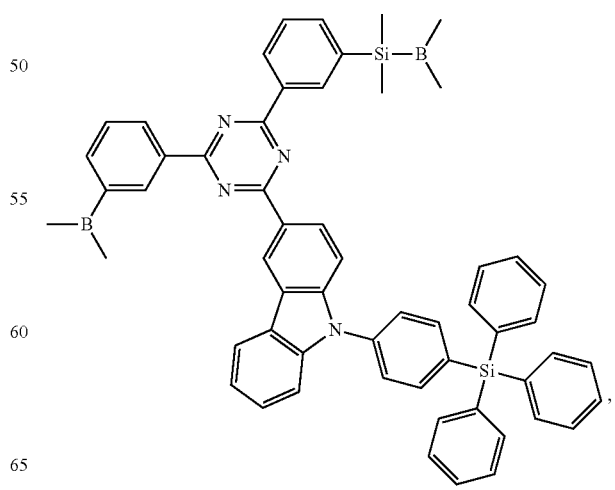

(2-28)
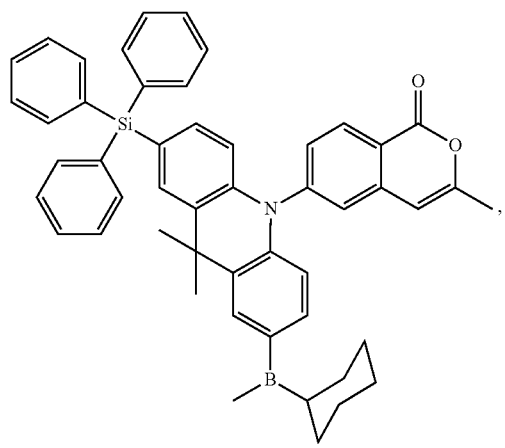
(2-31)
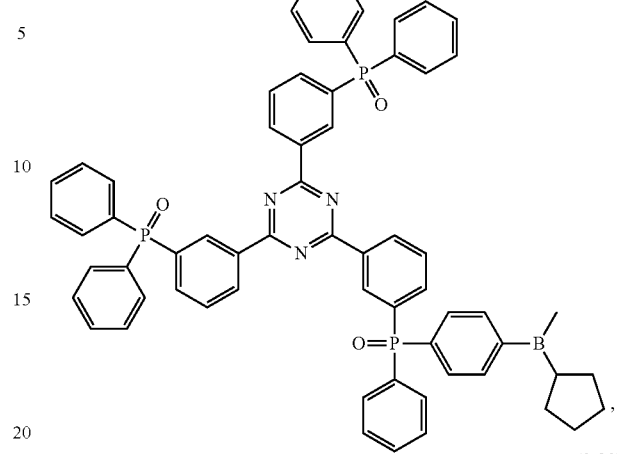
(2-29)
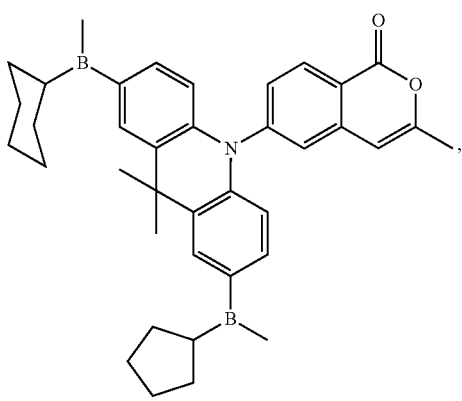
(2-32)
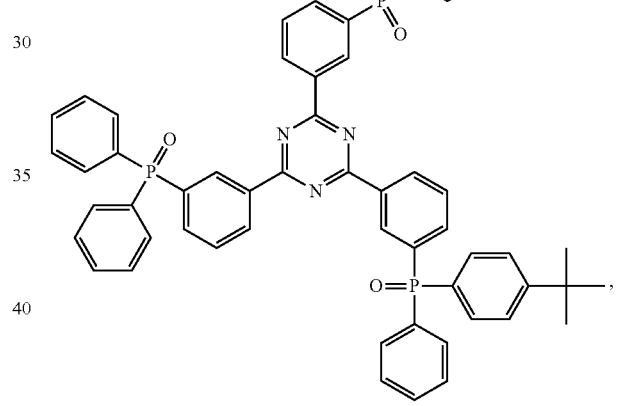
(2-30)
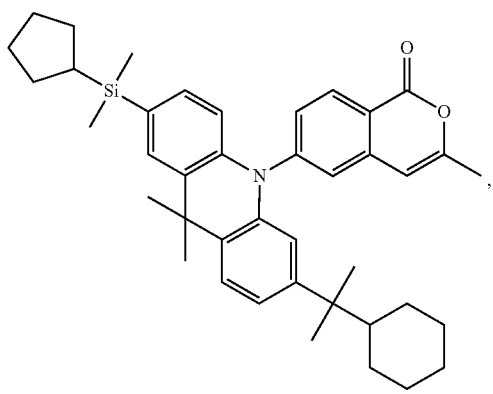
(2-33)
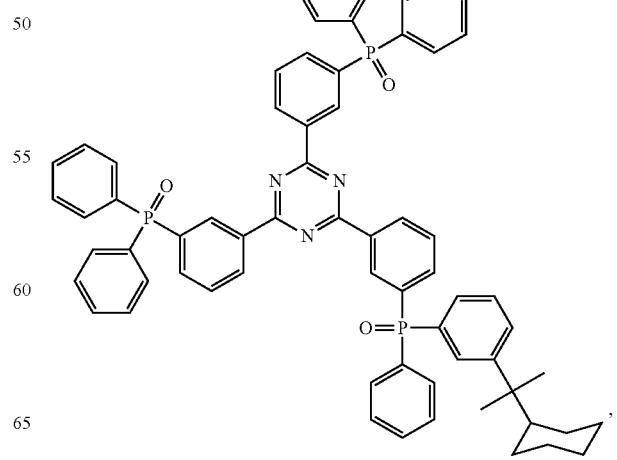

(2-34)
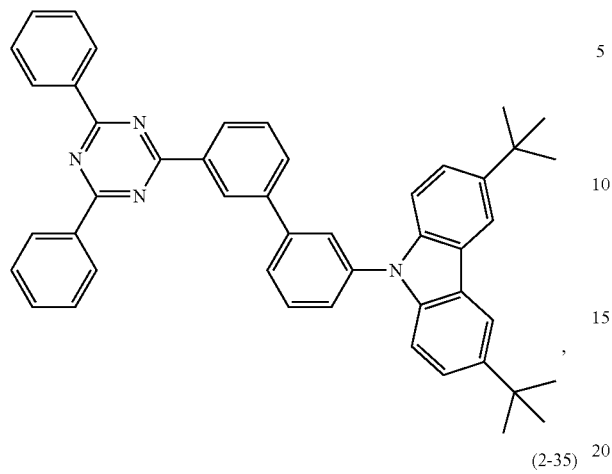
(2-35)
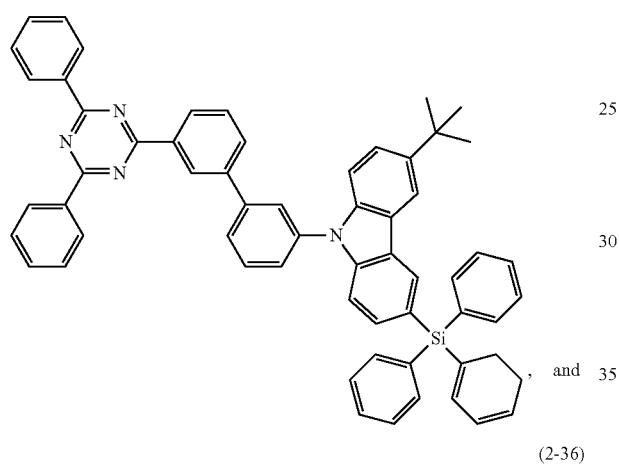
, and
(2-36)
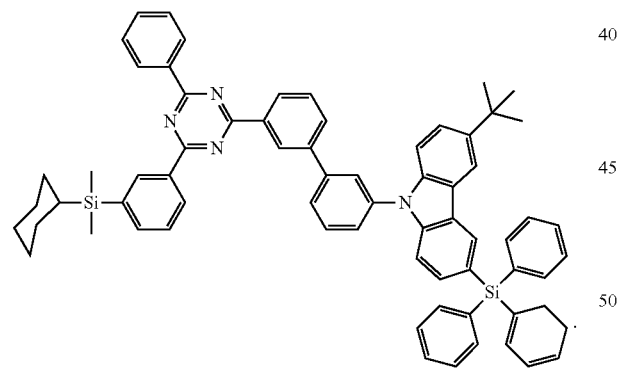
.
Optionally, the steric hindrance groups are groups each independently containing substituted or unsubstituted alkyl, cycloalkyl, aryl, silyl, and borosilicate.
Optionally, the steric hindrance group is selected from one or more of the structures shown below:
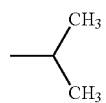 (X-1)
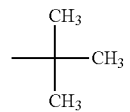 (X-2)
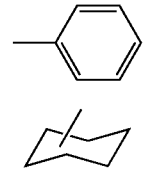 (X-3)
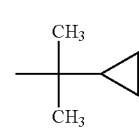 (X-4)
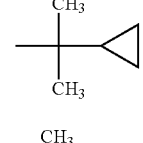 (X-5)
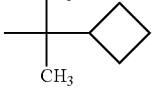 (X-6)
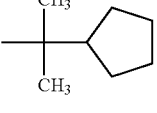 (X-7)
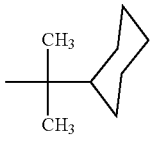 (X-8)
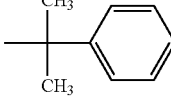 (X-9)
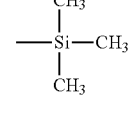 (X-10)
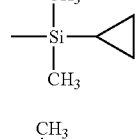 (X-11)
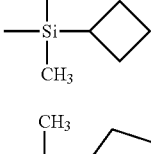 (X-12)
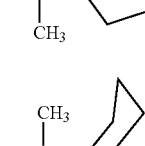 (X-13)
 (X-14)

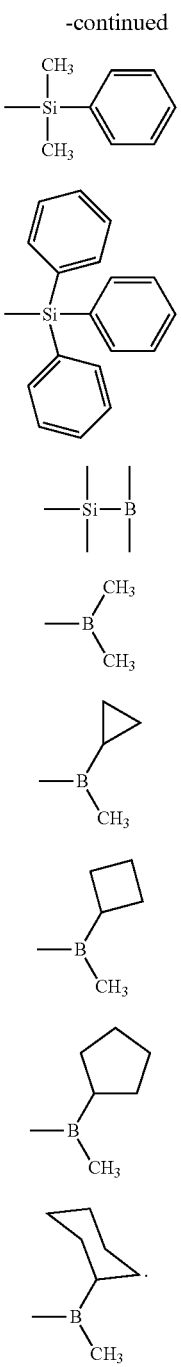

(X-15)
(X-16)
(X-17)
(X-18)
(X-19)
(X-20)
(X-21)
(X-22)

Optionally, the number of steric hindrance groups on the donor molecule structure or the receptor molecule structure is less than or equal to six.

Optionally, the mass ratio of the donor molecule to the receptor molecule in the exciplex is 1:9 to 9:1.

Optionally, the mass ratio of the donor molecular material to the receptor molecular material is 1:2 to 1:5, or the mass ratio of the donor molecular material to the receptor molecular material is 2:1 to 5:1.

Optionally, the guest material is a fluorescent material or a phosphorescent material.

Optionally, the mass ratio of the host material to the guest material is 1000:1 to 2:1.

Optionally, the mass ratio of the host material to the guest material is 200:1 to 5:1.

The technical solution of the present disclosure has the following advantages:

1. The organic electroluminescent device provided by the present disclosure comprises a first electrode, a second electrode, and an organic functional layer located between the first electrode and the second electrode. The organic functional layer comprises a light-emitting layer. The light-emitting layer comprising a host material and an guest material; the host material being an exciplex composed of a donor molecule and a receptor molecule; the donor molecule and/or the receptor molecule containing a steric hindrance group X.

Firstly, by increasing the distance between the donor molecule and the receptor molecule to reduce the overlapping degree between the Highest Occupied Molecular Orbital (HOMO) and Lowest Unoccupied Molecular Orbital (LUMO) of the formed exciplex body, the singlet-triplet energy level gap $\Delta E_{ST}$ is reduced, thereby increasing the RISC rate ($k_{RISC}$) of the exciplex body, and facilitating the RISC of excitons from the triplet state to the singlet state. Eventually, more excitons are converted from the triplet state to the singlet state via RISC, thereby making full use of the triplet energy.

Secondly, if the polarons transfer energy to the triplet state of the exciplex body by means of Dexter energy transfer, the triplet energy of the exciplex body may be increased, which in turn causes molecular bonds of the exciplex body to be broken, resulting in a shortened device lifetime. The introduction of large steric hindrance groups X on the donor molecule and/or the receptor molecule is able to increase the distance between molecules of the exciplex body, reduce the triplet concentration of the host material in the light-emitting layer, and inhibit the Triplet-Triplet Annihilate (TTA) and TPA, thereby enabling to prolong the service life of the electroluminescent device.

Furthermore, the singlet or triplet energy transfer process from the host material to the guest material contains two energy transfer mechanisms, i.e., Förster energy transfer mechanism and Dexter energy transfer mechanism, as shown in FIG. 1. Compared with the short-range Dexter energy transfer mechanism, the long-range Förster energy transfer mechanism has a longer energy transfer distance. Therefore, the introduction of the large steric hindrance groups X on the donor molecule and/or the receptor molecule leads to an increased distance between molecules of the host material and the guest material so as to have the exciplex host material transfer energy to the guest material mainly through the Förster energy transfer mechanism, thereby inhibiting the Dexter energy transfer, avoiding the high doping concentration accompanied with the short-range Dexter energy transfer mode, and also avoiding the problems such as efficiency quenching, roll-off, and high cost of the electroluminescent device due to a high doping concentration.

2. In the organic electroluminescent device provided by the present disclosure, the steric hindrance of the donor molecules and/or the receptor molecules in the light-emitting layer is increased by introducing the large steric hindrance groups X of formula X-1-X-22 to the donor molecules and/or the receptor molecules, so as to increase the distance between the donor molecules and the receptor molecules, reduce the overlapping degree between HOMO and LUMO, increase the RISC rate ($k_{RISC}$) of the exciplex host material, enhance the Förster energy transfer, and improve the device efficiency. Moreover, introducing the large steric hindrance groups of the above X-1-X-22 is able to reduce the triplet concentration of the host material in the light-emitting layer, inhibit the TPA, and prolong the device lifetime.

3. In the organic electroluminescent device provided by the present disclosure, if a large amount of large steric hindrance groups X are introduced, the too high molecular weight will lead to a high evaporation temperature of the donor molecules and/or the receptor molecules, increasing the difficulty of evaporation process. Therefore, in the organic light-emitting layer of the OLED device, X in the molecular structure of the donor molecule or the receptor molecule is hydrogen or a steric hindrance group, and at least one X is a steric hindrance group. At least one of the donor molecule and the receptor molecule contains a steric hindrance group, and the number of steric hindrance groups on a single donor molecule or receptor molecule structure is less than or equal to six, so that the service life of the OLED device is able to be prolonged, and the difficulty of the evaporation process is able to be controlled. When two or more steric hindrance groups are presented in the molecular structure of a donor molecule or a receptor molecule, the structure of each steric hindrance group may be different.

BRIEF DESCRIPTION OF THE DRAWINGS

To illustrate the technical solutions in specific exemplary embodiments of the present disclosure or the prior art more clearly, the drawings used in the description of the specific exemplary embodiments or the prior art are briefly described below. Apparently, the drawings in the following description are only some exemplary embodiments of the present disclosure, and a person of ordinary skilled in the art can obtain other drawings according to these drawings without involving any inventive effort.

DETAILED DESCRIPTION

Figure 1:
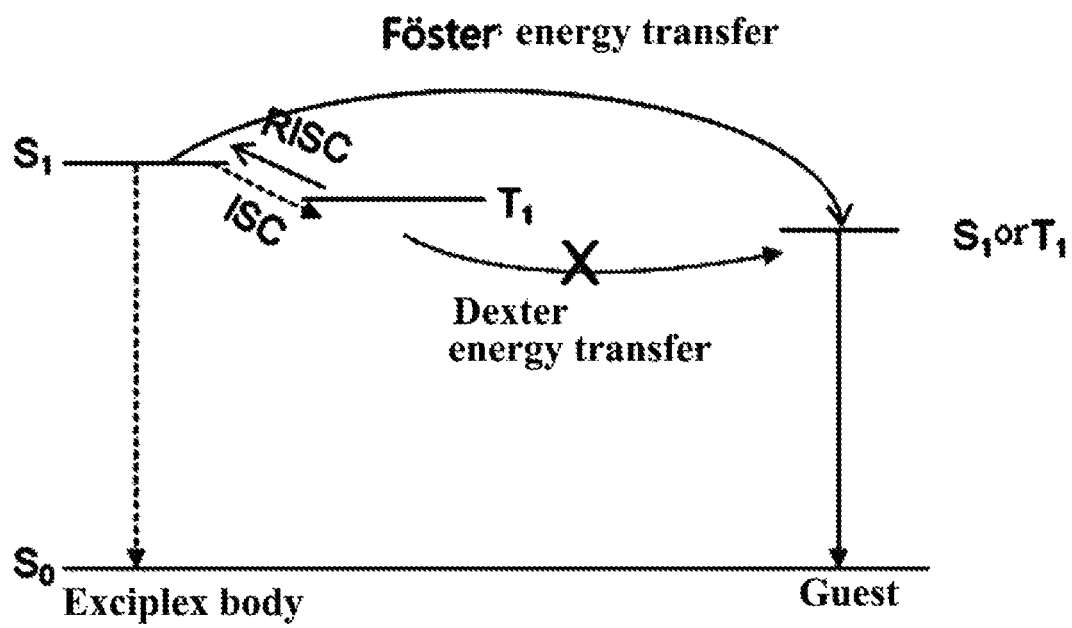
FIG. 1 is a schematic diagram of energy transfer in the luminescence process of an organic electroluminescent device.

In 1987, Deng Qingyun (C. W. Tang) and Vanslyke of the Eastman Kodak Company, U.S.A. first reported a two-layer organic electroluminescent device prepared by using a transparent conductive film as an anode, $Alq_3$ as a light-emitting layer, a triarylamine-based material as a hole transport layer, and an Mg/Ag alloy as a cathode. The conventional fluorescent materials are easy to synthesize and stable and have a long device lifetime. However, due to the electron spin inhibition, at most 25% of singlet excitons can be used for luminescence, and 75% of triplet excitons are wasted. The external quantum efficiency of the device is often less than 5%, which needs to be further improved.

A fluorescent OLED device capable of breaking the limitation of 25% of the internal quantum efficiency limitation mainly employs a Thermally Activated Delayed Fluorescence (TADF) mechanism. The TADF mechanism utilizes an organic small molecular material having a small singlet-triplet energy level gap ($\Delta E_{ST}$). The triplet excitons of the organic small molecular material having a small singlet-triplet energy level gap can be converted to singlet excitons by the process of Reverse Intersystem Crossing (RISC) under the absorption of ambient heat, which allows to reach 100% of the internal quantum efficiency of the device in theory. However, the currently reported TADF material has a large efficiency roll-off and a short service life under high brightness, which limits its application in panchromatic display and white-light illumination.

The present disclosure provides an organic electroluminescent device comprising an organic functional layer, the organic functional layer comprising a light-emitting layer, the light-emitting layer comprising a host material and a guest material; the host material being an exciplex composed of a donor molecule and a receptor molecule, the donor molecule and/or the receptor molecule containing a plurality of steric hindrance groups, so as to solve the problems of the large singlet-triplet energy level gap ($\Delta EST$) of an exciplex TADF host material, the low RISC rate $k_{RISC}$, and the severe Triplet-Polaron Annihilate (TPA) in the light-emitting layer, thereby improving the device efficiency and the service life of the organic electroluminescent device.

The technical solutions of the present disclosure are clearly and completely described below with reference to the accompanying drawings. It is obvious that the described Exemplary embodiments are a part of the embodiments of the present disclosure, and not all of the embodiments. All other embodiments obtained by a person of ordinary skill in the art based on the Exemplary embodiments of the present disclosure without involving an inventive effort are within the protection scope of the present disclosure.

In the description of the present disclosure, it is to be noted that the terms "first", "second", and "third" are only for descriptive purpose, and cannot be construed as indicating or implying relative importance.

The present disclosure can be implemented in different forms, and should not be construed as being limited to the Exemplary embodiments set forth herein. In contrast, these Exemplary embodiments are provided such that the present disclosure will be thorough and complete, and the concept of the present disclosure is thoroughly presented to those skilled in the art. The present disclosure is defined only by the appended claims. In the accompanying drawings, the dimensions and the relative dimensions of layers and regions are exaggerated for clarity.

Exemplary Embodiment 1

Figure 2:
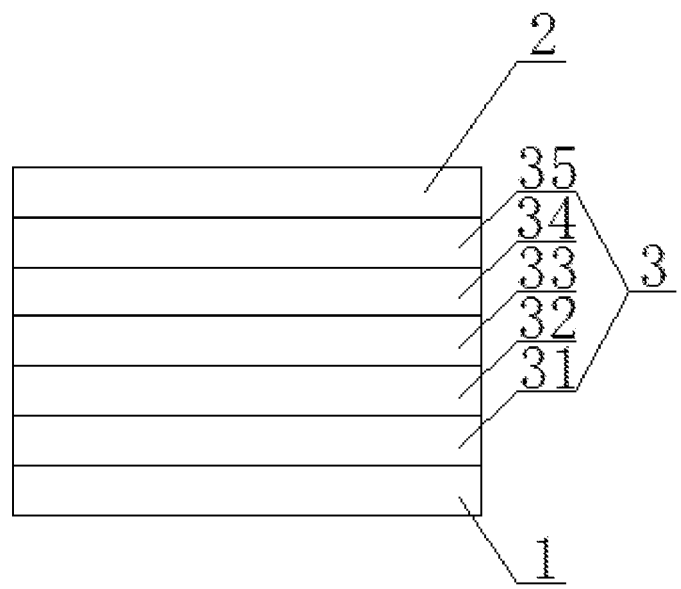
FIG. 2 is a schematic structural diagram of an organic electroluminescent device according to Exemplary embodiment 1 of the present disclosure.

This Exemplary embodiment provides an organic electroluminescent device, having a first electrode 1, a second electrode 2, and an organic functional layer 3 located between the first electrode 1 and the second electrode 2, as shown in FIG. 2. The first electrode 1 is an anode, the second electrode 2 is a cathode, and the organic functional layer 3 includes a hole injection layer 31, a hole transport layer 32, a light-emitting layer 33, an electron transport layer 34, and an electron injection layer 35 which are arranged in a stacked manner. That is, the structure of the organic electroluminescent device is: anode/hole injection layer/hole transport layer/light-emitting layer/electron transport layer/electron injection layer/cathode.

The light-emitting layer 33 is composed of a host material and a guest material doped in the host material. The guest material may be a fluorescent material or a phosphorescent material. The exciplex is used as the host material, and the mass ratio of the host material to the guest material is 1000:1 to 2:1, preferably 200:1 to 5:1. The exciplex is composed of a donor molecule and a receptor molecule. The donor molecule is a compound with the hole transport property containing at least one of carbazolyl, triphenylaminyl, and aryl. The receptor molecule is a compound with the electron transport property containing at least one of pyrimidinyl, triazinyl, oxadiazolyl, pyridyl, carbazolyl, aryl, cyano, acridinyl, dibenzothiophenyl, triphenylphosphonyl, and triphenylboryl. At least one of the donor molecule or the receptor molecule contains a steric hindrance group X for increasing the distance between the donor molecule and the receptor molecule, and the steric hindrance groups X each independently containing substituted or unsubstituted alkyl, cycloalkyl, aryl, silyl, and borosilicate.

In this Exemplary embodiment, a compound composed of triphenylaminyl and carbazolyl is selected as the donor molecule, and the selected substituent group X is

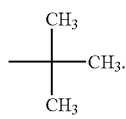

The compound has the structure as shown in formula (1-1):

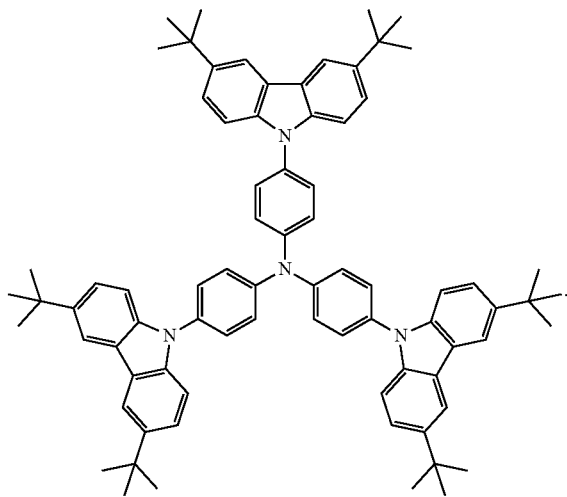

(1-1)

A compound composed of carbazolyl and triazinyl is selected as the receptor molecule, and the selected substituent group X is

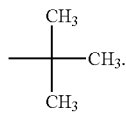

The compound has the structure as shown in formula (2-34):

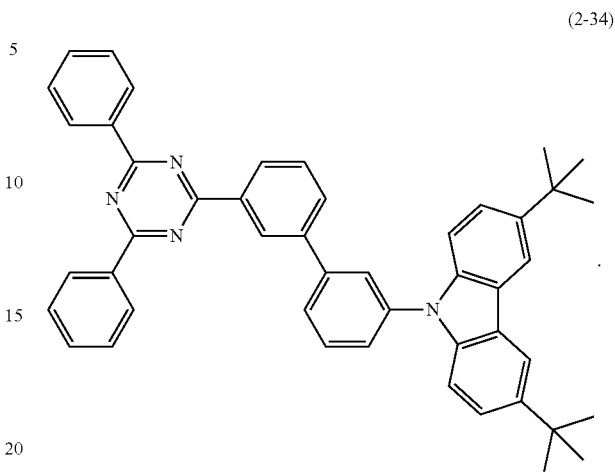

(2-34)

In the organic electroluminescent device of this Exemplary embodiment, the first electrode 1 is made of ITO material, The hole injection layer 31 is made of 2,3,6,7,10,11-hexacyano-1,4,5,8,9,12-hexaazatriphenylene (HATCN for short). The hole transport layer 32 is made of a hole transport material N,N'-diphenyl-N,N'-bis(1-naphthyl)-1,1'-biphenyl-4,4'-diamine (NPB for short). The electron transport layer 34 is made of an electron transport material 1,3,5-tris(1-phenyl-1H-benzimidazol-2-yl)benzene (TPBi for short). The electron injection layer 35 is made of an electron injection material LiF. The second electrode 2 is made of Al. The electron injection layer 35 and the second electrode 2 form an electron injection layer/metal layer structure.

The light-emitting layer 33 is designed such that a donor molecule as shown in formula (1-1) and a receptor molecule as shown in formula (2-34) form an exciplex body. In the exciplex, the mass ratio of the donor molecule as shown in formula (1-1) to the receptor molecule as shown in formula (2-34) is 2:8. A yellow fluorescent dye PPTPAD is selected as the guest material, and the doped yellow fluorescent material PPTPAD accounts for 1% of the mass of the light-emitting layer material to have the organic electroluminescent device form the following specific structure:

ITO/HATCN (5 nm)/NPB (40 nm)/molecule (1-1) (19.8 wt %):molecule (2-34) (79.2 wt %):PPTPAD (1 wt %) (20 nm)/TPBi (40 nm)/LiF (0.5 nm)/Al (150 nm).

Figure 3:
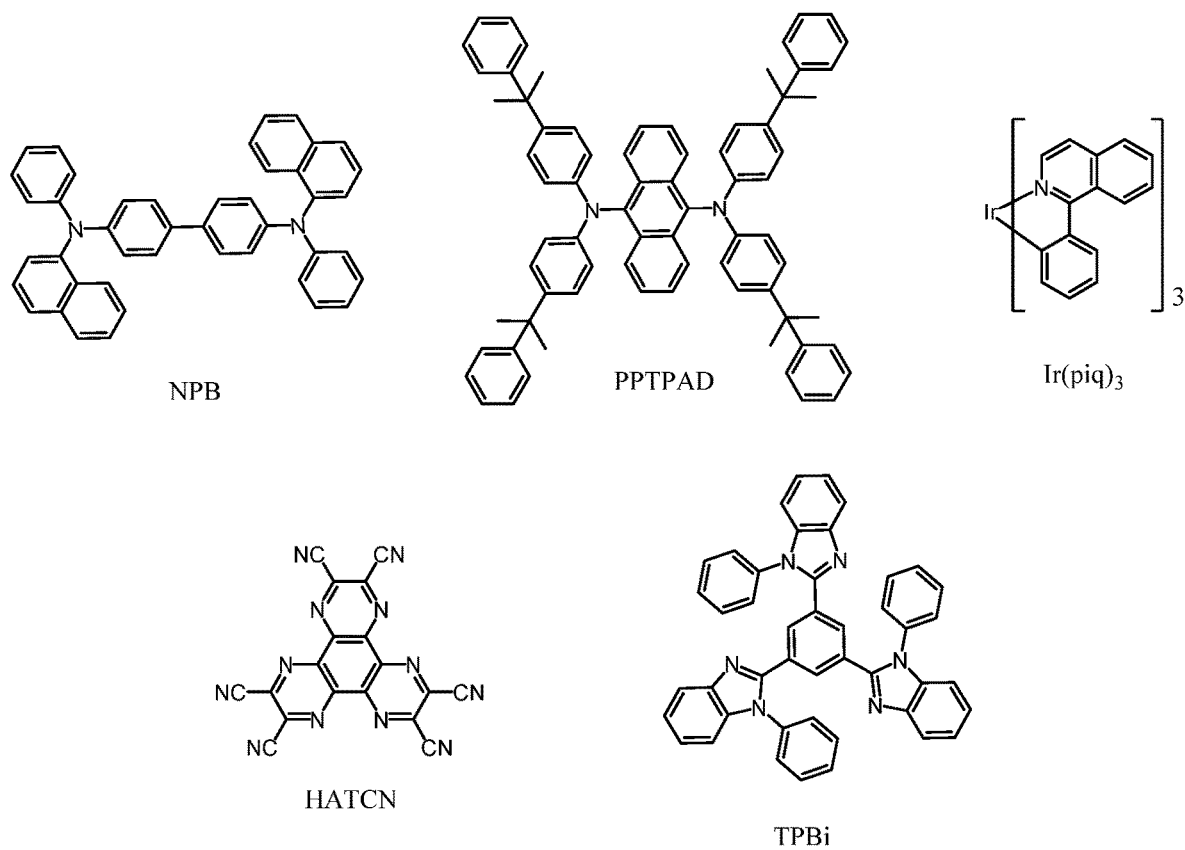
FIG. 3 shows molecular structures of materials used in the electroluminescent device of Exemplary embodiments 1-4 and Comparative Exemplary embodiments 1 and 2 of the present disclosure.

The layer thickness is presented in parentheses, and the molecular formulas of molecule HATCN, molecule NPB, molecule PPTPAD, and molecule TPBi are as shown in FIG. 3.

As an alternative exemplary embodiment, the mass ratio of the donor molecule as shown in formula (1-1) to the receptor molecule as shown in formula (2-34) may also be selected to be other values in the range of 1:2-1:5, other values in the range of 2:1-5:1, or other values in the range of 1:9-9:1, which are all able to achieve the object of the present disclosure and fall within the protection scope of the present disclosure.

As an alternative exemplary embodiment, the mass fraction of the doped yellow fluorescent material PPTPAD in the light-emitting layer material may also be selected to be other values in the range of 200:1-5:1 or other values in the range of 1000:1-2:1, which are all able to achieve the object of the present disclosure and fall within the protection scope of the present disclosure.

As an alternative exemplary embodiment, the donor molecule and the receptor molecule forming the exciplex are not limited to the molecular structure as shown in formula (1-1) and the molecular structure as shown in formula (2-34):

An exciplex is able to be formed by any one of the above provided donor molecule structures substituted by any one of the above steric hindrance groups X and any one of the above provided receptor molecules which are not substituted by the steric hindrance group X;

An exciplex is able to be formed by any one of the above provided donor molecules which are not substituted by the steric hindrance group X and any one of the above provided receptor molecule structures substituted by any one of the above steric hindrance groups X; and An exciplex is able to be formed by any one of the above provided donor molecule structures substituted by any one of the above steric hindrance groups X and any one of the above provided receptor molecule structures substituted by any one of the above steric hindrance groups X.

Exemplary Embodiment 2

In Exemplary embodiment 2, the OLED device may be designed as an organic electroluminescent device, including an anode, a hole injection layer, a hole transport layer, an organic light-emitting layer, an electron transport layer, an electron injection layer, and a cathode. In this Exemplary embodiment, a compound composed of triphenylaminyl and carbazolyl is selected as the donor molecule, and the selected substituent group X is

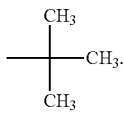

The compound has the structure as shown in formula (1-1):

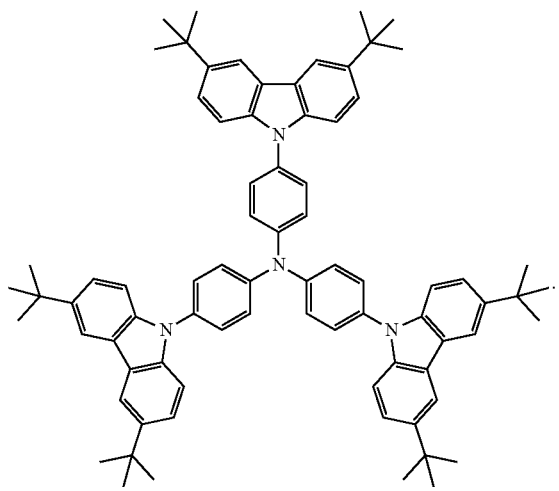

(1-1)

A compound composed of carbazolyl and triazinyl is selected as the receptor molecule and has a structure of formula (A), which differs from the molecule (2-34) used in the Exemplary embodiment 1 in that there is no large steric hindrance substituent group, i.e., tert-butyl. The molecular structure of formula (A) is as follows:

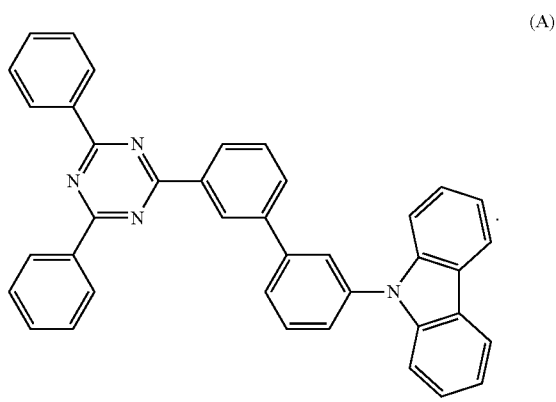 [SMILES: c1ccc(-c2nc(-c3ccccc3)nc(-c3cccc(-c4cccc(-n5c6ccccc6c6ccccc65)c4)c3)n2)cc1]

(A)

The donor molecule as shown in formula (1-1) and the receptor molecule as shown in formula (A) form an exciplex. In the exciplex, the mass ratio of the donor molecule as shown in formula (1-1) to the receptor molecule as shown in formula (A) is 2:8.

Exemplary embodiment 2 differs from Exemplary embodiment 1 only in the aspect of organic light-emitting layer, i.e. the receptor molecule thereof does not contain a large steric hindrance group, and is designed as follows:

ITO/HATCN (5 nm)/NPB (40 nm)/molecule (1-1) (19.8 wt %):molecule (A) (79.2 wt %):PPTPAD (1 wt %) (20 nm)/TPBi (40 nm)/LiF (0.5 nm)/Al (150 nm). The fluorescent dye PPTPAD is selected as the doping material, where the doped yellow fluorescent material PPTPAD accounts for 1% of the mass of the light-emitting layer material.

Comparative Exemplary Embodiment 1

In Comparative Exemplary embodiment 1, the OLED device may be designed as an organic electroluminescent device, including an anode, a hole injection layer, a hole transport layer, an organic light-emitting layer, an electron transport layer, an electron injection layer, and a cathode. In this comparative Exemplary embodiment, a compound composed of triphenylaminyl and carbazolyl is selected as the donor molecule, and has a structure of formula (B), which differs from the donor molecule (1-1) used in Exemplary embodiment 1 in that there is no large steric hindrance substituent group, i.e., tert-butyl. The molecular structure of formula (B) is as follows:

(B)

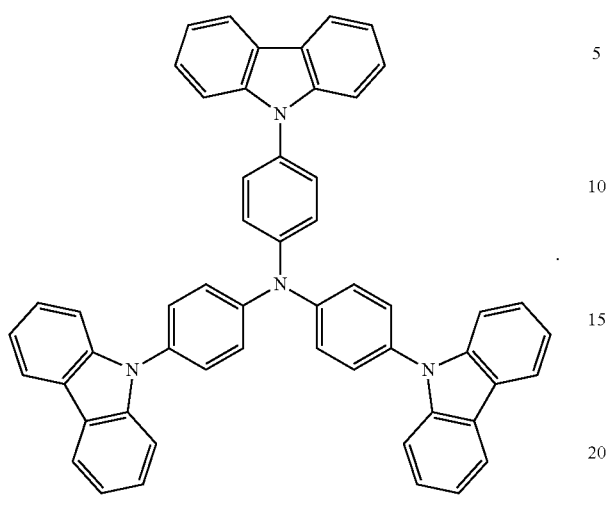

A compound composed of carbazolyl and triazinyl is selected as the receptor molecule and has a structure of formula (A), which differs from the molecule (2-34) used in Exemplary embodiment 1 in that there is no large steric hindrance substituent group, i.e., tert-butyl.

(A)

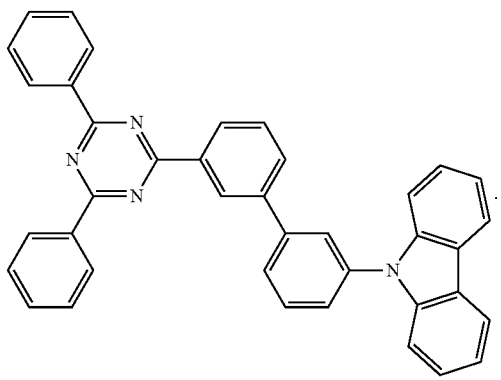

The donor molecule as shown in formula (B) and the receptor molecule as shown in formula (A) form an exciplex. In the exciplex, the mass ratio of the donor molecule as shown in formula (B) to the receptor molecule as shown in formula (A) is 2:8.

Comparative Exemplary embodiment 1 differs from Exemplary embodiments 1 and 2 only in the aspect of organic light-emitting layer, i.e. in Comparative Exemplary embodiment 1, the donor molecule and the receptor molecule do not contain a large steric hindrance group, and is designed as follows:

ITO/HATCN (5 nm)/NPB (40 nm)/molecule (B) (19.8 wt %):molecule (A) (79.2 wt %):PPTPAD (1 wt %) (20 nm)/TPBi (40 nm)/LiF (0.5 nm)/Al (150 nm). The fluorescent dye PPTPAD is selected as the doping material, where the doped yellow fluorescent material PPTPAD accounts for 1% of the mass of the light-emitting layer material.

Exemplary Embodiment 3

In Exemplary embodiment 3, the OLED device may be designed as an organic electroluminescent device, including an anode, a hole injection layer, a hole transport layer, an organic light-emitting layer, an electron transport layer, an electron injection layer, and a cathode. In this Exemplary embodiment, a compound composed of triphenylaminyl and carbazolyl is selected as the donor molecule, and the selected substituent group X is

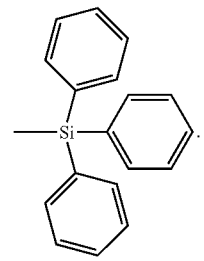 [SMILES: C[Si](c1ccccc1)(c1ccccc1)c1ccccc1]

The compound has the structure as shown in formula (1-10):

(1-10)

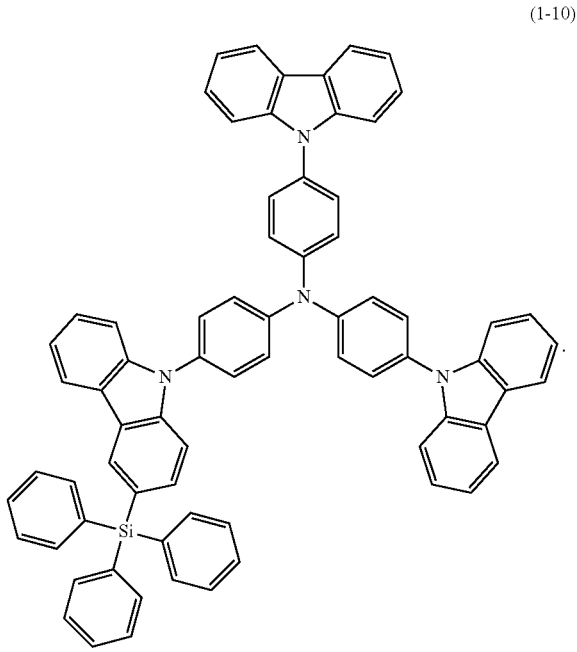 [SMILES: c1ccc([Si](c2ccccc2)(c2ccccc2)c2ccc3c(c2)c2ccccc2n3-c2ccc(N(c3ccc(-n4c5ccccc5c5ccccc54)cc3)c3ccc(-n4c5ccccc5c5ccccc54)cc3)cc2)cc1]

A compound composed of carbazolyl and triazinyl is selected as the receptor molecule, and the selected substituent group X is

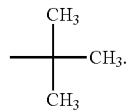

The compound has the structure as shown in formula (2-19):

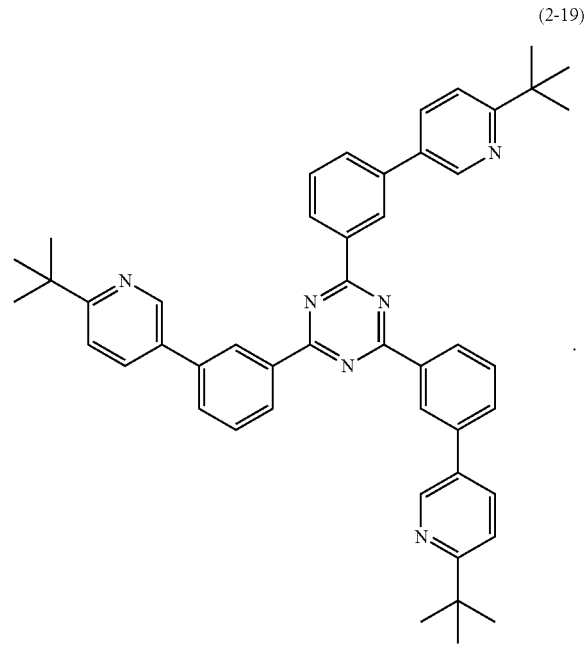 [SMILES: CC(C)(C)c1ccc(-c2cccc(-c3nc(-c4cccc(-c5ccc(C(C)(C)C)nc5)c4)nc(-c4cccc(-c5ccc(C(C)(C)C)nc5)c4)n3)c2)cn1]

(2-19)

In Exemplary embodiment 3, the first electrode, i.e., the anode, of the organic electroluminescent device is made of ITO material. The hole injection layer is made of 2,3,6,7,10,11-hexacyano-1,4,5,8,9,12-hexaazatriphenylene (HATCN for short). The hole transport layer is made of a hole transport material N,N'-diphenyl-N,N'-bis(1-naphthyl)-1,1'-biphenyl-4,4'-diamine (NPB for short). The electron transport layer is made of an electron transport material 1,3,5-tris(1-phenyl-1H-benzimidazol-2-yl)benzene (TPBi for short). An electron injection material LiF and a cathode material Al are selected to form an electron injection layer/metal layer structure.

The light-emitting layer 33 is designed such that a donor molecule as shown in formula (1-10) and a receptor molecule as shown in formula (2-19) form an exciplex. In the exciplex, the mass ratio of the donor molecule as shown in formula (1-10) to the receptor molecule as shown in formula (2-19) is 1:1. A red phosphorescent dye Ir(piq)$_3$ is selected as the doping material, and the doped red phosphorescent material Ir(piq)$_3$ accounts for 1% of the mass of the light-emitting layer material to have the organic electroluminescent device form the following specific structure:

ITO/HATCN (5 nm)/NPB (40 nm)/molecule (1-10) (49.5 wt %):molecule (2-19) (49.5 wt %):1 wt % Ir(piq)$_3$ (20 nm)/TPBi (40 nm)/LiF (0.5 nm)/Al (150 nm). The molecular structure of the red phosphorescent material Ir(piq)$_3$ is as shown in FIG. 3.

Exemplary Embodiment 4

In Exemplary embodiment 4, the OLED device may be designed as an organic electroluminescent device, including an anode, a hole injection layer, a hole transport layer, an organic light-emitting layer, an electron transport layer, an electron injection layer, and a cathode. In this Exemplary embodiment, a compound composed of triphenylaminyl and carbazolyl is selected as the donor molecule, and the selected substituent group X is

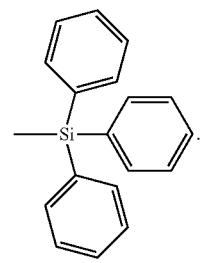 [SMILES: C[Si](c1ccccc1)(c1ccccc1)c1ccccc1]

The compound has the structure as shown in formula (1-10):

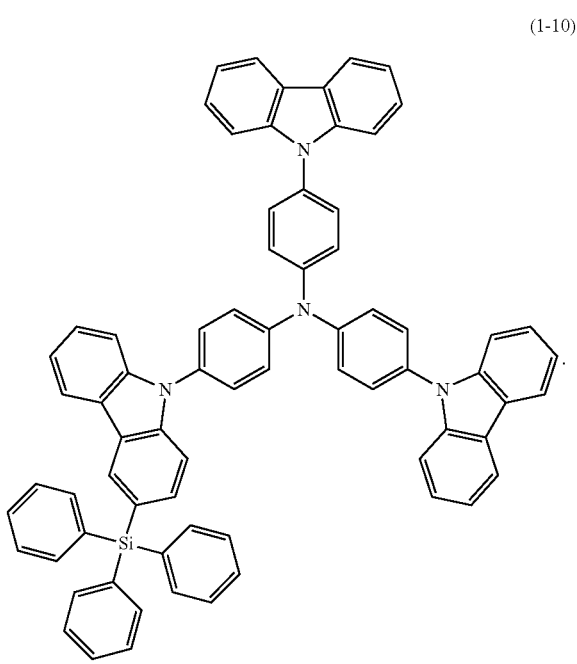 [SMILES: c1ccc([Si](c2ccccc2)(c2ccccc2)c2ccc3c(c2)c2ccccc2n3-c2ccc(N(c3ccc(-n4c5ccccc5c5ccccc54)cc3)c3ccc(-n4c5ccccc5c5ccccc54)cc3)cc2)cc1]

(1-10)

A compound composed of carbazolyl and triazinyl is selected as the receptor molecule, and has a structure of formula (C), which differs from the receptor molecule (2-19) used in Exemplary embodiment 3 in that there is no large steric hindrance substituent group, i.e., tert-butyl. The molecular structure of formula (C) is as follows:

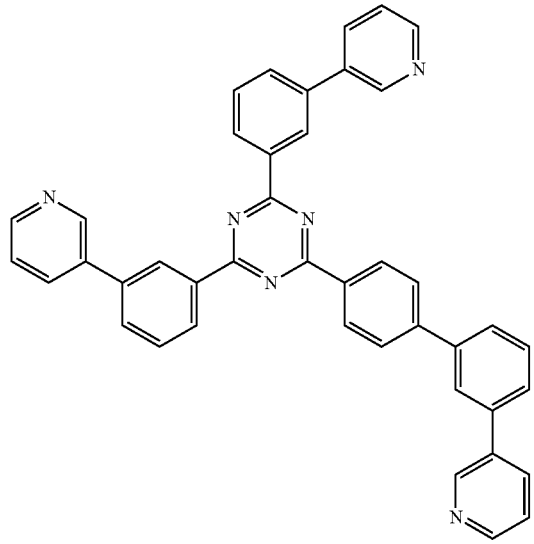

(C)

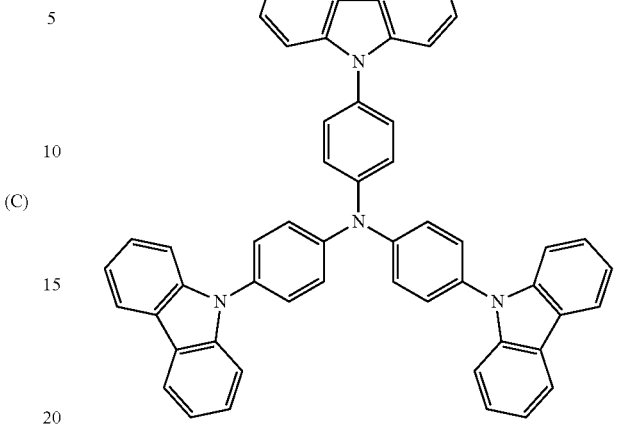

(B)

A compound composed of carbazolyl and triazinyl is selected as the receptor molecule, and has a structure of formula (C), which differs from the receptor molecule (2-19) in Exemplary embodiment 3 in that there is no large steric hindrance substituent group, i.e., tert-butyl.

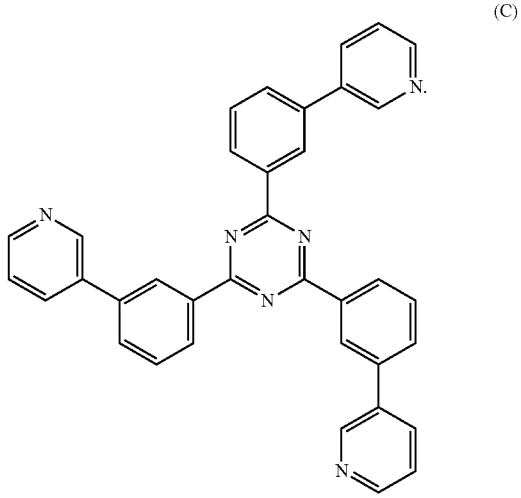 [SMILES: c1cncc(-c2cccc(-c3nc(-c4cccc(-c5cccnc5)c4)nc(-c4cccc(-c5cccnc5)c4)n3)c2)c1]

(C)

An exciplex is formed by the donor molecule as shown in formula (1-10) and the receptor molecule as shown in formula (C). In the exciplex, the mass ratio of the donor molecule as shown in formula (1-10) to the receptor molecule as shown in formula (C) is 1:1.

Exemplary embodiment 4 differs from Exemplary embodiment 3 only in the aspect of organic light-emitting layer, i.e. the receptor molecule thereof does not contain a large steric hindrance group, and is designed as follows:

ITO/HATCN (5 nm)/NPB (40 nm)/molecule (1-10) (49.5 wt %):molecule (C) (49.5 wt %):1 wt % Ir(piq)$_3$ (20 nm)/ TPBi (40 nm)/LiF (0.5 nm)/Al (150 nm). A red phosphorescent dye Ir(piq)$_3$ is selected as the doping material, where the doped red phosphorescent material Ir(piq)$_3$ accounts for 1% of the mass of the light-emitting layer material.

Comparative Exemplary Embodiment 2

In Comparative Exemplary embodiment 2, the OLED device may be designed as an organic electroluminescent device, including an anode, a hole injection layer, a hole transport layer, an organic light-emitting layer, an electron transport layer, an electron injection layer, and a cathode. In this Exemplary embodiment, a compound composed of triphenylaminyl and carbazolyl is selected as the donor molecule, and has a structure as shown in formula (B):

The donor molecule as shown in formula (B) and the receptor molecule as shown in formula (C) form an exciplex. In the exciplex, the mass ratio of the donor molecule as shown in formula (B) to the receptor molecule as shown in formula (C) is 1:1.

Comparative Exemplary embodiment 2 differs from Exemplary embodiments 3 and 4 only in the aspect of organic light-emitting layer, i.e. in Comparative Exemplary embodiment 2, the donor molecule and the receptor molecule do not contain a large steric hindrance group, and is designed as follows:

ITO/HATCN (5 nm)/NPB (40 nm)/molecule (B) (49.5 wt %):molecule (C) (49.5 wt %):1 wt % Ir(piq)$_3$ (20 nm)/TPBi (40 nm)/LiF (0.5 nm)/Al (150 nm). A red phosphorescent dye Ir(piq)$_3$ is selected as the doping material, where the doped red phosphorescent material Ir(piq)$_3$ accounts for 1% of the mass of the light-emitting layer material.

Exemplary Embodiment 5

This Exemplary embodiment differs from Exemplary embodiment 1 in that the donor molecule has a structure as shown in formula (1-7), the mass ratio of the donor molecule material to the receptor molecule material is 1:9, and the mass ratio of the host material to the guest material is 200:1. The device has an external quantum efficiency of 12.6% and a CIE color coordinate (0.32, 0.59) at a brightness of 5000 cd/m$^2$.

Exemplary Embodiment 6

This Exemplary embodiment differs from Exemplary embodiment 1 in that the donor molecule has a structure as shown in formula (1-10), the mass ratio of the donor molecule material to the receptor molecule material is 1:2, and the mass ratio of the host material to the guest material is 200:1. The resulting device has an external quantum efficiency of 14.1% and a CIE color coordinate (0.32, 0.59) at a brightness of 5000 cd/m$^2$.

Exemplary Embodiment 7

This Exemplary embodiment differs from Exemplary embodiment 1 in that the donor molecule has a structure as shown in formula (1-13), the mass ratio of the donor molecule material to the receptor molecule material is 1:1, and the mass ratio of the host material to the guest material is 5:1. The resulting device has an external quantum efficiency of 12.4% and a CIE color coordinate (0.32, 0.59) at a brightness of 5000 cd/m$^2$.

Exemplary Embodiment 8

This Exemplary embodiment differs from Exemplary embodiment 1 in that the donor molecule has a structure as shown in formula (1-16), the mass ratio of the donor molecule to the receptor molecule is 2:3, and the mass ratio of the host material to the guest material is 2:1. The resulting device has an external quantum efficiency of 13.6% and a CIE color coordinate (0.32, 0.59) at a brightness of 5000 cd/m$^2$.

Exemplary Embodiment 9

This Exemplary embodiment differs from Exemplary embodiment 2 in that the donor molecule has a structure as shown in formula (1-18), the mass ratio of the donor molecule to the receptor molecule is 1:3, and the mass ratio of the host material to the guest material is 100:1. The resulting device has an external quantum efficiency of 14.6% and a CIE color coordinate (0.32, 0.59) at a brightness of 5000 cd/m$^2$.

Exemplary Embodiment 10

This Exemplary embodiment differs from Exemplary embodiment 2 in that the donor molecule has a structure as shown in formula (1-25), the mass ratio of the donor molecule to the receptor molecule is 1:4, and the mass ratio of the host material to the guest material is 150:1. The device has an external quantum efficiency of 15.1% and a CIE color coordinate (0.33, 0.59) at a brightness of 5000 cd/m$^2$.

Exemplary Embodiment 11

This Exemplary embodiment differs from Exemplary embodiment 2 in that the donor molecule has a structure as shown in formula (1-26), the mass ratio of the donor molecule to the receptor molecule is 1:4, and the mass ratio of the host material to the guest material is 150:1. The resulting device has an external quantum efficiency of 13.8% and a CIE color coordinate (0.33, 0.59) at a brightness of 5000 cd/m$^2$.

Exemplary Embodiment 12

This Exemplary embodiment differs from Exemplary embodiment 3 in that the receptor molecule has a structure as shown in formula (2-5), the mass ratio of the donor molecule to the receptor molecule is 2:1, and the mass ratio of the host material to the guest material is 500:1. The resulting device has an external quantum efficiency of 14.2% and a CIE color coordinate (0.67, 0.33) at a brightness of 5000 cd/m$^2$.

Exemplary Embodiment 13

This Exemplary embodiment differs from Exemplary embodiment 3 in that the receptor molecule has a structure as shown in formula (2-16), the mass ratio of the donor molecule to the receptor molecule is 1:1, and the mass ratio of the host material to the guest material is 150:1. The device has an external quantum efficiency of 17.1% and a CIE color coordinate (0.67, 0.33) at a brightness of 5000 cd/m$^2$.

Exemplary Embodiment 14

This Exemplary embodiment differs from Exemplary embodiment 4 in that the receptor molecule has a structure as shown in formula (2-17), the mass ratio of the donor molecule to the receptor molecule is 1:1, and the mass ratio of the host material to the guest material is 150:1. The device has an external quantum efficiency of 17.7% and a CIE color coordinate (0.67, 0.33) at a brightness of 5000 cd/m$^2$.

Exemplary Embodiment 15

This Exemplary embodiment differs from Exemplary embodiment 1 in that the receptor molecule has a structure as shown in formula (2-20), the mass ratio of the donor molecule to the receptor molecule is 6:4, and the mass ratio of the host material to the guest material is 90:1. The device has an external quantum efficiency of 13.9% and a CIE color coordinate (0.33, 0.59) at a brightness of 5000 cd/m$^2$.

Exemplary Embodiment 16

This Exemplary embodiment differs from Exemplary embodiment 1 in that the receptor molecule has a structure as shown in formula (2-25), the mass ratio of the donor molecule to the receptor molecule is 3:7, and the mass ratio of the host material to the guest material is 60:1. The device has an external quantum efficiency of 14.8% and a CIE color coordinate (0.33, 0.59) at a brightness of 5000 cd/m$^2$.

Exemplary Embodiment 17

This Exemplary embodiment differs from Exemplary embodiment 2 in that the receptor molecule has a structure as shown in formula (2-26), the mass ratio of the donor molecule to the receptor molecule is 4:6, and the mass ratio of the host material to the guest material is 40:1. The device has an external quantum efficiency of 15.8% and a CIE color coordinate (0.33, 0.59) at a brightness of 5000 cd/m².

Exemplary Embodiment 18

This Exemplary embodiment differs from Exemplary embodiment 3 in that the receptor molecule has a structure as shown in formula (2-31), the mass ratio of the donor molecule to the receptor molecule is 1:8, and the mass ratio of the host material to the guest material is 100:1. The device has an external quantum efficiency of 18.1% and a CIE color coordinate (0.67, 0.33) at a brightness of 5000 cd/m².

Exemplary Embodiment 19

This Exemplary embodiment differs from Exemplary embodiment 3 in that the receptor molecule has a structure as shown in formula (2-32), the mass ratio of the donor molecule to the receptor molecule is 1:7, and the mass ratio of the host material to the guest material is 180:1. The device has an external quantum efficiency of 17.9% and a CIE color coordinate (0.67, 0.33) at a brightness of 5000 cd/m².

Exemplary Embodiment 20

This Exemplary embodiment differs from Exemplary embodiment 4 in that the receptor molecule has a structure as shown in formula (2-35), the mass ratio of the donor molecule to the receptor molecule is 1:6, and the mass ratio of the host material to the guest material is 80:1. The device has an external quantum efficiency of 16.9% and a CIE color coordinate (0.67, 0.33) at a brightness of 5000 cd/m².

Exemplary Embodiment 21

This Exemplary embodiment differs from Exemplary embodiment 4 in that the receptor molecule has a structure as shown in formula (2-36), the mass ratio of the donor molecule to the receptor molecule is 1:1, and the mass ratio of the host material to the guest material is 60:1. The device has an external quantum efficiency of 18.0% and a CIE color coordinate (0.67, 0.33) at a brightness of 5000 cd/m².

In the foregoing Exemplary embodiments, the selectable structural formulas and the substitutable positions of the steric hindrance group X of the donor molecule are as shown in any one of formulas (D-1) to (D-9). The selectable structural formulas and the substitutable positions of the steric hindrance group X of the receptor molecule are as shown in any one of formulas (A-1) to (A-12). In the foregoing Exemplary embodiments, X in the molecular structure of the donor molecule or the receptor molecule is hydrogen or a steric hindrance group, and at least one X is a steric hindrance group. At least one of the donor molecule and the receptor molecule contains a steric hindrance group, and the number of steric hindrance groups on a single donor molecule or receptor molecule structure is less than or equal to six. When two or more steric hindrance groups are present on the molecular structure of the donor molecule or the receptor molecule, the structure of each steric hindrance group may be different. In the foregoing Exemplary embodiments, the steric hindrance group X may be selected from one or more of the structures shown in formulas (X-1) to (X-22).

In the foregoing Exemplary embodiments, the structure of the donor molecule may be any one of the structures shown in formulas (1-1) to (1-27).

In the foregoing Exemplary embodiments, the structure of the receptor molecule may be any one of the structures shown in formulas (2-1) to (2-36).

In the foregoing Exemplary embodiments, the mass ratio of the donor molecule to the receptor molecule in the exciplex is 1:9 to 9:1. Preferably, the mass ratio of the donor molecular material to the receptor molecular material is 1:2 to 1:5, or, the mass ratio of the donor molecular material to the receptor molecular material is 2:1 to 5:1.

Test Exemplary Embodiment 1

The characteristics of current, voltage, brightness, and luminescence spectrum of the devices of Exemplary embodiments 1-4 and Comparative Exemplary embodiments 1 and 2 are synchronously tested by a PR 650 spectral scanning brightness meter and a Keithley K 2400 digital source meter system.

I. The performances of the OLED devices of Exemplary embodiment 1, Exemplary embodiment 2, and Comparative Exemplary embodiment 1 are tested. The test results are shown in Table 1 below:

TABLE 1

Performance test of the OLED devices

| | Brightness (cd/m²) | External quantum efficiency | Power efficiency (lm/W) | Device lifetime LT90 | CIE color coordinate |
|---|---|---|---|---|---|
| Exemplary embodiment 1 | 5000 | 16.6% | 26.6 | 1.4 | (0.32, 0.59) |
| Exemplary embodiment 2 | 5000 | 16.1% | 25.8 | 1.3 | (0.32, 0.59) |
| Comparative Exemplary embodiment 1 | 5000 | 11.8% | 16.1 | 1 | (0.33, 0.59) |

As can be seen from Table 1, in the OLED devices prepared through the materials provided in Exemplary embodiment 1, Exemplary embodiment 2, and Comparative Exemplary embodiment 1, the guest materials are 1% doped fluorescent material PPTPAD. The external quantum efficiency and the power efficiency of the OLED devices of Exemplary embodiment 1 and Exemplary embodiment 2 are higher than those of the OLED device of Comparative Exemplary embodiment 1 at the same brightness. The external quantum efficiency and the power efficiency of the OLED device of Exemplary embodiment 1 are higher than those of the OLED device of Exemplary embodiment 2, since each of the donor molecule and the receptor molecule provided in Exemplary embodiment 1 contains a large steric hindrance group. This further indicates that the donor and/or receptor material containing the large steric hindrance group enables to increase the inter-molecular distance between the donor molecule and the receptor molecule, decrease the overlapping degree between the HOMO and LUMO orbitals forming the exciplex body, and reduce the singlet-triplet energy level gap $\Delta E_{ST}$, thereby increasing the RISC rate ($k_{RISC}$) of the exciplex body, enhancing the Föster energy transfer to the guest molecule, and improving the efficiency of the organic electroluminescent device.

Figure 4:
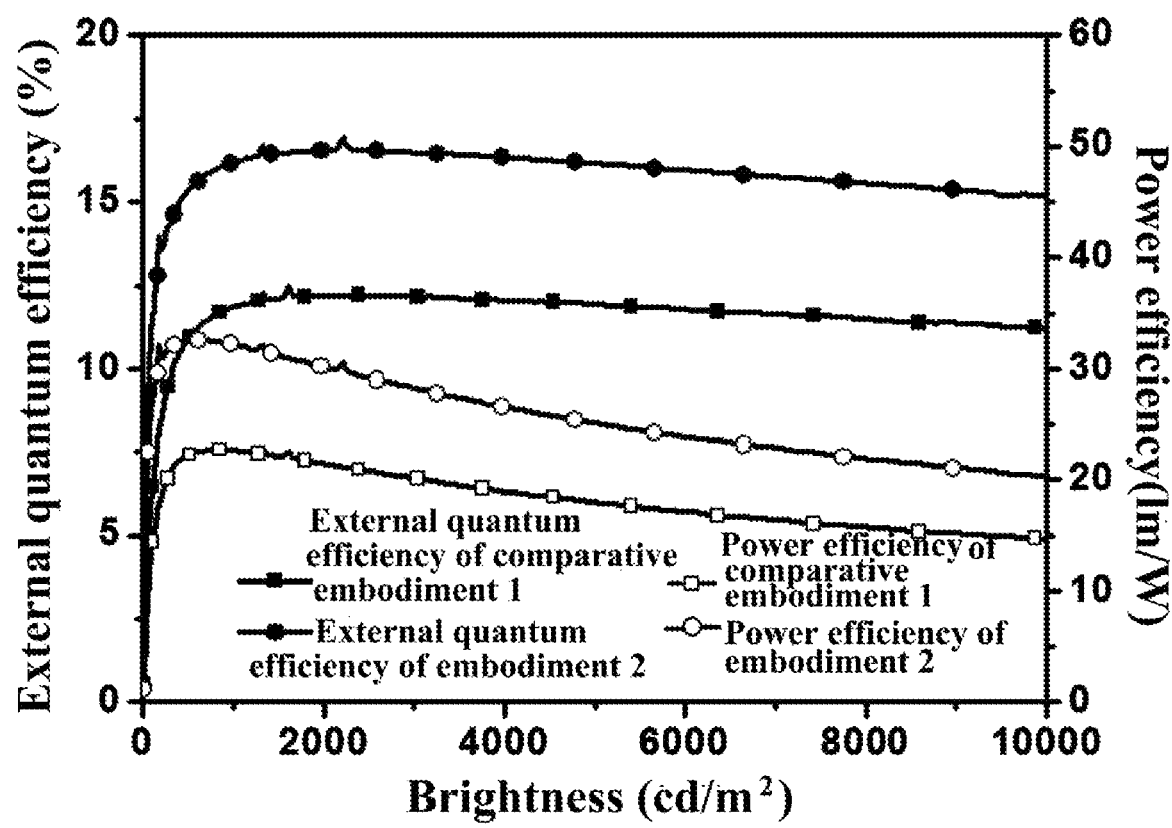
FIG. 4 is an external quantum efficiency-brightness-power efficiency diagram of Exemplary embodiment 2 and Comparative Exemplary embodiment 1 of the present disclosure.
Figure 5:
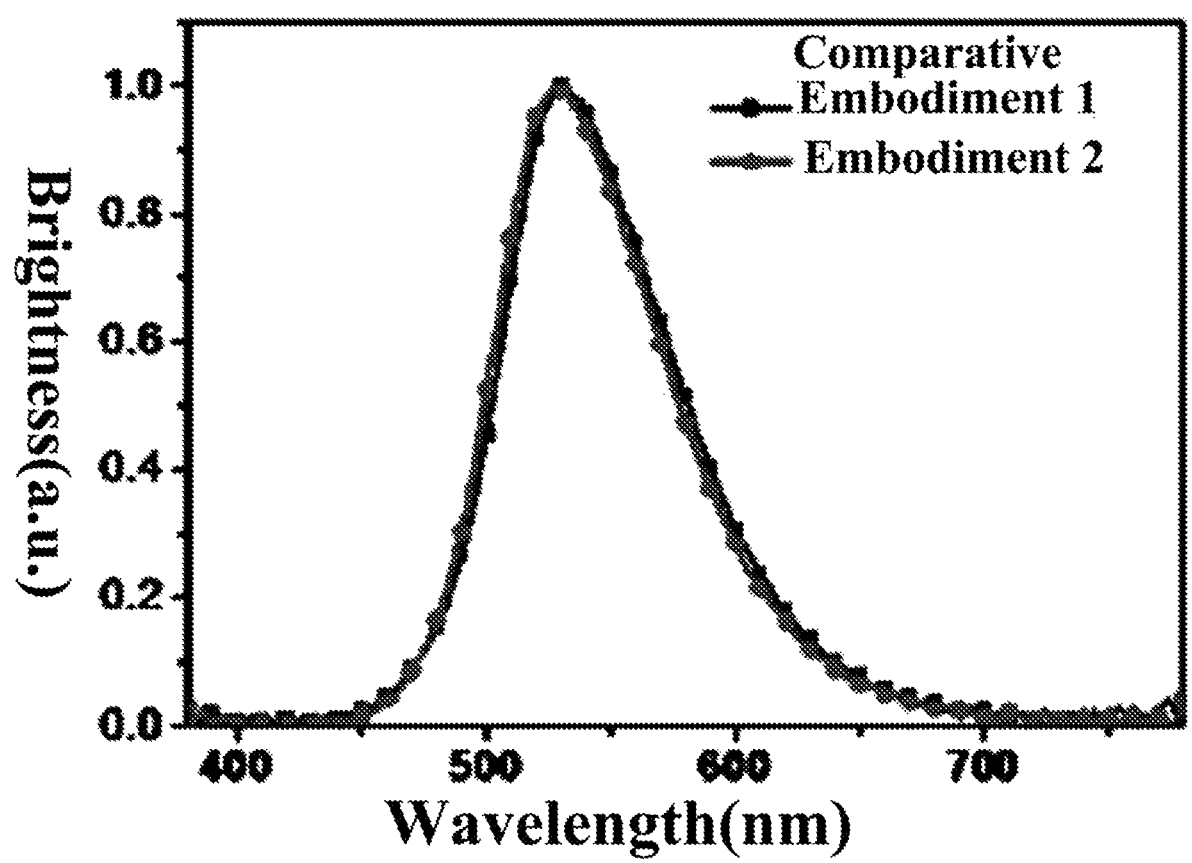
FIG. 5 is a luminescent spectrum of an organic electroluminescent device of Exemplary embodiment 2 and Comparative Exemplary embodiment 1 of the present disclosure.

As shown in FIG. 4, the ordinate is the external quantum efficiency and the power efficiency, and the abscissa is the brightness. The electroluminescence performance of the OLED device of Exemplary embodiment 2 is better than that of the OLED device of Comparative Exemplary embodiment 1 at the same brightness. This indicates that the device performance under the exciplex host material with a large steric hindrance group X (tert-butyl) is better than device performance under the exciplex host material without a large steric hindrance group, which is reflected in a higher external quantum efficiency and power efficiency. FIG. 5 shows the luminescence spectra of the organic electroluminescent devices of Exemplary embodiment 2 and Comparative Exemplary embodiment 1.

The lifetimes LT90 of Exemplary embodiment 1, Exemplary embodiment 2 and Comparative Exemplary embodiment 1 are tested at a constant brightness of 5000 cd/m², and Comparative Exemplary embodiment 1 is defined as a standard device having a lifetime of 1 equivalent. As can be seen from Table 1, the OLED devices of Exemplary embodiment 1 and Exemplary embodiment 2 both have an improved lifetime compared to the OLED device of Comparative Exemplary embodiment 1, and the OLED device of Exemplary embodiment 1 has the longest lifetime. Therefore, the introduction of a large steric hindrance group enables to effectively reduce the triplet concentration in the light-emitting layer, inhibit the TPA, and prolong the device lifetime.

II. The performances of the OLED devices of Exemplary embodiment 3, Exemplary embodiment 4, and Comparative Exemplary embodiment 2 are tested. The test results are shown in Table 2 below:

TABLE 2

Performance test of the OLED devices

| | Brightness (cd/m²) | External quantum efficiency | Power efficiency (lm/W) | Device lifetime LT90 | CIE color coordinate |
|---|---|---|---|---|---|
| Exemplary embodiment 3 | 5000 | 18.4% | 14.8 | 1.3 | (0.67, 0.33) |
| Exemplary embodiment 4 | 5000 | 17.6% | 13.2 | 1.1 | (0.67, 0.33) |
| Comparative Exemplary embodiment 2 | 5000 | 15.2% | 11.8 | 1 | (0.67, 0.33) |

As can be seen from Table 2, in the OLED devices prepared through the materials provided in Exemplary embodiment 3, Exemplary embodiment 4, and Comparative Exemplary embodiment 2, the guest luminescent materials are 1% doped phosphorescent material Ir(piq)₃. The external quantum efficiency and the power efficiency of the OLED devices of Exemplary embodiment 3 and Exemplary embodiment 4 are higher than those of the OLED device of Comparative Exemplary embodiment 2 at the same brightness. This indicates that the donor and/or receptor molecule containing the large steric hindrance group enables to decrease the overlapping degree between the HOMO and LUMO orbitals forming the exciplex body, and reduce the singlet-triplet energy level gap $\Delta E_{ST}$, thereby increasing the RISC rate ($k_{RISC}$) of the exciplex body, enhancing the Föster energy transfer to the guest molecule, improving the efficiency of the organic electroluminescent device, and achieving a better performance of the phosphorescent luminescent device. Since both the donor molecule and the receptor molecule have the large steric hindrance group X, the OLED device of Exemplary embodiment 3 has the best performance. Moreover, the doping concentration of the guest material is only 1%, which is low and thus results in a reduced device cost.

The lifetimes LT90 of Exemplary embodiment 3, Exemplary embodiment 4 and Comparative Exemplary embodiment 1 are tested at a constant brightness of 5000 cd/m², and Comparative Exemplary embodiment 2 is defined as a standard device having a lifetime of 1 equivalent. As can be seen from Table 2, the OLED devices of Exemplary embodiment 3 and Exemplary embodiment 4 both have an improved lifetime (LT90 is tested at a constant brightness of 5000 cd/m²) compared to the OLED device of Comparative Exemplary embodiment 2, which indicates that the introduction of the large steric hindrance group enables to effectively reduce the triplet concentration in the light-emitting layer, inhibit the TPA, and prolong the device lifetime.

It is apparent that the foregoing Exemplary embodiments are merely illustrated for clarity, and not intended to limit the embodiments. Other different forms of variations or modifications may also be made by a person skilled in the art on the basis of the foregoing description. There is no need and no way to exhaust all the embodiments herein. Obvious variations or modifications resulting therefrom still fall within the protection scope of the present disclosure.

What is claimed is:

1. An organic electroluminescent device, the organic electroluminescent device comprising an organic functional layer, the organic functional layer comprising a light-emitting layer; the light-emitting layer comprising a host material and a guest material; the host material being an exciplex composed of a donor molecule and a receptor molecule; the donor molecule and/or the receptor molecule containing a plurality of steric hindrance groups, wherein the steric hindrance groups are groups each independently containing substituted or unsubstituted cycloalkyl, silyl, boryl and borosilicate, wherein the donor molecule employs any one of the following structures:

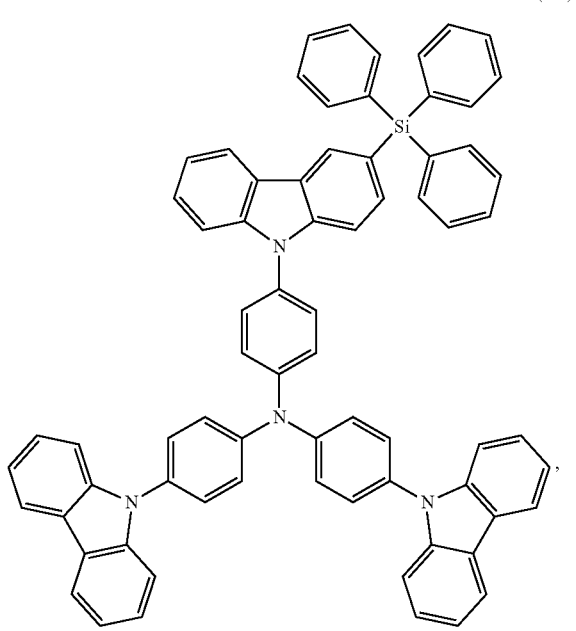

(1-2)

-continued
(1-7)
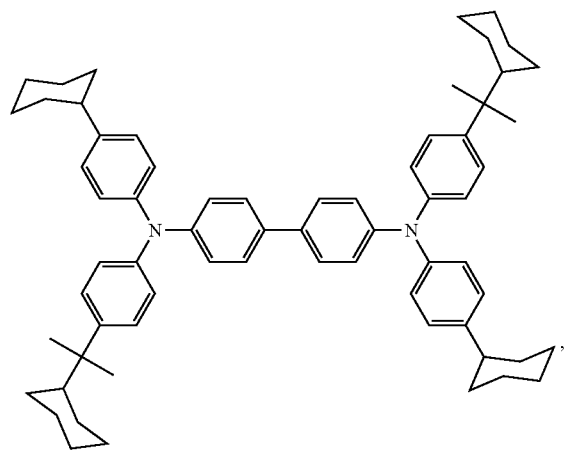
(1-9)
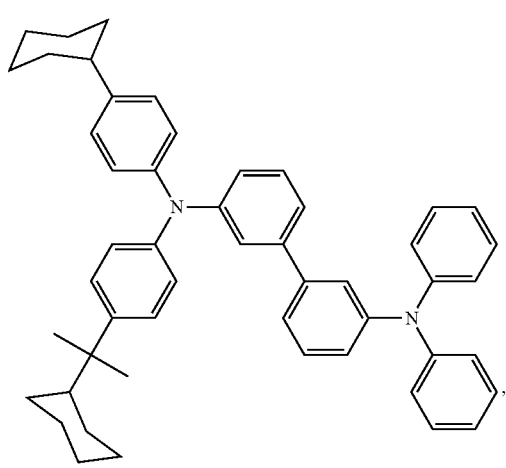
(1-16)
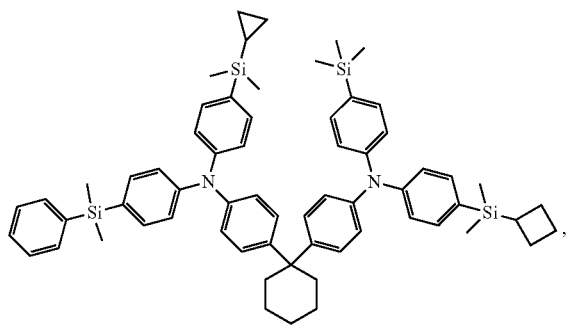
(1-17)
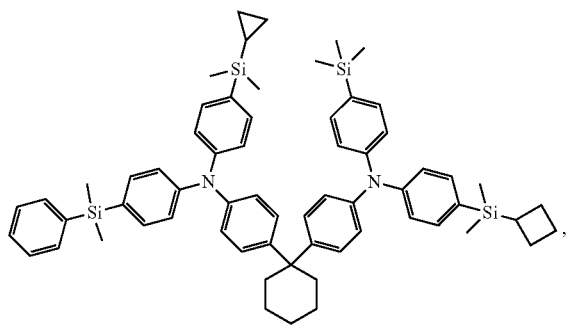
(1-18)
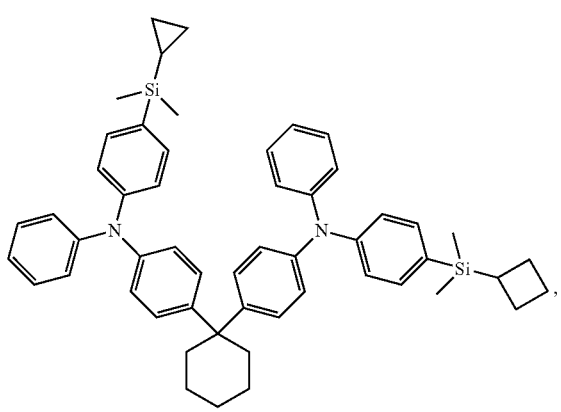
(1-19)
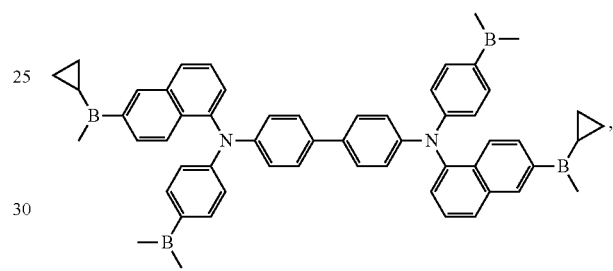
(1-20)
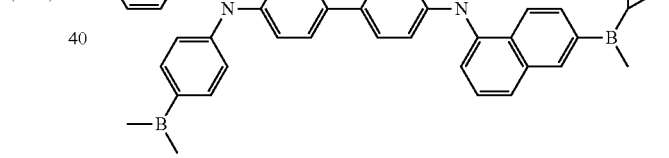
(1-21)
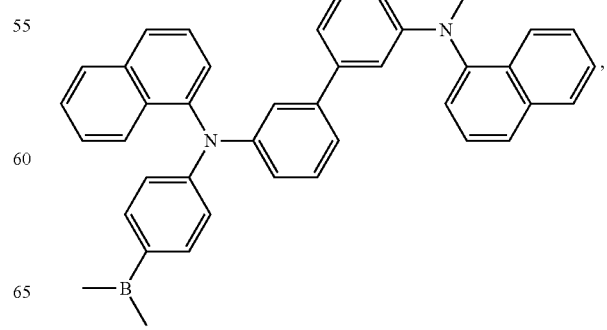

(1-22)

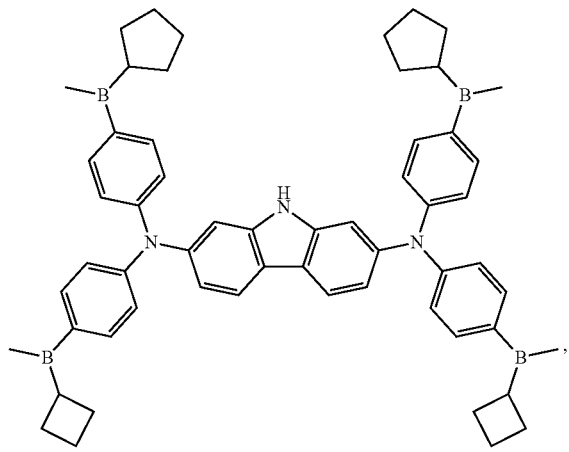

(1-24)

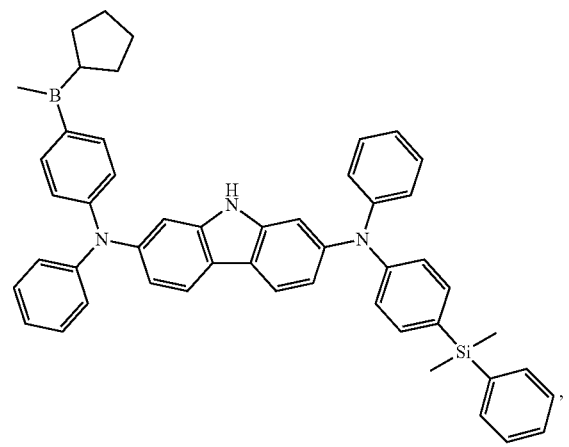

(1-25)

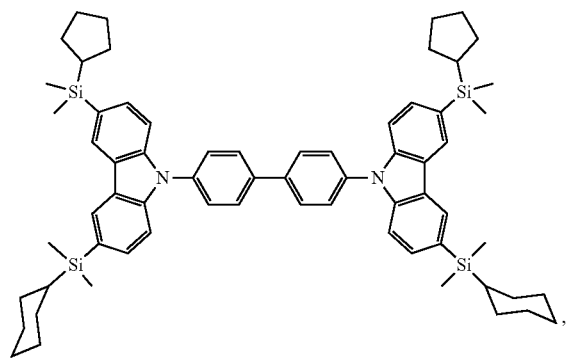

(1-26)

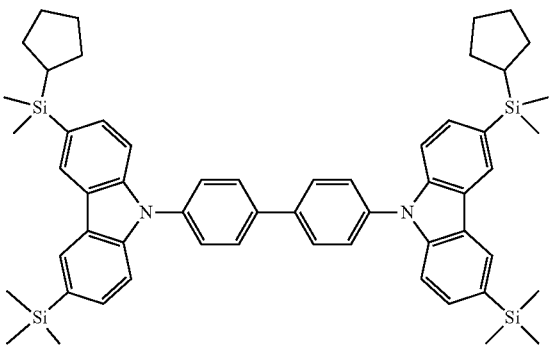

2. The organic electroluminescent device according to claim 1, wherein the receptor molecule is a compound containing at least one of pyrimidinyl, triazinyl, oxadiazolyl, pyridyl, carbazolyl, aryl, cyano, acridinyl, dibenzothiophenyl, triphenylphosphonyl, and triphenylboryl.

3. The organic electroluminescent device according to claim 2, wherein the receptor molecule employs any one of the following molecular structures:

(A-1)

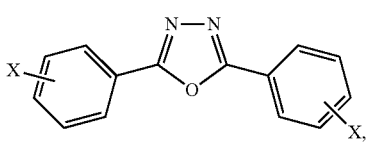

(A-2)

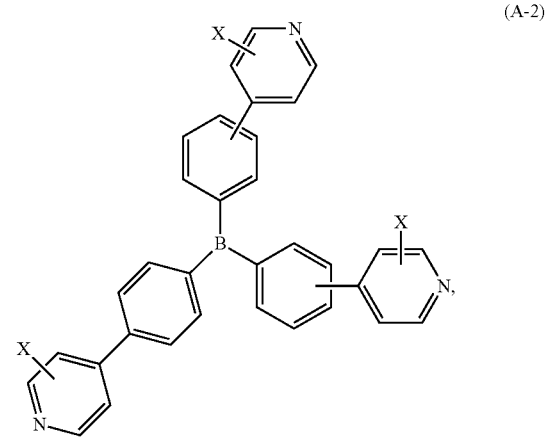

(A-3)

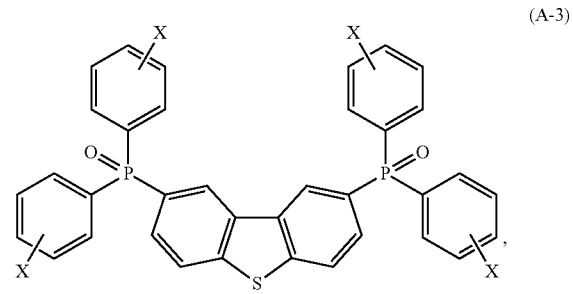

-continued
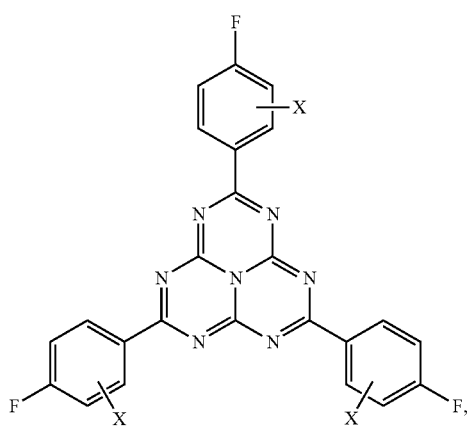
(A-4)
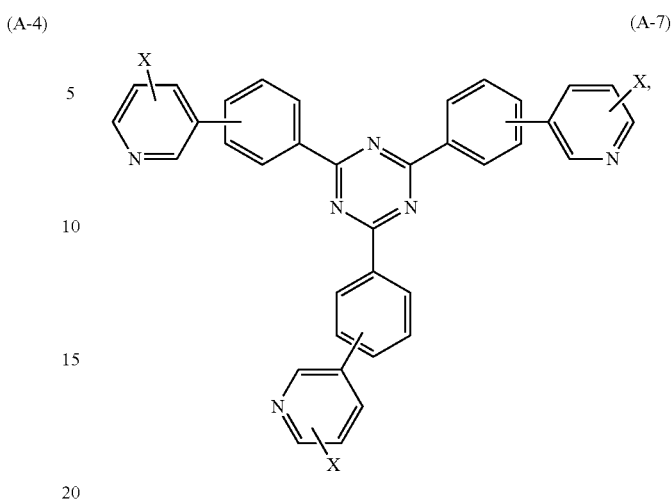
(A-7)
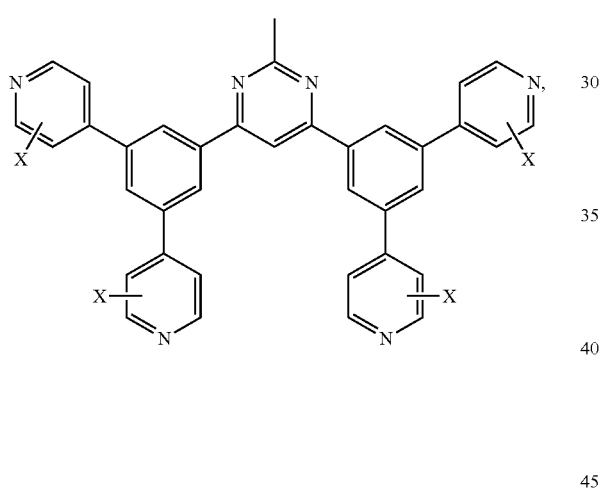
(A-5)
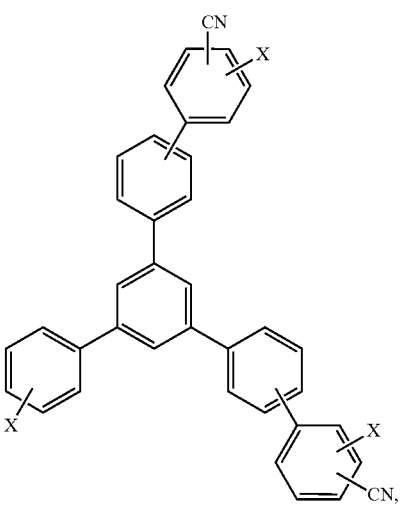
(A-8)
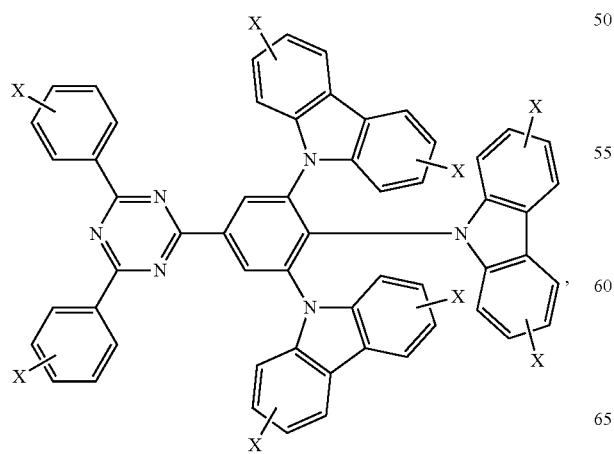
(A-6)
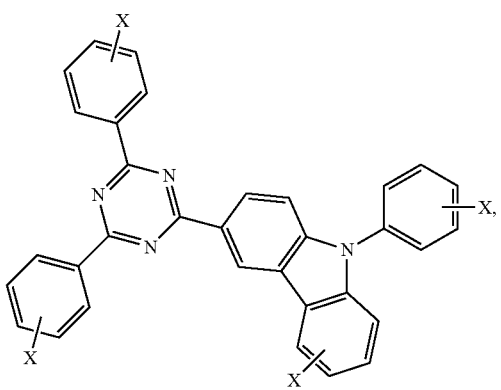
(A-9)

-continued
(A-10)
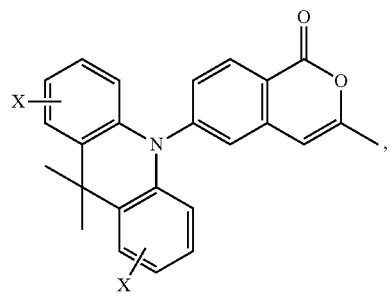
(A-11)
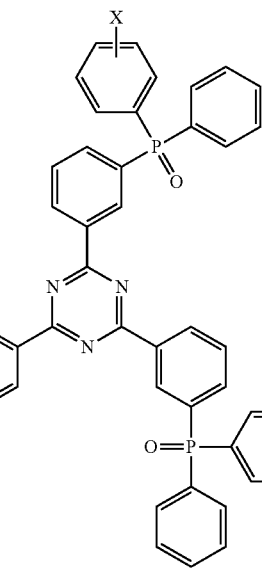
(A-12)
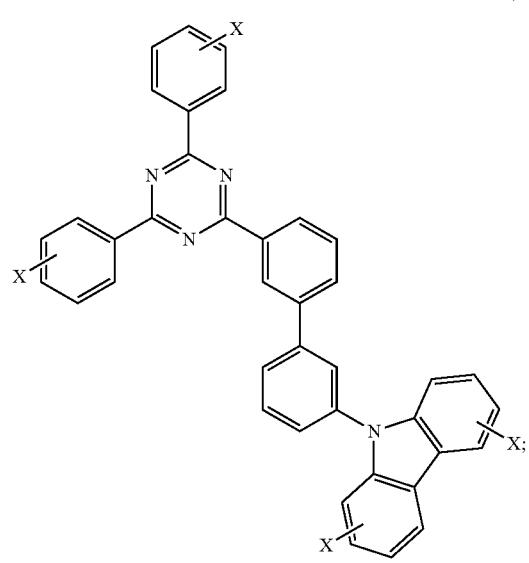
wherein X in the molecular structures is hydrogen or a steric hindrance group, and at least one X is a steric hindrance group.
4. The organic electroluminescent device according to claim 3,
wherein the receptor molecule employs any one of the following structures:
(2-1)
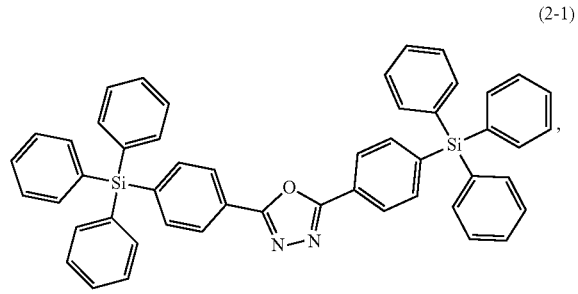
(2-2)
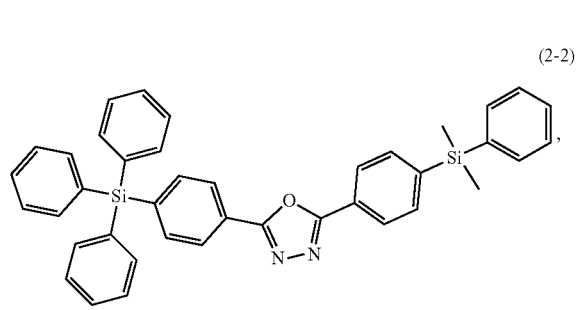
(2-3)
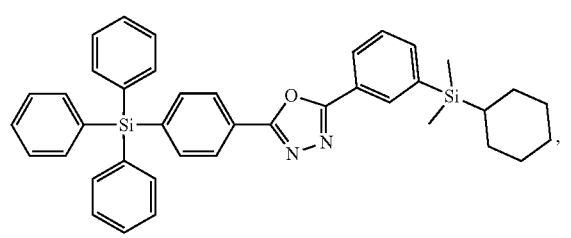
(2-4)
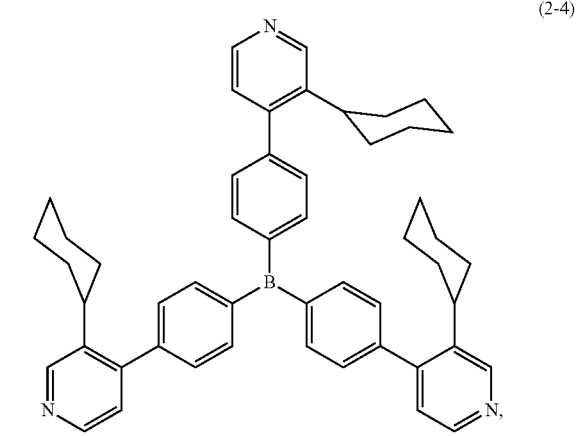

(2-5)
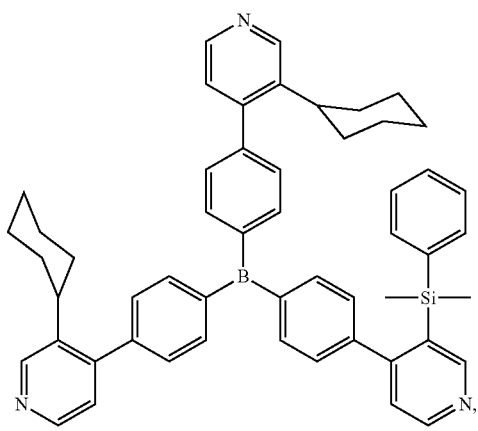
(2-16)
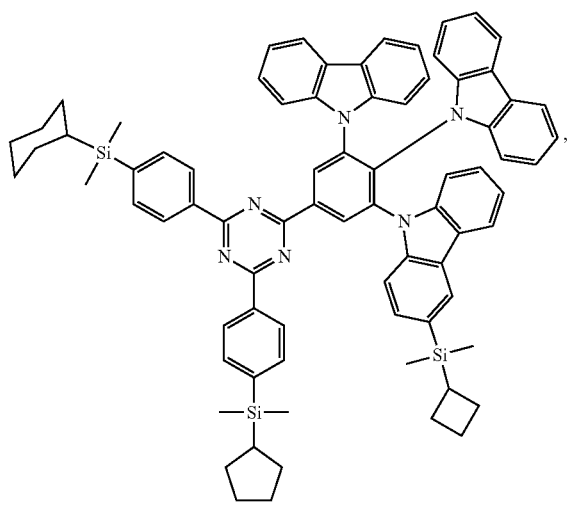
(2-12)
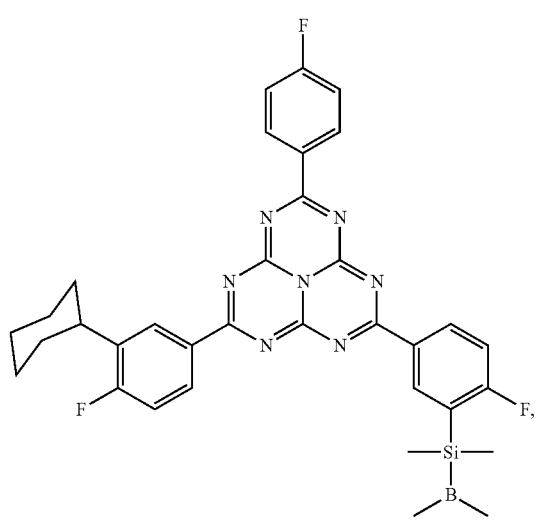
(2-17)
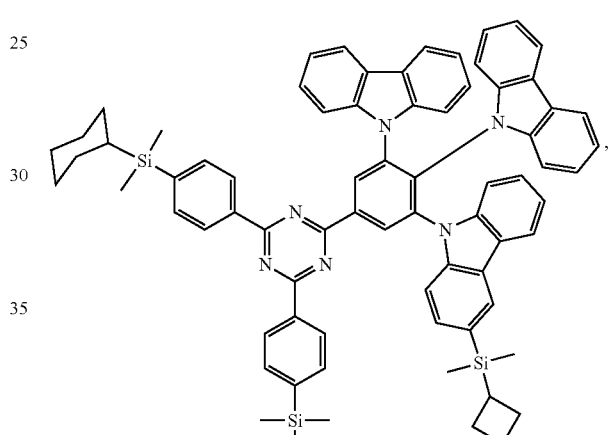
(2-15)
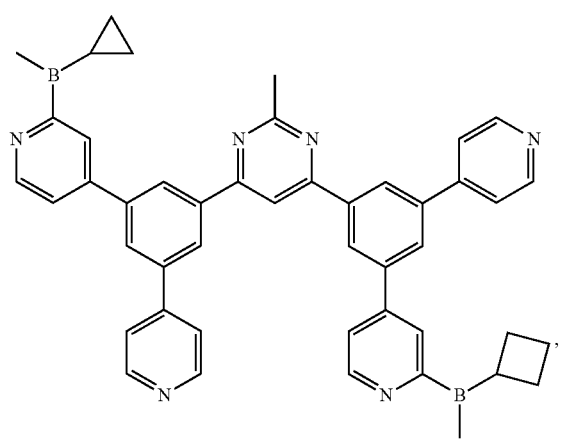
(2-18)
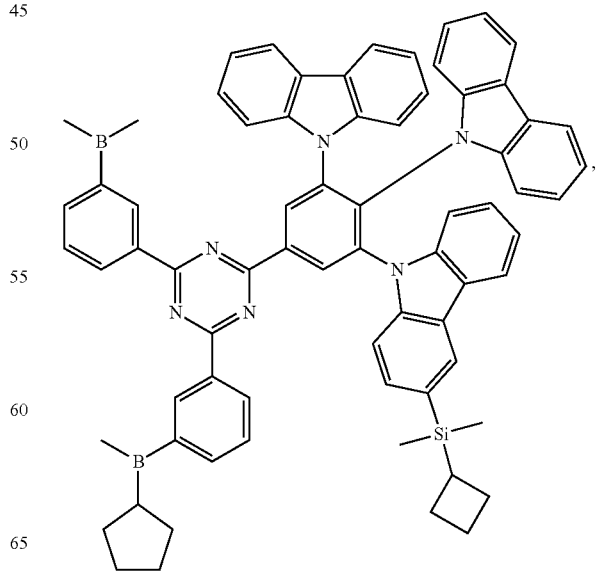

(2-22)
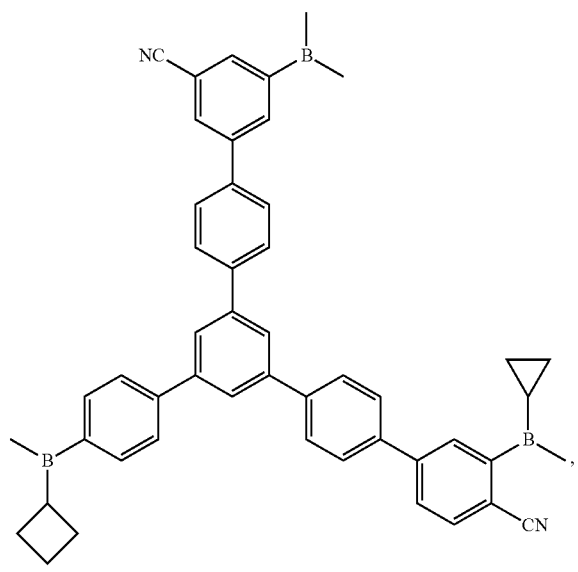
(2-24)
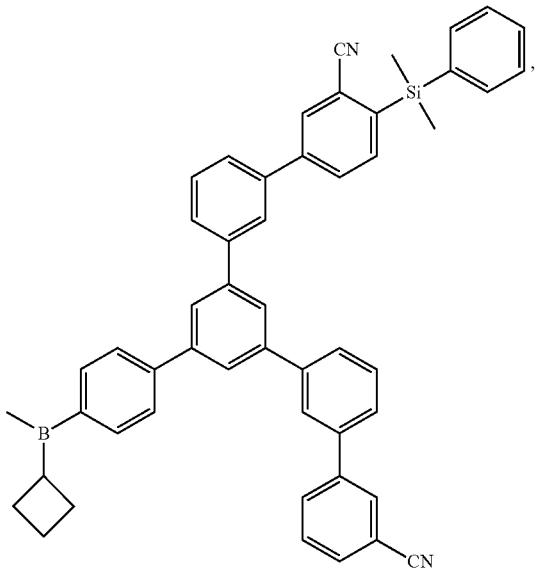
(2-26)
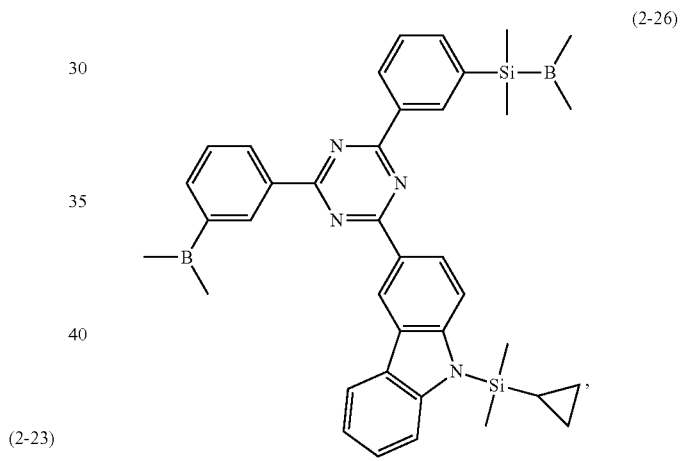
(2-23)
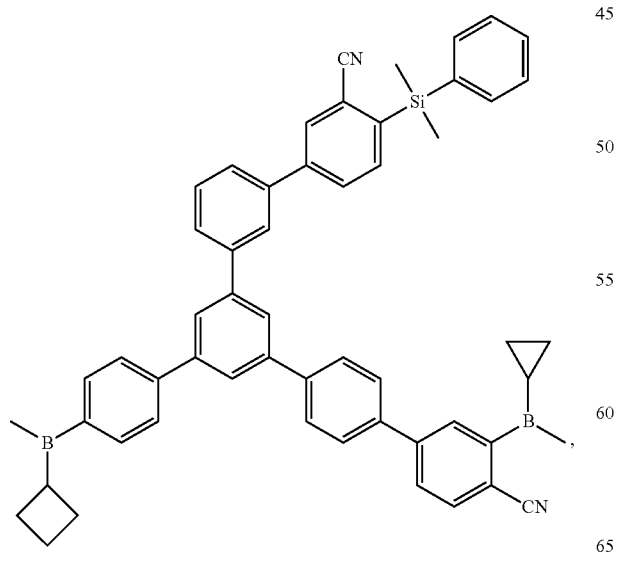
(2-27)
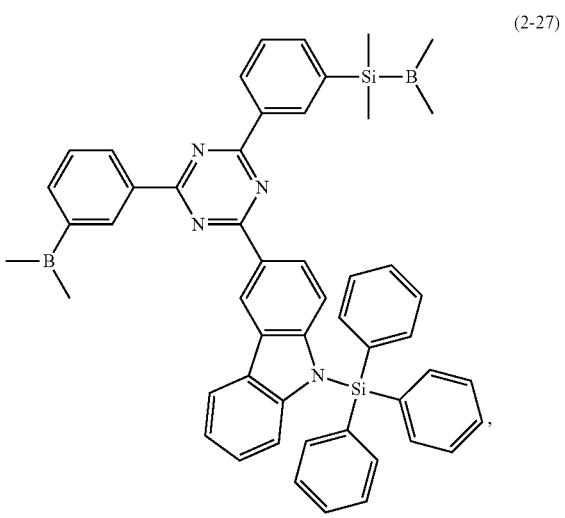

-continued (2-28)

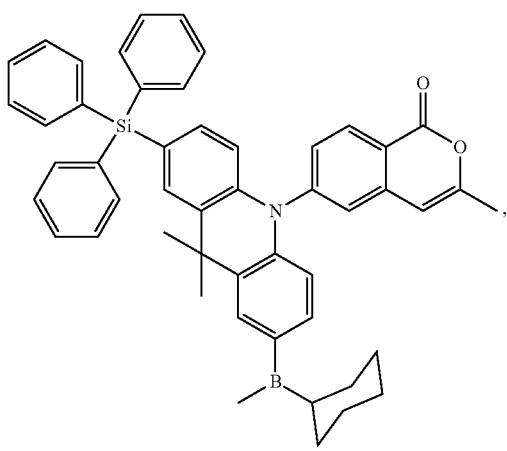

(2-29)

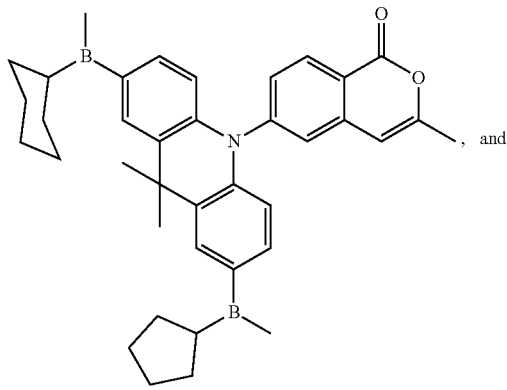
, and (2-31)

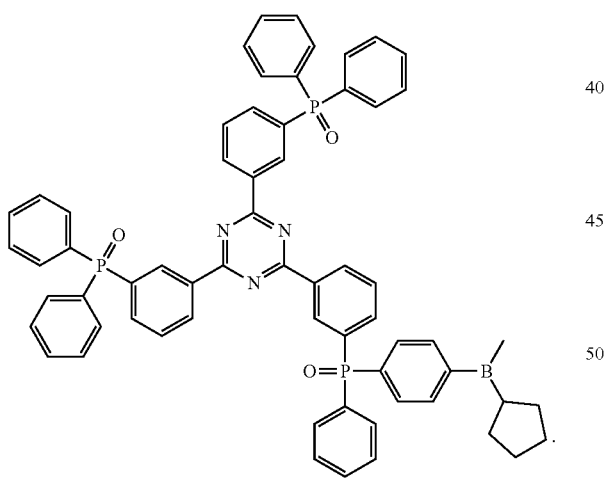

5. The organic electroluminescent device according to claim 1, wherein a number of steric hindrance groups on the donor molecule structure or the receptor molecule structure is less than or equal to six.

6. The organic electroluminescent device according to claim 1, wherein a mass ratio of the donor molecule to the receptor molecule in the exciplex is 1:9 to 9:1.

7. The organic electroluminescent device according to claim 6, wherein the mass ratio of the donor molecular material to the receptor molecular material is 1:2 to 1:5, or the mass ratio of the donor molecular material to the receptor molecular material is 2:1 to 5:1.

8. The organic electroluminescent device according to claim 1, wherein a mass ratio of the host material to the guest material is 1000:1 to 2:1.

9. The organic electroluminescent device according to claim 8, wherein the mass ratio of the host material to the guest material is 200:1 to 5:1.

10. The organic electroluminescent device according to claim 1, wherein the steric hindrance groups comprise:

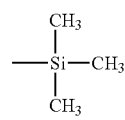 (X-4)

11. The organic electroluminescent device according to claim 1, wherein the steric hindrance groups are only selected from:

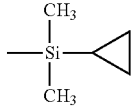 (X-10)

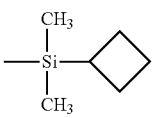 (X-11)

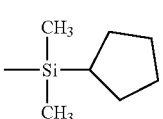 (X-12)

 (X-13)

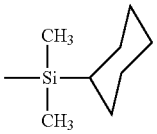 (X-14)

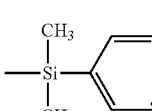 (X-15)

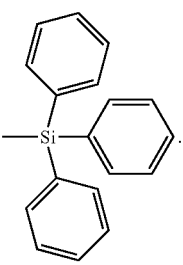 (X-16)

12. The organic electroluminescent device according to claim 1, wherein the steric hindrance groups are only selected from:

(X-18)
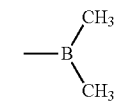

(X-19)
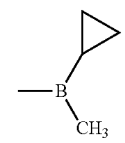

(X-20)
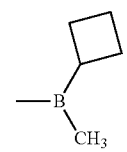

(X-21)
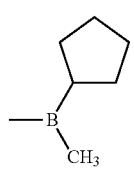

(X-22)
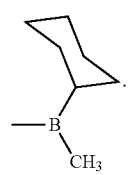

13. The organic electroluminescent device according to claim 1, wherein the steric hindrance groups comprise:

(X-17)
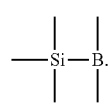

14. An organic electroluminescent device, the organic electroluminescent device comprising an organic functional layer, the organic functional layer comprising a light-emitting layer; the light-emitting layer comprising a host material and a guest material; the host material being an exciplex composed of a donor molecule and a receptor molecule; the donor molecule and/or the receptor molecule containing a plurality of steric hindrance groups, wherein the steric hindrance groups are groups each independently containing substituted or unsubstituted cycloalkyl, silyl, boryl, and borosilicate, wherein the donor molecule employs any one of the following structures:

(1-2)
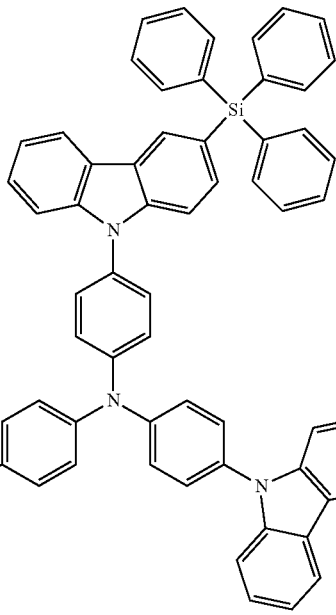

(1-7)
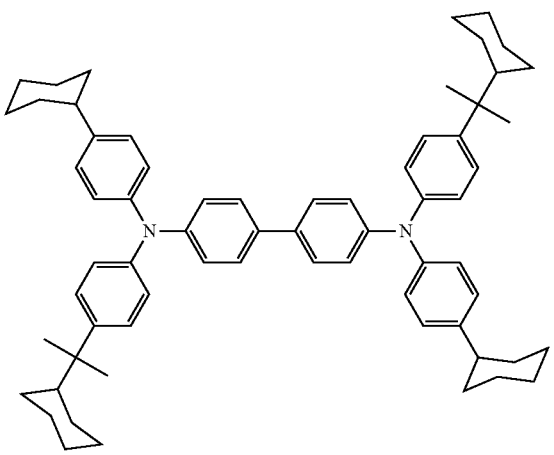

(1-9)
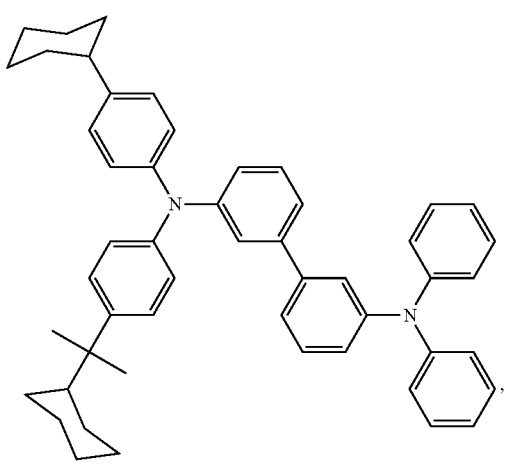

(1-16)
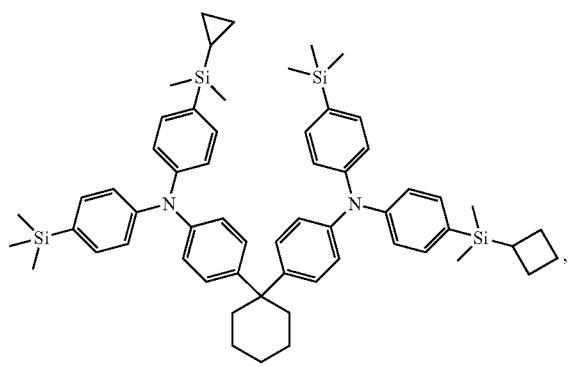
(1-17)
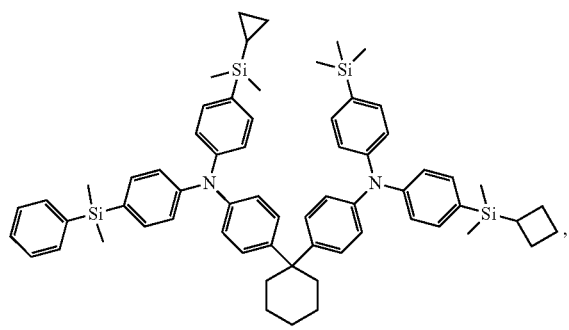
(1-18)
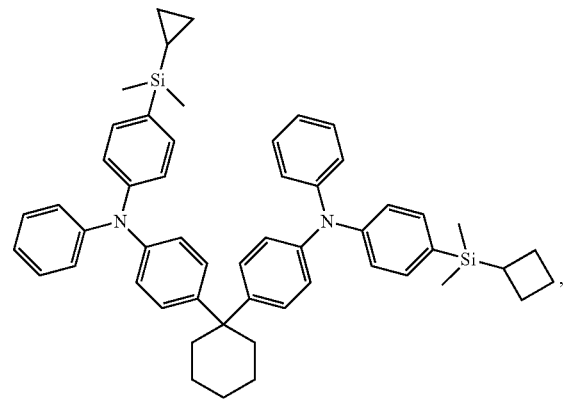
(1-19)
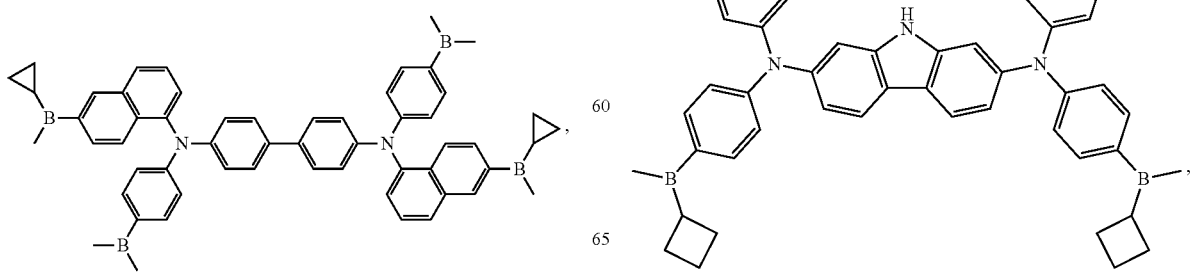
(1-20)
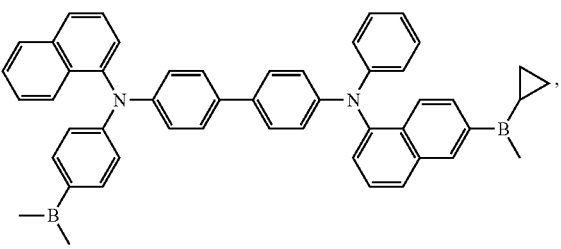
(1-21)
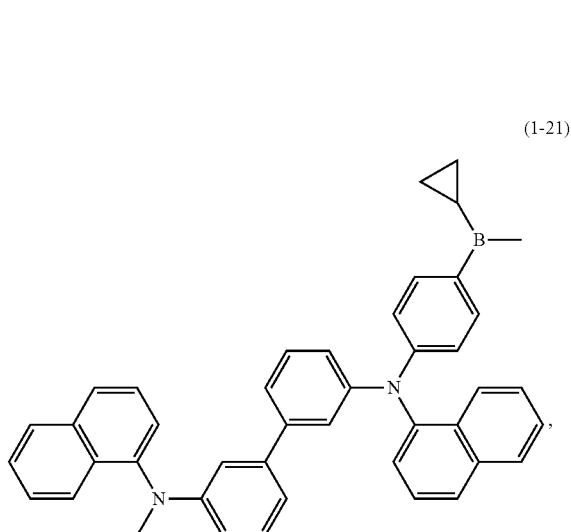
(1-22)
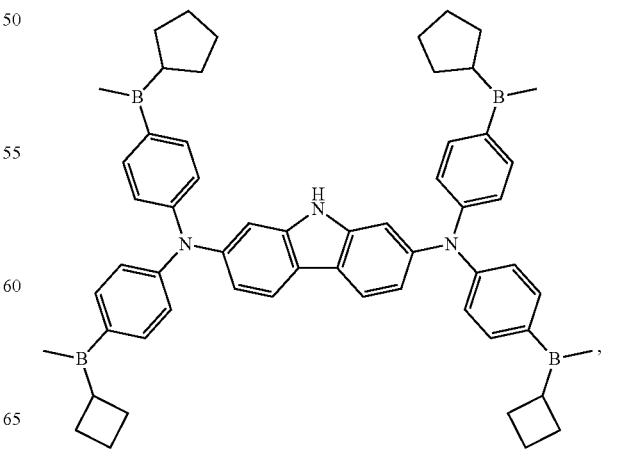

(1-24)

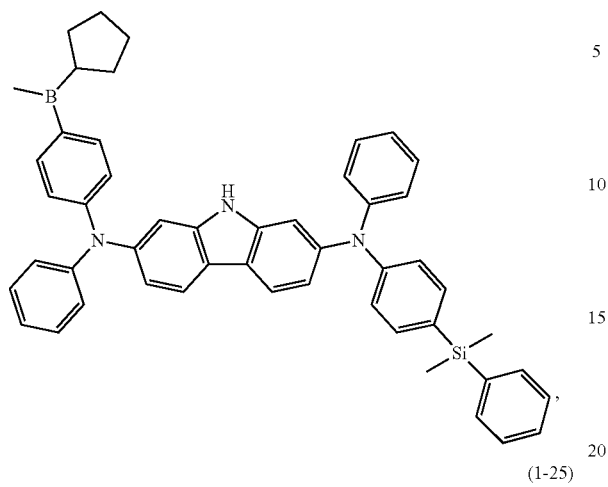

(1-25)

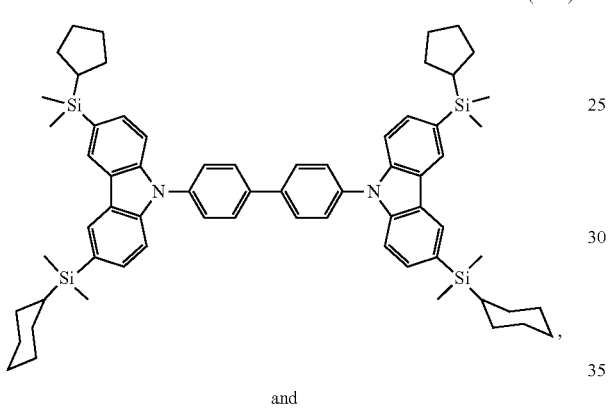

and (1-26)

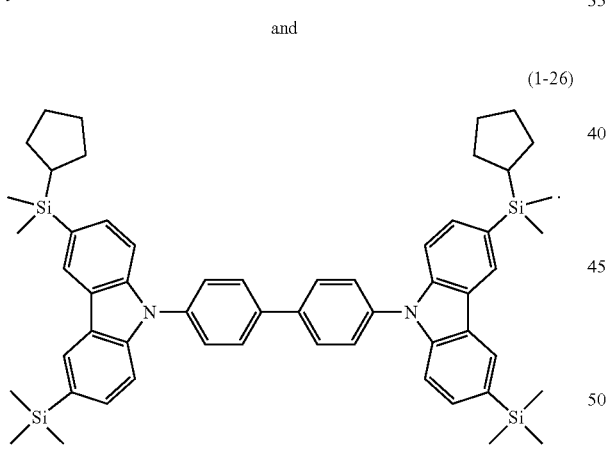

(A-1)

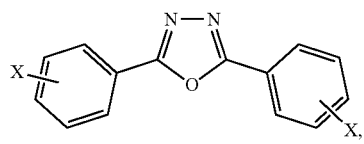

(A-2)

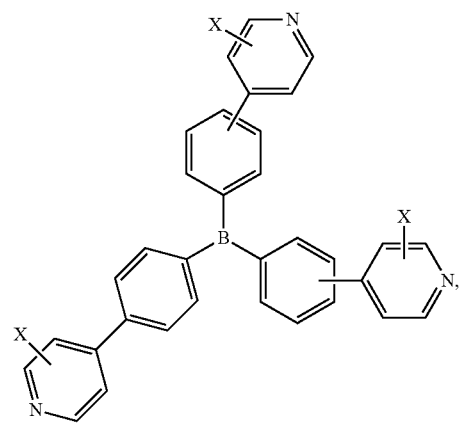

(A-3)

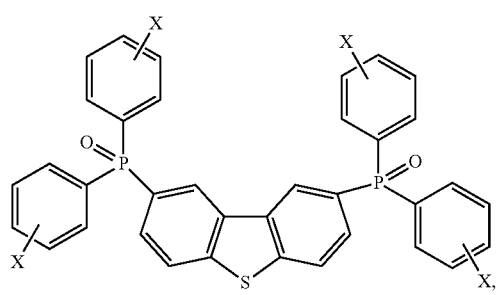

(A-4)

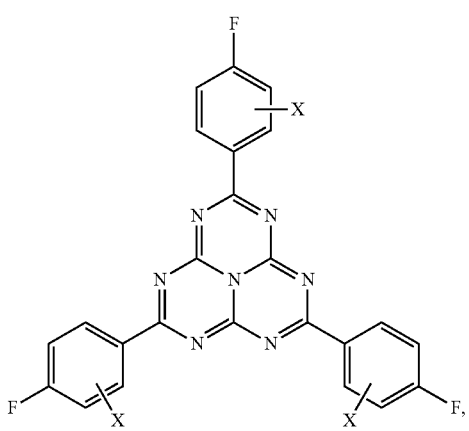

15. An organic electroluminescent device, the organic electroluminescent device comprising an organic functional layer, the organic functional layer comprising a light-emitting layer; the light-emitting layer comprising a host material and a guest material; the host material being an exciplex composed of a donor molecule and a receptor molecule; the donor molecule and/or the receptor molecule containing a plurality of steric hindrance groups, wherein the steric hindrance groups are groups each independently containing substituted or unsubstituted cycloalkyl, silyl, boryl, and borosilicate, and wherein the receptor molecule employs any one of the following molecular structures:

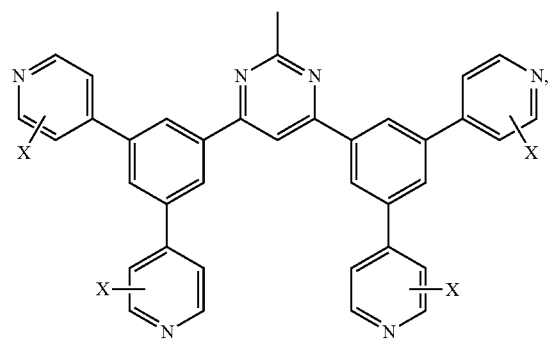
(A-5)
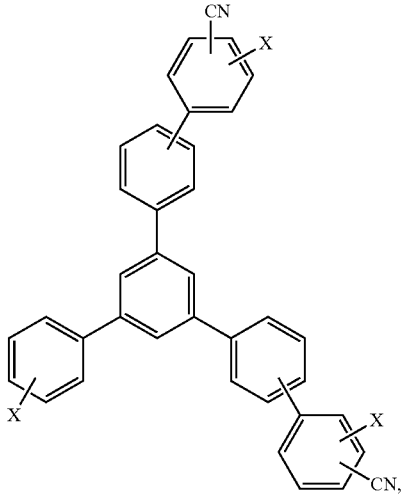
(A-8)
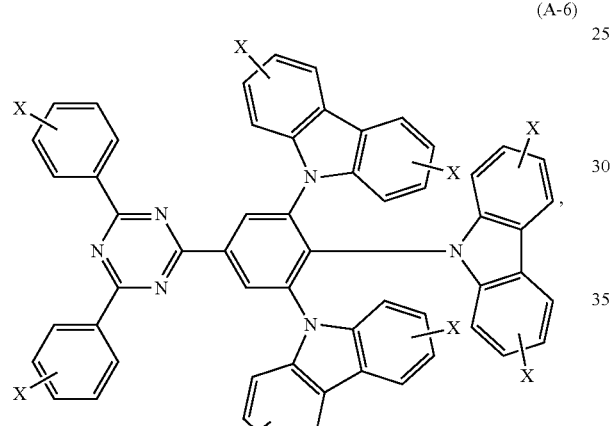
(A-6)
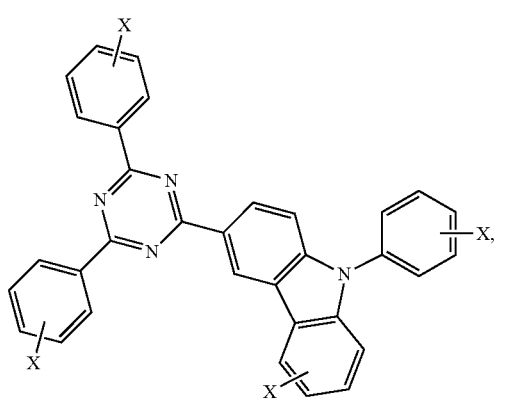
(A-9)
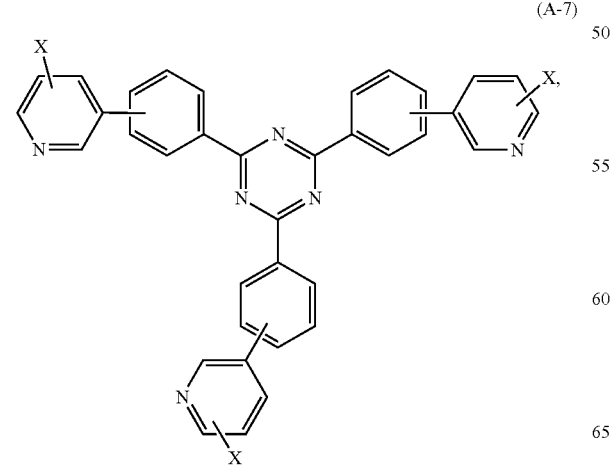
(A-7)
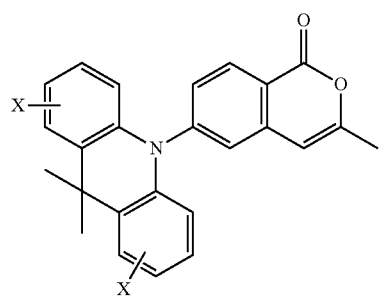
(A-10)

-continued
(A-11)
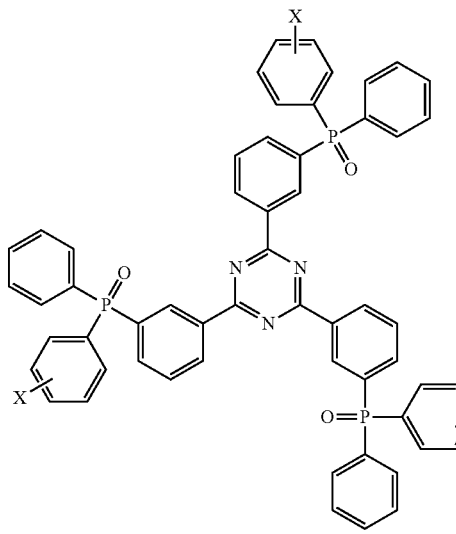
(A-12)
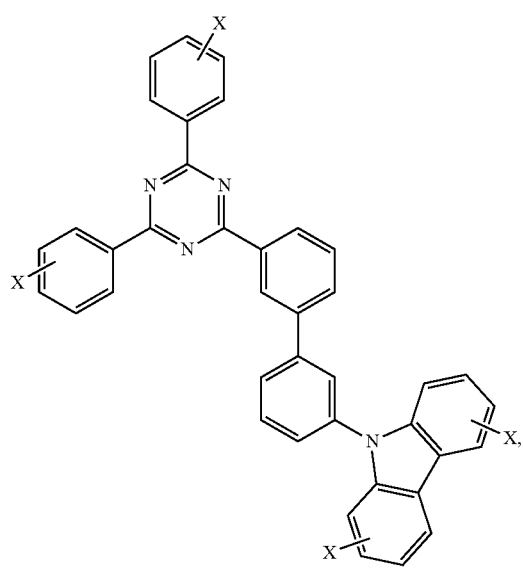
wherein X in the molecular structures is hydrogen or a steric hindrance group, and at least one X is a steric hindrance group,
wherein the donor molecule employs any one of the following structures:
(1-2)
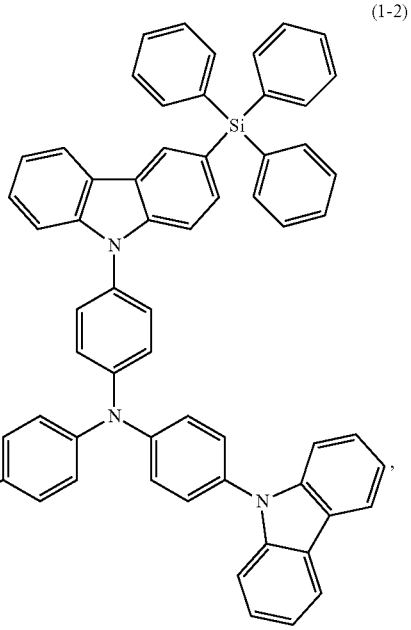
(1-7)
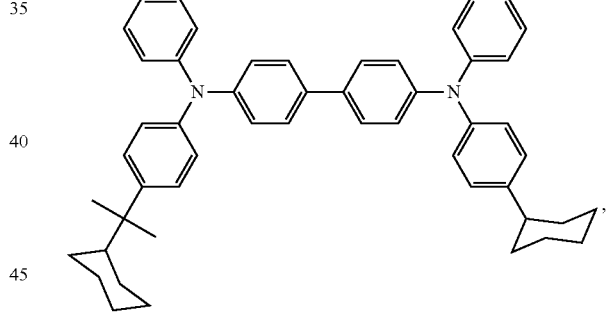
(1-9)
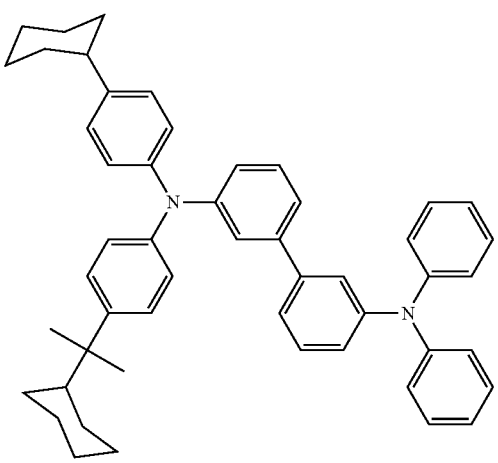

-continued
(1-16)
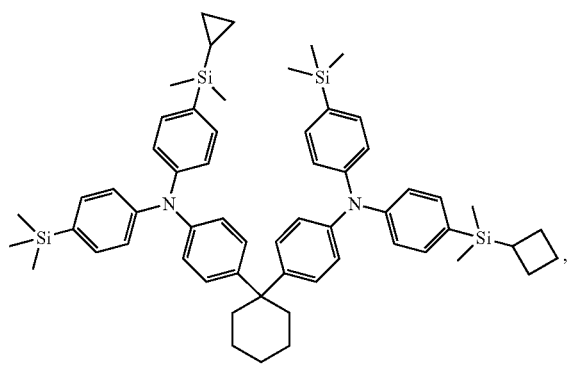
(1-17)
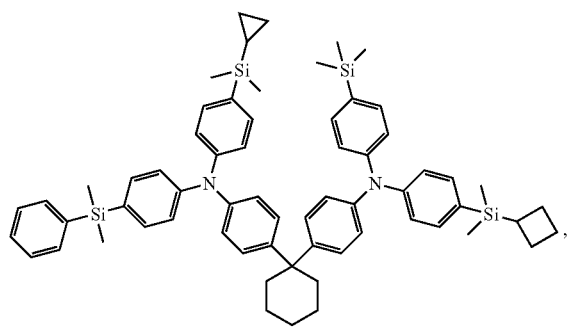
(1-18)
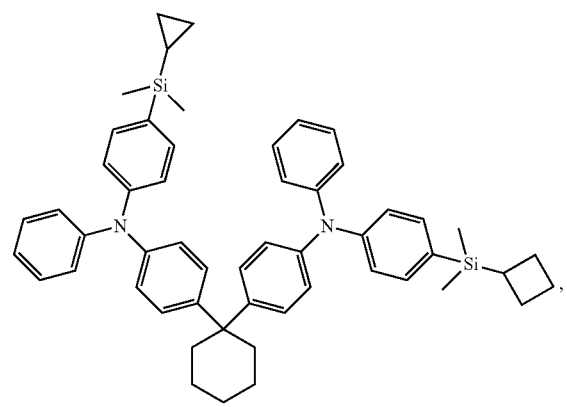
(1-19)
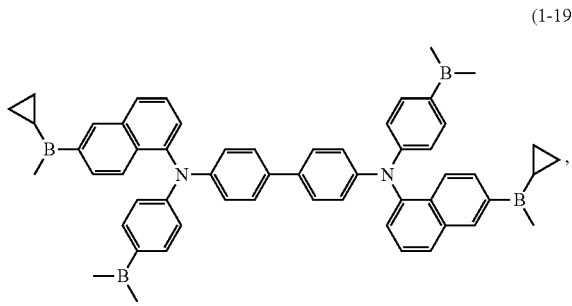
-continued
(1-20)
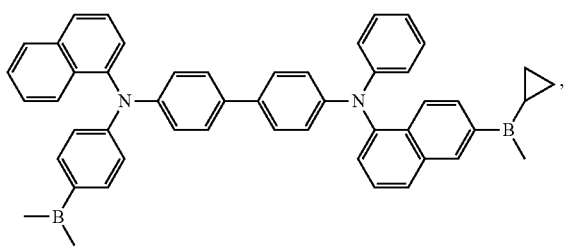
(1-21)
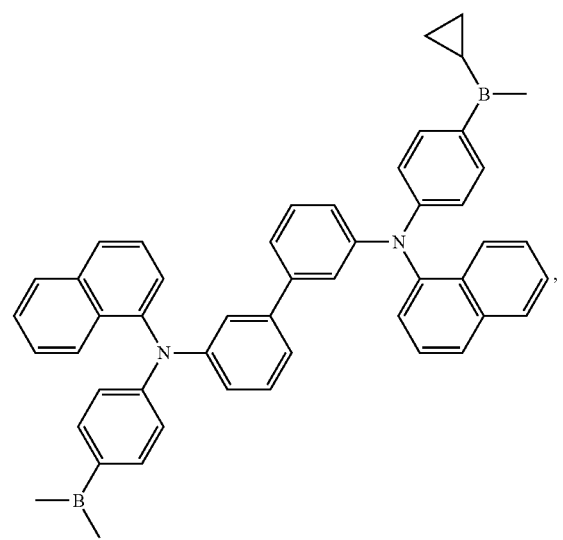
(1-22)
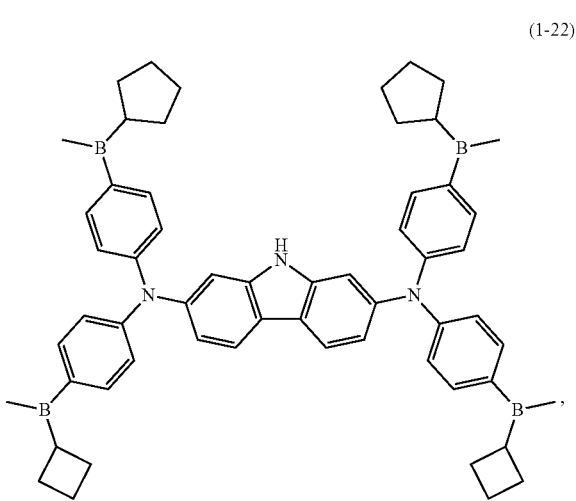

(1-24)
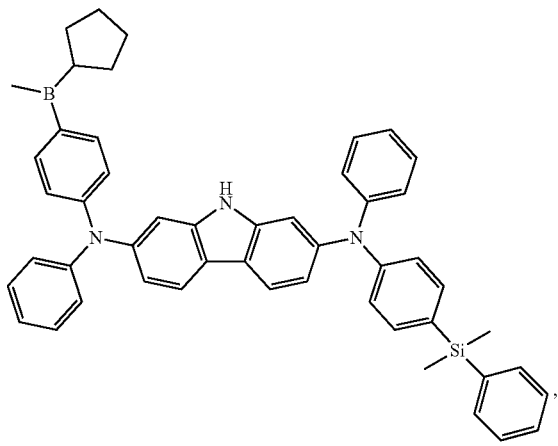
(1-25)
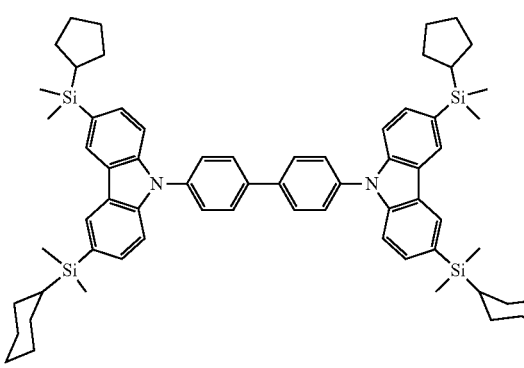
and
(1-26)
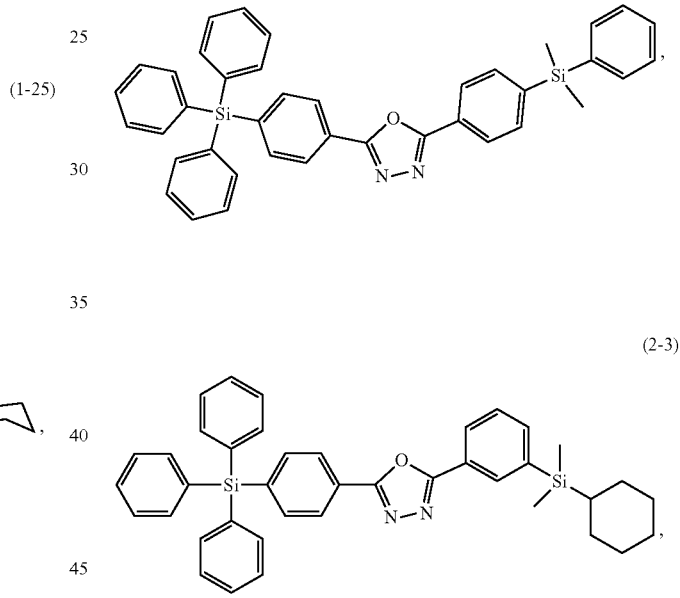
16. The organic electroluminescent device according to claim 15, wherein the receptor molecule employs any one of the following structures:
(2-1)
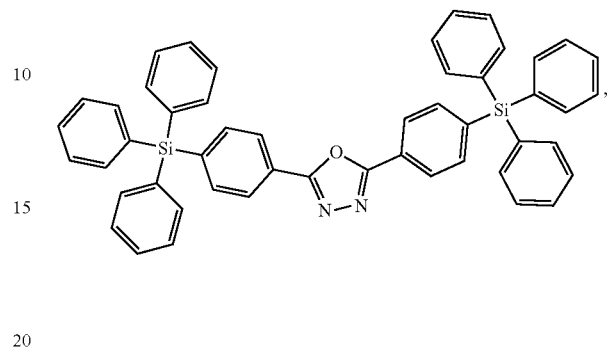
(2-2)
(2-3)
(2-4)
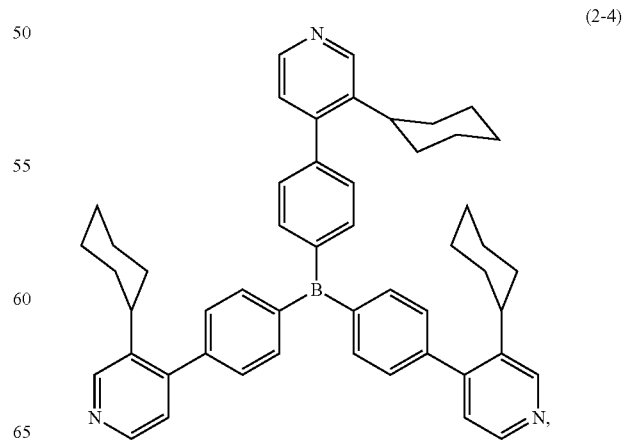

83
-continued
(2-5)
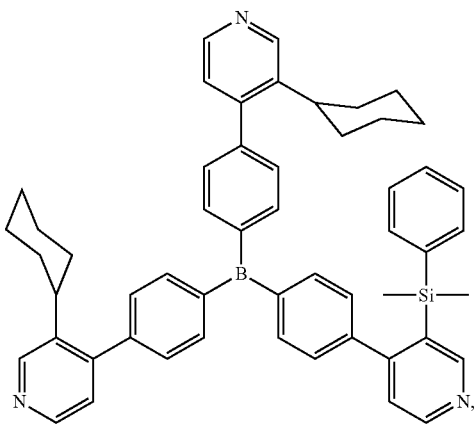
(2-12)
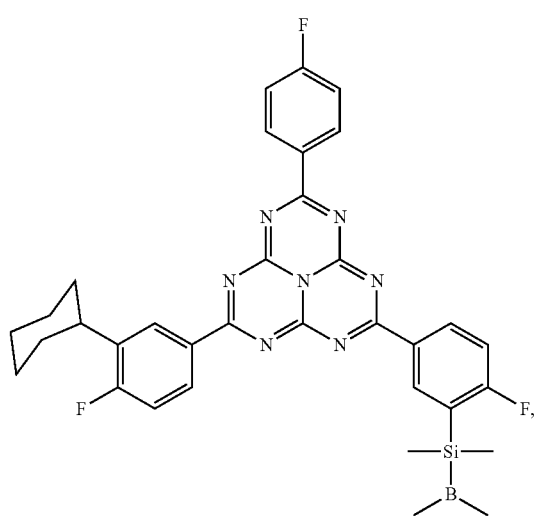
(2-15)
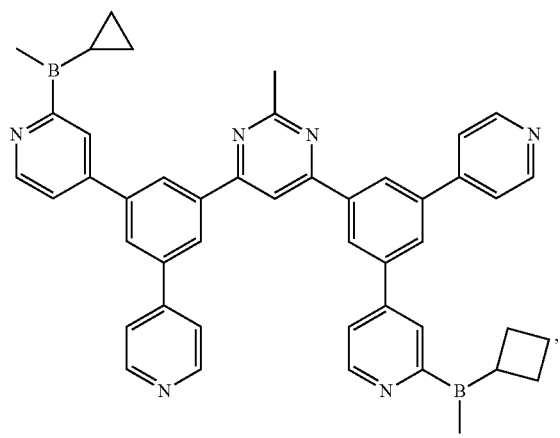
84
-continued
(2-16)
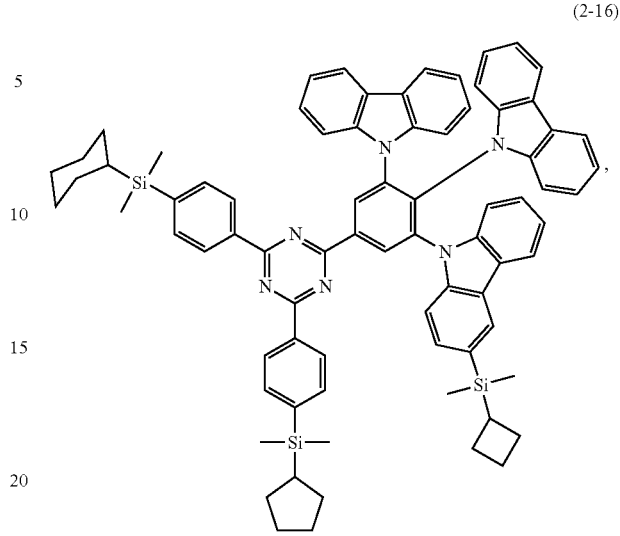
(2-17)
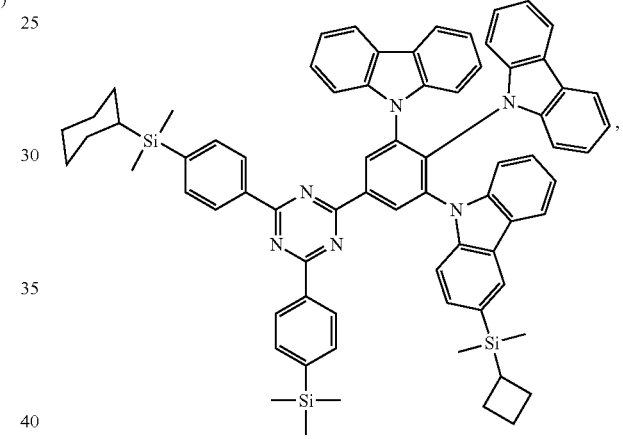
(2-18)
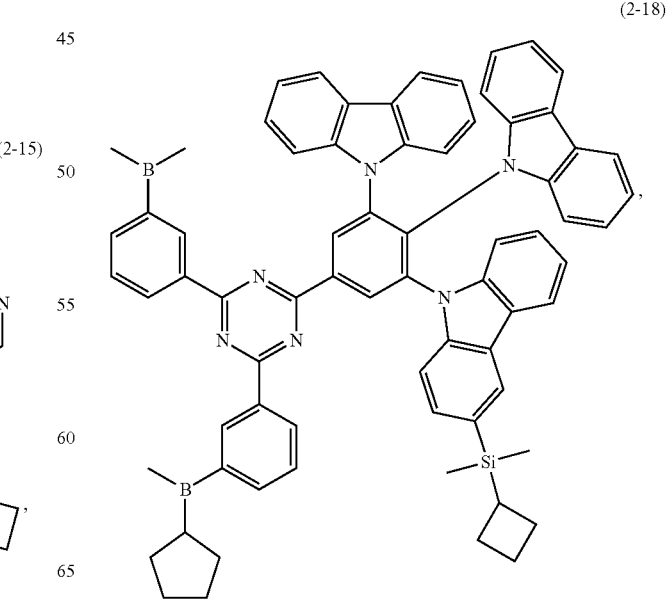

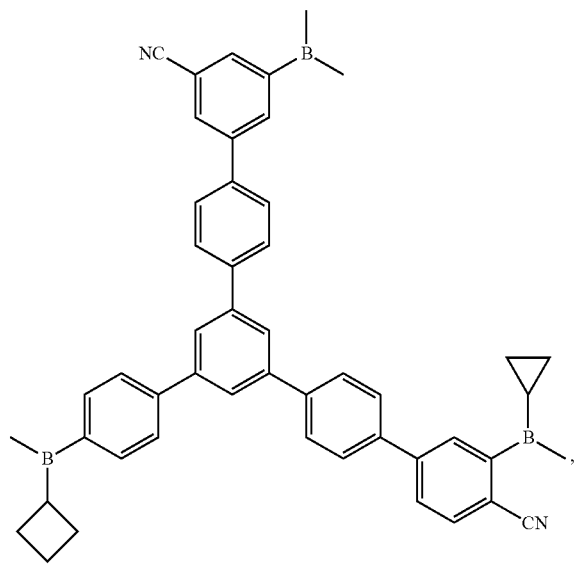
(2-22)
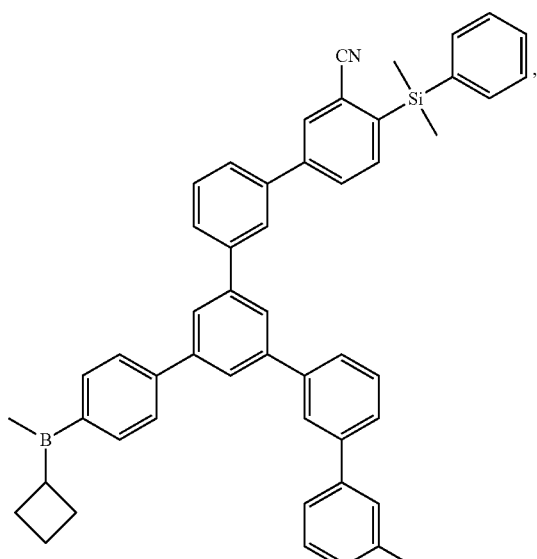
(2-24)
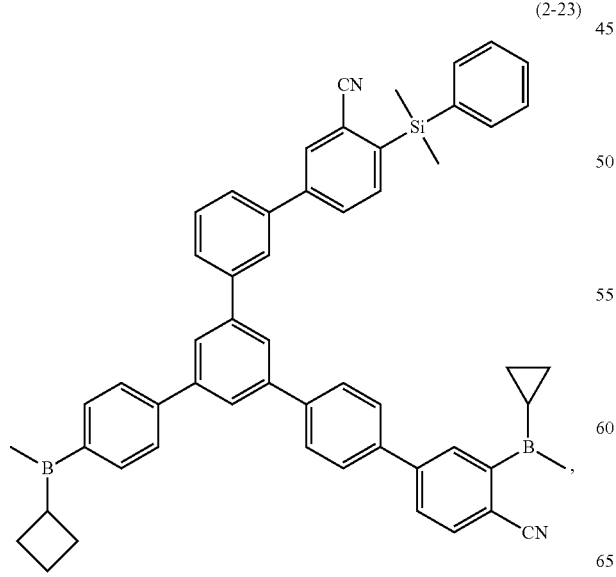
(2-23)
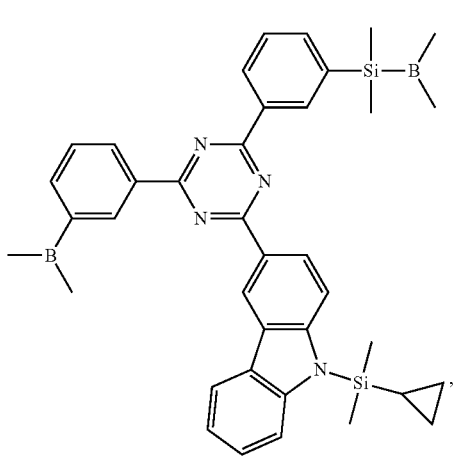
(2-26)

(2-27)
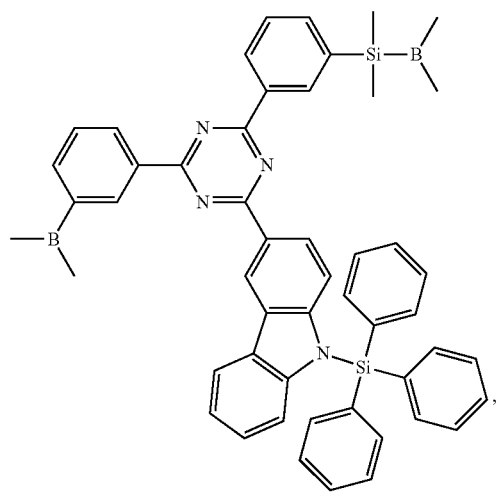
(2-28)
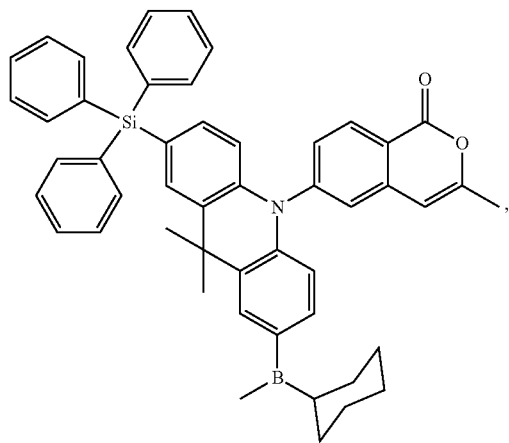
(2-29)
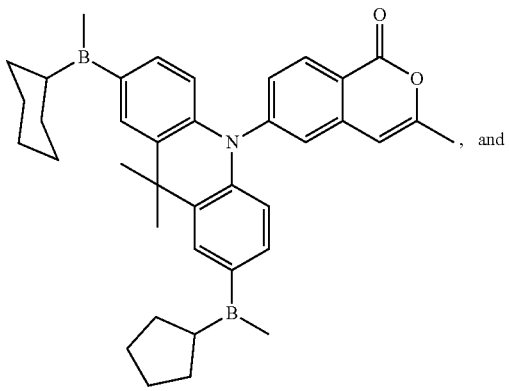
, and
(2-31)
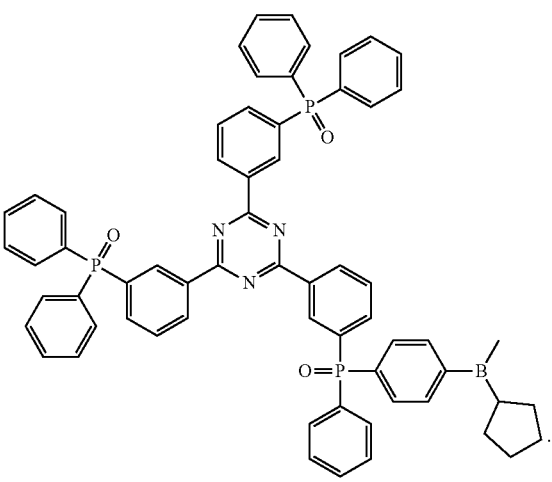
* * * * *